(12) United States Patent
Chen et al.

(10) Patent No.: US 9,062,004 B2
(45) Date of Patent: Jun. 23, 2015

(54) CANNABINOID-2 AGONISTS

(75) Inventors: June Chen, San Juan Capistrano, CA (US); Simon Pettit, Colchester (GB); Hans Fliri, Saffron Waldon (GB)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/576,872

(22) PCT Filed: Feb. 7, 2011

(86) PCT No.: PCT/US2011/023867
§ 371 (c)(1),
(2), (4) Date: Nov. 13, 2012

(87) PCT Pub. No.: WO2011/097553
PCT Pub. Date: Aug. 11, 2011

(65) Prior Publication Data
US 2013/0059848 A1 Mar. 7, 2013

Related U.S. Application Data

(60) Provisional application No. 61/302,384, filed on Feb. 8, 2010.

(51) Int. Cl.
*A01N 43/58* (2006.01)
*A61K 31/50* (2006.01)
*C07D 237/02* (2006.01)
*C07D 237/22* (2006.01)
*C07D 487/04* (2006.01)

(52) U.S. Cl.
CPC ............ *C07D 237/22* (2013.01); *C07D 487/04* (2013.01)

(58) Field of Classification Search
USPC .......................................... 544/224; 514/247
See application file for complete search history.

(56) References Cited

U.S. PATENT DOCUMENTS 3,287,105 A * 11/1966 Reicheneder et al. ........ 504/237
4,366,155 A * 12/1982 Canada .......................... 514/247
5,097,028 A    3/1992 Weissmuller et al.

FOREIGN PATENT DOCUMENTS

| WO | 2005-007632 A1 | 1/2005 |
| WO | 2005-061504 A1 | 7/2005 |
| WO | 2007-014226 A2 | 2/2007 |

OTHER PUBLICATIONS

St. John et al., Interactions of chemicals with plant membranes Beltsville Symposia in Agricultural Research (1985), 8(Agric. Chem. Future), 211-222 CODEN: BSARDN; ISSN: 0160-3612; English.*
Konecny et al., Synthesis, spectral properties, and pesticidal activity of 4-amino(alkylamino, dialkylamino)-5-chloro-2-substituted-3-oxo-2H-pyridazines and 5-amino(alkylamino, dialkylamino)-4-chloro-2-substituted-3-oxo-2H-pyridazines Collection of Czechoslovak Chemical Communications (1985), 50(2), 492-502 CODEN: CCCCAK; ISSN: 0366-547X; English.*
Terlizzi et al., Pyridazinones and soybean oil quality AOCS Monograph (1984), 11(Biotechnol. Oils Fats Ind.), 107-17 CODEN: AOMODZ; ISSN: 0731-4183.*
St. John et al. Interactions of chemicals with plant membranes Beltsville Symposia in Agricultural Research (1985), 8(Agric. Chem. Future), 211-222 CODEN: BSARDN; ISSN: 0160-3612.*
Anna Katrusiak, et al, Reactivity of 6-Chloro-4-and 5-Hydrazino-2-phenyl-3(2H)-pyridazinones with Vilsmeier Reagent, Tetrahedron, 1994, 12933-12940, 50 (45).
Anu Kauppinen et al., CB2 receptor as a potential target in age-related diseases, Journal of Biochemical and Pharmacological Research, Mar. 2014, pgs. 33-43, vol. 2, No. 1.
Kenji Kaji, et al., Synthesis of Pyrazolo[3,4-d]pyridazines from 5-(1-Methylhydrazino) . . . , Chemical and Pharmaceutical Bulletin, 1985, 982-988, 33.
Kurt Pilgram, 4(And 5)-Cyclopropylamino-5(and 4)halo-3(2H)pyridazinones . . . , J. Heterocyclic Chem., Jan. 1, 1977, 1039-1043, 14.
Maria Irbarne et al., Cannabinoid Receptors in Conjunctival Epithelium: Identfication and Functional Properties, Investigative Ophthalmology & Visual Science, Oct. 2008, pp. 4535-4544, vol. 49, No. 10.
Patent Cooperation Treaty, Notification of Transmittal of the Intermational Search Report & The Written Opinion of the Intl Searching Authority, or the Declaraion, Form PCT/ISA/220, Int. App. No. PCT/US2011/023867, May 24, 2011, pp. 16.
Tougri et al., CB2 Receptor Activiation is Anti-Inflammatory in a Endotoxin-Induced Uveitis Model, Proceedings of the British Pharmacological Society, [Retrieved from http://www.pa2online.org/abstracts/1vol11issue1abst004.pdf] (Downloaded Jun. 27, 2014) 1 page, vol. 11, abst 004.
Vaclav Konecny, et al., Synthesis, Spectral Properties, and Pesticidal Activity of 4-Amino(Alkylamino, Dialkylamino)-5-Chloro-2-Substituted-3 . . . , Collection Czechoslovak Chem, Commun., 1985, 492-502, 50.
Von Dr. K. Dury, Neue Wege in der Chemie der Pyridazone, Angewandte Chemie, 1965, 282-290, 77 (7).

* cited by examiner

*Primary Examiner* — Paul V Ward
(74) *Attorney, Agent, or Firm* — Jonathan Y. Bass

(57) ABSTRACT

The present specification discloses cannabinoid-2 agonists, compositions comprising such cannabinoid-2 agonists, and methods of treating an individual suffering from a disease by administering compositions comprising such cannabinoid-2 agonists. (Formula I and III)

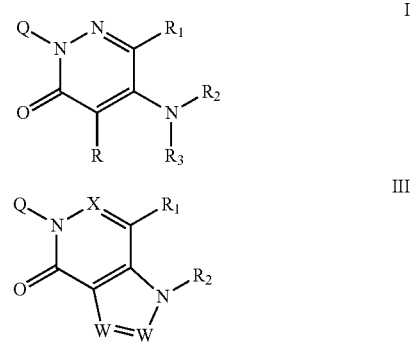

8 Claims, No Drawings

CANNABINOID-2 AGONISTS

CROSS REFERENCE TO RELATED APPLICATIONS

This is a national stage application under 35 U.S.C. §371 of PCT patent application PCT/US11/23867, filed on Feb. 7, 2011, which claims the benefit of U.S. Provisional Patent Application No. 61/302,384, filed on Feb. 8, 2010, the disclosure of which is incorporated herein by reference in its entirety.

BACKGROUND

Cannabinoids are lipid-based compounds that can be divided into endogenous cannabinoids (endocannabinoids), which are generated naturally inside the body, from exogenous cannabinoids, which are introduced into the body as *cannabis* or a related synthetic compound. The physiological effects of cannabinoids are mediated by at least two high-affinity cannabinoid receptors, CB1 and CB2, located in the cell membrane. Belonging to a class of G-protein coupled receptor (GPCR) family, CB1 and CB2 share about 44% amino acid sequence identity. Both CB1 and CB2 receptors couple to the inhibitory G-protein alpha-subunit Gi and $G_o$. Receptor activation thus leads to inhibition of adenylate cyclase, thereby the production of the second messenger molecule cyclic AMP, as well as to activation of mitogen activated protein kinase (MAPK). In addition, under certain conditions and with certain agonists, the CB1 and CB2 receptors couple to $G_s$ and $G_{q11}$. Furthermore, CB1 and CB2 receptor activation also although appears to have distinct downstream effects on other intracellular signal transduction pathways, such as, e.g., potassium ion channels, calcium channels, protein kinase A and C, Raf-1, ERK, JNK, p38, c-fos, c-jun, depending on the cell type. D. G. Demuth and A. Molleman, *Cannabinoid Signaling*, Life Sci. 78(6): 549-563 (2006). CB1 receptors can also modulate ion channels, inhibiting N-, and P/R-type calcium channels, stimulating inwardly rectifying K channels and enhancing the activation of the A-type K channel.

The therapeutic use of cannabinoids dated back at least 4,000 years to the ancient dynasties of China and includes applications for various illnesses ranging from lack of appetite, emesis, cramps, menstrual pain, spasticity to rheumatism. The long history of medicinal use of cannabinoids has led to the development of several modern pharmaceutical drugs. For example, MARINOL (generic name dronabinol) and CESAMET (generic name nabilone), two synthetic cannabinoids based on THC, are prescribed anti-emetic and for enhancement of appetite, mainly in AIDS patients. In addition to their clinical use as an antiemetic, potential therapeutic uses of nonselective cannabinoid receptor agonists include the management of multiple sclerosis, spinal cord injury, pain, inflammatory disorders, glaucoma, bronchial asthma, vasodilatation that accompanies advanced cirrhosis, and cancer. See e.g., Y. Cheng and S. A. Hitchcock, Targeting Cannabinoid Agonists for Inflammatory and Neuropathic Pain, Expert Opin. Investig. Drugs 16(7): 951-965 (2007); B. G. Ramíirez, et al., *Prevention of Alzheimer's Disease Pathology by Cannabinoids: Neuroprotection Mediated by Blockade of Microglial Activation*, J. Neurosci. 25(8): 1904-1913 (2005).

However, despite the clinical benefits, the therapeutic usage of current cannabinoid agonists is limited by their clinically undesirable psychotropic side-effects, such as, e.g., hallucination, addiction, and dependence. With the discovery that these psychotropic side-effects were mediated by the CB1 receptor, great interest has been focused on identifying CB2 selective agonists in an effort to develop pharmaceutical drugs that lack the psychotropic side-effects associated with nonselective CB1/CB2 cannabinoid agonists. See e.g., Meyyappan Muthuppalaniappan, et al., Novel Cannabinoid Receptor Ligands, Pharmaceutical Compositions Containing Them, and Processes for Their Preparation, U.S. Patent Publication 2008/0200501; Chunjian Liu, et al., Indole Indane Amide Compounds Useful as CB2 Agonists and Method, U.S. Patent Publication 2009/0041722; Timothy C. Gahman, et al., Heterocyclodiazeoine Cannabinoid Receptor Modulators for Treatment of Disease, U.S. Patent Publication 2009/0062253; Tomoki Kato, et al., Sulfonyl Benzimidazole Derivatives, U.S. Patent Publication 2009/0137584; Liotta Fina, et al., Hexahydro-Cycloheptapyrazole Cannabinoid Modulators, US Patent Publication 2009/0197886; Mingde Xia, et al., Method for Treating CB2 Receptor Mediated Pain, U.S. Patent Publication 2009/0215850; and Doria Riether, et al., Compounds which Modulate the CB2 Receptor, U.S. Patent Publication 2009/0275611; each of which is hereby incorporated by reference in its entirety.

The present specification discloses novel CB2 agonist useful for treating a variety of diseases mediated by CB2 receptor activity, including inflammatory pain, reflex sympathetic dystrophy/causalgia, peripheral neuropathy, entrapment neuropathy, complex regional pain syndrome, nociceptive pain, neuropathic pain, fibromyalgia, chronic low back pain, visceral pain, acute cerebral ischemia, pain, chronic pain, acute pain, post herpetic neuralgia (PHN), neuropathies, neuralgia, diabetic neuropathy, HIV-related neuropathy, nerve injury, ocular pain, headaches of various etiologies, including migraine, acute herpes zoster (shingles), pain-related disorders such as tactile allodynia and hyperalgesia, rheumatoid arthritic pain, osteoarthritic pain, back pain, cancer pain, dental pain, muscular pain, mastalgia, pain resulting from dermal injuries, fibromyalgia, neuritis, sciatica, inflammation, neurodegenerative disease, cough, broncho constriction, irritable bowel syndrome (IBS), inflammatory bowel disease (IBD), colitis, cerebrovascular ischemia, emesis such as cancer chemotherapy-induced emesis, rheumatoid arthritis, Crohn's disease, ulcerative colitis, asthma, dermatitis, seasonal allergic rhinitis, gastroesophageal reflux disease (GERD), constipation, diarrhea, functional gastrointestinal disorders, irritable bowel syndrome, cutaneous T cell lymphoma, multiple sclerosis, osteoarthritis, psoriasis, systemic lupus erythematosus, diabetes, glaucoma, osteoporosis, glomerulonephritis, renal ischemia, nephritis, hepatitis, cerebral stroke, vasculitis, myocardial infarction, cerebral ischemia, reversible airway obstruction, adult respiratory disease syndrome, chronic obstructive pulmonary disease (COPD), cryptogenic fibrosing alveolitis, and bronchitis.

Aspects of the present specification relate to a compound of formula I:

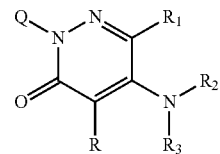

wherein R, $R_1$, $R_2$, and $R_3$, are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and Q is aryl, a substituted aryl, or the ring-structure of formula II:

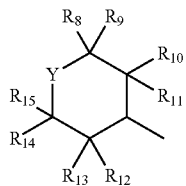

wherein Y is N, O, S or C($R_6R_7$); and $R_6$, $R_7$, $R_8$, $R_9$, $R_{10}$, $R_{11}$, $R_{12}$, $R_{13}$, $R_{14}$, and $R_{15}$ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl.

In other aspects, the present specification relate to a compound of formula I:

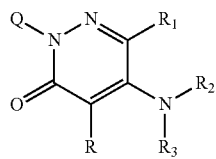

wherein R is H, halogen, hydroxyl, oxo, keto, $C_1$-$C_6$ alkyl, or $OC_1$-$C_6$ alkyl;

$R_1$ is H, halogen, hydroxyl, oxo, keto, $C_1$-$C_6$ alkyl, or $OC_1$-$C_6$ alkyl;

$R_2$ is H, halogen, hydroxyl, oxo, keto, $C_1$-$C_6$ alkyl, $OC_1$-$C_6$ alkyl, or $C_2$-$C_6$ alkyl substituted by N($R_4R_5$), or $C_2$-$C_6$ alkyl substituted by OH;

$R_3$ is H, halogen, hydroxyl, oxo, keto, $C_1$-$C_6$ alkyl, or $OC_1$-$C_6$ alkyl;

$R_4$ and $R_5$ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and Q is phenyl, a substituted phenyl, or the ring-structure of formula II:

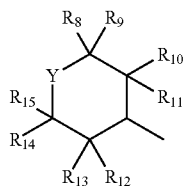

wherein Y is O or C($R_6R_7$); and $R_6$, $R_7$ $R_8$, $R_9$, $R_{10}$, $R_{11}$, $R_{12}$, $R_{13}$, $R_{14}$, and $R_{15}$ are independently H, hydroxyl, halogen, oxo, keto, $C_1$-$C_6$ alkyl, or $OC_1$-$C_6$ alkyl.

In yet other aspects, the present specification relate to a compound of formula I:

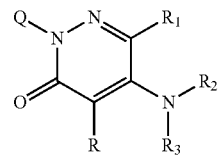

wherein R is H, halogen, hydroxyl, oxo, keto, $C_1$-$C_3$ alkyl, or $OC_1$-$C_3$ alkyl;

$R_1$ is H, halogen, $C_1$-$C_3$ alkyl, or $OC_1$-$C_3$ alkyl;

$R_2$ is $C_1$-$C_6$ alkyl, $C_2$-$C_6$ alkyl substituted by N($R_4R_5$), or $C_2$-$C_6$ alkyl substituted by OH;

$R_3$ is H, or $C_1$-$C_6$ alkyl;

$R_4$ and $R_5$ are independently $C_1$-$C_4$ alkyl, morpholine, or piperidine; and Q is the ring-structure of formula II:

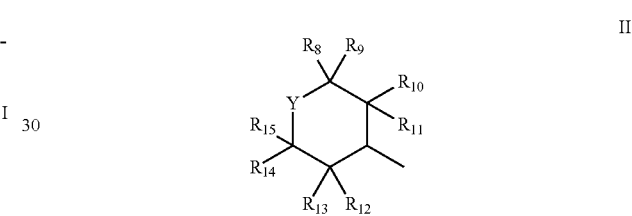

wherein Y is O or C($R_6R_7$);

$R_6$ and $R_7$ are independently H or halogen; and $R_8$, $R_9$, $R_{10}$, $R_{11}$, $R_{12}$, $R_{13}$, $R_{14}$, and $R_{15}$ are independently H or $C_1$-$C_2$ alkyl, provided at least two are not hydrogen.

In a further aspect, the compound is of formula I wherein $R_8$, $R_9$, $R_{14}$, and $R_{15}$ are methyl; $R_{10}$, $R_{11}$, $R_{12}$, and $R_{13}$ are hydrogen; and Y is $CH_2$. In yet further aspects, the compound is 5-hydroxy-2-(3,3,5,5-tetramethylcyclohexyl)pyridazin-3-one, 4,5-Dichloro-2-(3,3,5,5-tetramethylcyclohexyl)pyridazin-3-one, 4-Chloro-5-methylamino-2-(3,3,5,5-tetramethylcyclohexyl)pyridazin-3-one, 4-Chloro-5-dimethylamino-2-(3,3,5,5-tetramethylcyclohexyl)pyridazin-3-one, 4-Chloro-5-propylamino-2-(3,3,5,5-tetramethylcyclohexyl)pyridazin-3-one, 5-Methylamino-2-(3,3,5,5-tetramethylcyclohexyl)pyridazin-3-one, 5-Dimethylamino-2-(3,3,5,5-tetramethylcyclohexyl)pyridazin-3-one, 5-Propylamino-2-(3,3,5,5-tetramethylcyclohexyl)pyridazin-3-one, 5-Propyloxy-2-(3,3,5,5-tetramethylcyclohexyl)pyridazin-3-one, 4-Chloro-5-(2-morpholin-4-ylethylamino)-2-(3,3,5,5-tetramethylcyclohexyl)pyridazin-3-one, 4-Chloro-5-(2-dimethylaminoethylamino)-2-(3,3,5,5-tetramethylcyclohexyl)pyridazin-3-one, 4-Bromo-5-propylamino-2-(3,3,5,5-tetramethylcyclohexyl)pyridazin-3-one, 4-Bromo-5-(2-dimethylaminoethylamino)-2-(3,3,5,5-tetramethylcyclohexyl)pyridazin-3-one, 4-Bromo-5-(2-morpholin-4-ylethylamino)-2-(3,3,5,5-tetramethylcyclohexyl)pyridazin-3-one, 4-Chloro-5-(2-dimethylamino ethylmethylamino)-2-(3,3,5,5-tetramethylcyclohexyl)pyridazin-3-one, or 4-Chloro-5-(2-diethylaminoethylamino)-2-(3,3,5,5-tetramethylcyclohexyl)pyridazin-3-one.

In other aspects of the present specification relate to a compound of formula III:

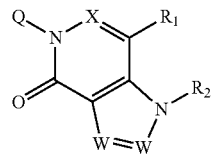

wherein X is N, O, S or C(R₄R₅)
W is N, O, S, or CH;
R₁ and R₂ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl;
R₄ and R₅ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and
Q is phenyl, a substituted phenyl, or the ring-structure of formula II:

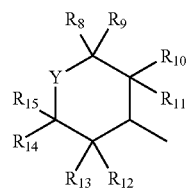

wherein Y is N, O, S or C(R₆R₇); and
R₆, R₇ R₈, R₉, R₁₀, R₁₁, R₁₂, R₁₃, R₁₄, and R₁₅ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl.

In yet other aspects of the present specification relate to a compound of formula III:

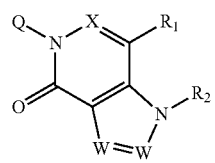

wherein X is N or CH;
W is N or CH;
R₁ is H, hydroxyl, halogen, oxo, keto, C₁-C₆ alkyl, or OC₁-C₆ alkyl;

R₂ is H, halogen, hydroxyl, oxo, keto, C₁-C₆ alkyl, OC₁-C₆ alkyl, C₂-C₆ alkyl substituted by N(R₄R₅), or CC₂-C₆ alkyl substituted by OH;
R₄ and R₅ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and
Q is phenyl, a substituted phenyl, or the ring-structure of formula II:

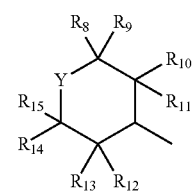

wherein Y is O or C(R₆R₇); and
R₆, R₇ R₈, R₉, R₁₀, R₁₁, R₁₂, R₁₃, R₁₄, and R₁₅ are independently H, hydroxyl, halogen, oxo, keto, C₁-C₆ alkyl, or OC₁-C₆ alkyl.

In yet other aspects of the present specification relate to a compound of formula III:

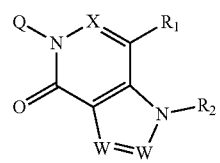

wherein R is H, halogen, C₁-C₃ alkyl, or OC₁-C₃ alkyl;
R₁ is H, halogen, C₁-C₃ alkyl, or OC₁-C₃ alkyl;
R₂ is C₁-C₆ alkyl, C₂-C₆ alkyl substituted by N(R₄R₅), or C₂-C₆ alkyl substituted by OH;
R₄ and R₅ are independently C₁-C₄ alkyl, morpholine, or piperidine;
X is N or CH;
W is N or CH; and
Q is the ring-structure of formula II:

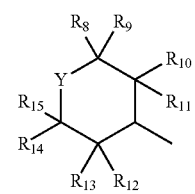

wherein Y is O or C(R₆R₇);
R₆ and R₇ are independently H or halogen; and
R₈, R₉, R₁₀, R₁₁, R₁₂, R₁₃, R₁₄, and R₁₅ are independently H or C₁-C₂ alkyl, provided at least two are not hydrogen.
In a further aspect of this composition, the compound is of formula III wherein R₈, R₉, R₁₄, and R₁₅ are methyl; R₁₀, R₁₁, R₁₂, and R₁₃ are hydrogen; and Y is CH₂. In yet further aspects of this composition, the compound is 1-Propyl-5-(3,3,5,5-tetramethyl cyclohexyl)pyrazolo[3,4-d]pyridazin-4-one, 2-Propyl-5-(3,3,5,5-tetramethyl cyclohexyl)pyrazolo[3,4-d]pyridazin-4-one, 1-(2-Morpholin-4-ylethyl)-5-(3,3,5,5-tetramethylcyclohexyl)pyrazolo[3,4-d]pyridazin-4-one, 2-(2-Morpholin-4-ylethyl)-5-(3,3,5,5-tetramethylcyclohexyl)pyrazolo[3,4-d]pyridazin-4-one, 1-(2-Dimethylaminoethyl)-5-(3,3,5,5-tetramethylcyclohexyl)pyrazolo[3,4-d]pyridazin-4-one, or 2-(2-Dimethylaminoethyl)-5-(3,3,5,5-tetramethylcyclohexyl)pyrazolo[3,4-d]pyridazin-4-one.

Other aspects of the present specification relate to compositions comprising a compound of formula I or a compound of formula III. In a further aspect of this composition, the composition is a pharmaceutical composition comprising a therapeutically effective amount of a compound of formula I, in admixture with a non-toxic, pharmaceutically acceptable vehicle. In a yet further aspect of this composition, the composition is a pharmaceutical composition comprising a therapeutically effective amount of a compound of formula III, in admixture with a non-toxic, pharmaceutically acceptable vehicle.

Yet other aspects of the present specification relate to methods of treating an individual suffering from a disease, the method comprising the step of administering to the individual a pharmaceutical composition comprising a therapeutically effective amount of a compound of formula I, wherein such administration reduces or eliminates a symptom associated with the disease.

Yet other aspects of the present specification relate to methods of treating an individual suffering from a disease, the method comprising the step of administering to the individual a pharmaceutical composition comprising a therapeutically effective amount of a compound of formula III, wherein such administration reduces or eliminates a symptom associated with the disease.

DETAILED DESCRIPTION

In all of the above formulae, as well as in those provided hereinafter, the straight lines represent bonds. Where there is no symbol for the atoms between the bonds, the appropriate carbon-containing radical is to be inferred.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When ranges of values are disclosed, and the notation "from $n_1$ ... to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.). When n is set at 0 in the context of "0 carbon atoms", it is intended to indicate a bond or null.

As used herein, either alone or in combination, the term "aryl" or "aryl hydrocarbon" refers to a functional group comprising a substituted or unsubstituted aromatic hydrocarbon with a conjugated cyclic molecular ring structure of 3 to 12 carbon atoms. An aryl group can be monocyclic, bicyclic or polycyclic, and may optionally include one to three additional ring structures, such as, e.g., a cycloalkyl, a cycloalkenyl, a heterocycloalkyl, a heterocycloalkenyl, or a heteroaryl. The term "aryl" includes, without limitation, phenyl (benzenyl), thiophenyl, indolyl, naphthyl, totyl, xylyl, anthracenyl, phenanthryl, azulenyl, biphenyl, naphthalenyl, 1-mMethylnaphthalenyl, acenaphthenyl, acenaphthylenyl, anthracenyl, fluorenyl, phenalenyl, phenanthrenyl, benzo[a]anthracenyl, benzo[c]phenanthrenyl, chrysenyl, fluoranthenyl, pyrenyl, tetracenyl (naphthacenyl), triphenylenyl, anthanthrenyl, benzopyrenyl, benzo[a]pyrenyl, benzo[e]fluoranthenyl, benzo[ghi]perylenyl, benzo[j]fluoranthenyl, benzo[k]fluoranthenyl, corannulenyl, coronenyl, dicoronylenyl, helicenyl, heptacenyl, hexacenyl, ovalenyl, pentacenyl, picenyl, perylenyl, and tetraphenylenyl.

As used herein, either alone or in combination, the term "lower aryl" refers to a functional group comprising a substituted or unsubstituted aromatic hydrocarbon with a conjugated cyclic molecular ring structure of 3 to 6 carbon atoms. Examples of lower aryl groups include, without limitation, phenyl and naphthyl.

As used herein, either alone or in combination, the term "alkenyl" refers to a functional group comprising a straight-chain or branched-chain hydrocarbon containing from 2 to 20 carbon atoms and having one or more carbon-carbon double bonds and not having any cyclic structure. An alkenyl group may be optionally substituted as defined herein. Examples of alkenyl groups include, without limitation, ethenyl, propenyl, 2-methylpropenyl, butenyl, 1,4-butadienyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, and the like.

As used herein, either alone or in combination, the term "alkyl" refers to a functional group comprising a straight-chain or branched-chain hydrocarbon containing from 1 to 20 carbon atoms linked exclusively by single bonds and not having any cyclic structure. An alkyl group may be optionally substituted as defined herein. Examples of alkyl groups includes, without limitation methyl, ethyl, n-propyl, isopropyl, n-butyl, isobutyl, sec-butyl, tert-butyl, pentyl, iso-amyl, hexyl, heptyl, octyl, noyl, decyl, undecyl, dodecyl tridecyl, tetradecyl, pentadecyl, hexadecyl, heptadecyl, octadecyl, nonadecyl, eicosyl, and the like.

As used herein, either alone or in combination, the term "alkynyl" refers to a functional group comprising a straight-chain or branched-chain hydrocarbon containing from 2 to 20 carbon atoms and having one or more carbon-carbon triple bonds and not having any cyclic structure. An alkynyl group may be optionally substituted as defined herein. Examples of alkynyl groups include, without limitation, ethynyl, propynyl, hydroxypropynyl, butynyl, butyn-1-yl, butyn-2-yl, 3-methylbutyn-1-yl, pentynyl, pentyn-1-yl, hexynyl, hexyn-2-yl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, and the like.

As used herein, either alone or in combination, the term "cycloalkenyl" and "cycloolefin" refers to a functional group comprising a substituted or unsubstituted non-aromatic hydrocarbon with a non-conjugated cyclic molecular ring structure of 3 to 12 carbon atoms having at least one carbon-carbon double bond in the carbon ring structure. A cycloalkenyl group can be monocyclic, bicyclic or polycyclic, and may optionally include one to three additional ring structures, such as, e.g., an aryl, a heteroaryl, a cycloalkyl, a heterocycloalkyl, or a heterocycloalkenyl. Examples of such cycloalkenyl groups include, without limitation, cyclopropene, cyclobutene, 1,3-cyclobutadiene, cyclopentene, 1,3-cyclopentadiene, cyclohexene, 1,3-cyclohexadiene, 1,4-cyclohexadiene, cycloheptene. 1,3-cycloheptadiene, 1,4-cycloheptadiene, and 1,5-cycloheptadiene.

As used herein, either alone or in combination, the term "lower cycloalkenyl" refers to a functional group comprising a monocyclic substituted or unsubstituted non-aromatic hydrocarbon with a non-conjugated cyclic molecular ring structure of 3 to 6 carbon atoms having at least one carbon-carbon double bond in the carbon ring structure.

As used herein, either alone or in combination, the term "cycloalkyl", "carbocyclicalkyl", and "carbocyclealkyl" refers to a functional group comprising a substituted or unsubstituted non-aromatic hydrocarbon with a non-conjugated cyclic molecular ring structure of 3 to 12 carbon atoms linked exclusively with carbon-carbon single bonds in the carbon ring structure. A cycloalkyl group can be monocyclic, bicyclic or polycyclic, and may optionally include one to three additional ring structures, such as, e.g., an aryl, a heteroaryl, a cycloalkenyl, a heterocycloalkyl, or a heterocycloalkenyl.

As used herein, either alone or in combination, the term "lower cycloalkyl" refers to a functional group comprising a monocyclic substituted or unsubstituted non-aromatic hydrocarbon with a non-conjugated cyclic molecular ring structure of 3 to 6 carbon atoms linked exclusively with carbon-carbon single bonds in the carbon ring structure. Examples of lower cycloalkyl groups include, without limitation, cyclopropyl, cyclobutyl, cyclopentyl, and cyclohexyl.

As used herein, either alone or in combination, the term "diene" refers to a functional group comprising a straight-chain or branched-chain hydrocarbon with two carbon-carbon double bonds and having the general formula of $C_nH2_{n-2}$. A diene can be unconjugated, conjugated or cumulative. Examples of diene groups include, without limitation, allene (propan-1,2-diene), 1,3-butadiene, chloroprene, hexachlorobutadiene, isoprene (2-methyl-1,3-butadiene), isotoluene, myrcenol, and piperylene.

As used herein, either alone or in combination, the term "cyclodiene" refers to a functional group comprising a substituted or unsubstituted non-aromatic hydrocarbon with a cyclic molecular ring structure of 3 to 12 carbon atoms and having two carbon-carbon double bonds in the carbon ring structure. A cyclodiene can be unconjugated, conjugated or cumulative. Examples of cyclodiene groups include, without limitation, cyclopentadiene, 1,5-cyclooctadiene, hexachlorocyclopentadiene, and methylcyclopentadiene.

As used herein, the term "functional group" refers to a specific group of atoms within a molecule that are responsible for the characteristic chemical reactions of those molecules.

As used herein, either alone or in combination, the term "halo" or "halogen" refers to the nonmetal elements fluorine (F), chlorine (Cl), bromine (Br), iodine (I), astatine (At) and ununseptium (Uus).

As used herein, either alone or in combination, the term "heteroalkyl" refers to a functional group comprising a straight-chain or branched-chain hydrocarbon containing from 1 to 20 atoms linked exclusively by single bonds, where at least one atom in the chain is a carbon and at least one atom in the chain is O, S, N, or any combination thereof. The heteroalkyl group can be fully saturated or contain from 1 to 3 degrees of unsaturation. The non-carbon atoms can be at any interior position of the heteroalkyl group, and up to two non-carbon atoms may be consecutive, such as, e.g., —CH$_2$—NH—OCH$_3$. In addition, the non-carbon atoms may optionally be oxidized and the nitrogen may optionally be quaternized.

As used herein, either alone or in combination, the term "heteroaryl" refers to a functional group comprising a substituted or unsubstituted aromatic hydrocarbon with a conjugated cyclic molecular ring structure of 3 to 12 atoms, where at least one atom in the ring structure is a carbon and at least one atom in the ring structure is O, S, N, or any combination thereof. A heteroaryl group can be monocyclic, bicyclic or polycyclic, and may optionally include one to three additional ring structures, such as, e.g., an aryl, a cycloalkyl, a cycloalkenyl, a heterocycloalkyl, or a heterocycloalkenyl. Examples of heteroaryl groups include, without limitation, acridinyl, benzidolyl, benzimidazolyl, benzisoxazolyl, benzodioxinyl, dihydrobenzodioxinyl, benzodioxolyl, 1,3-benzodioxolyl, benzofuryl, benzoisoxazolyl, benzopyranyl, benzothiophenyl, benzo[c]thiophenyl, benzotriazolyl, benzoxadiazolyl, benzoxazolyl, benzothiadiazolyl, benzothiazolyl, benzothienyl, carbazolyl, chromonyl, cinnolinyl, dihydrocinnolinyl, coumarinyl, dibenzofuranyl, furopyridinyl, furyl, indolizinyl, indolyl, dihydroindolyl, imidazolyl, indazolyl, isobenzofuryl, isoindolyl, isoindolinyl, dihydroisoindolyl, isoquinolyl, dihydroisoquinolinyl, isoxazolyl, isothiazolyl, oxazolyl, oxadiazolyl, phenanthrolinyl, phenanthridinyl, purinyl, pyranyl, pyrazinyl, pyrazolyl, pyridyl, pyrimidinyl, pyridazinyl, pyrrolinyl, pyrrolyl, pyrrolopyridinyl, quinolyl, quinoxalinyl, quinazolinyl, tetrahydroquinolinyl, tetrazolopyridazinyl, tetrahydroisoquinolinyl, thiophenyl, thiazolyl, thiadiazolyl, thienopyridinyl, thienyl, thiophenyl, triazolyl, xanthenyl, and the like.

As used herein, either alone or in combination, the term "lower heteroaryl" refers to a functional group comprising a monocyclic or bycyclic, substituted or unsubstituted aromatic hydrocarbon with a conjugated cyclic molecular ring structure of 3 to 6 atoms, where at least one atom in the ring structure is a carbon and at least one atom in the ring structure is O, S, N, or any combination thereof.

As used herein, either alone or in combination, the term "heterocycloalkenyl" refers to a functional group comprising a substituted or unsubstituted non-aromatic hydrocarbon with a non-conjugated cyclic molecular ring structure of 3 to 12 atoms having at least one double bond, where at least one atom in the ring structure is a carbon and at least one atom in the ring structure is O, S, N, or any combination thereof. The heterocycloalkenyl group can be unsaturated, fully saturated or contain from 1 to 3 degrees of unsaturation. A heterocycloalkenyl group can be monocyclic, bicyclic or polycyclic, and may optionally include one to three additional ring structures, such as, e.g., an aryl, a heteroaryl, a cycloalkyl, a heterocycloalkyl, or a cycloalkenyl.

As used herein, either alone or in combination, the term "lower heterocycloalkenyl" refers to a functional group comprising a monocyclic substituted or unsubstituted non-aromatic hydrocarbon with a non-conjugated cyclic molecular ring structure of 3 to 6 atoms having at least one double bond, where at least one atom in the ring structure is a carbon and at least one atom in the ring structure is O, S, N, or any combination thereof.

As used herein, either alone or in combination, the term "heterocycloalkyl", "heterocyclicalkyl", and "heterocyclealkyl" refers to a functional group comprising a substituted or unsubstituted non-aromatic hydrocarbon with a non-conjugated cyclic molecular ring structure of 3 to 12 atoms linked exclusively with single bonds in the ring structure, where at least one atom in the ring structure is a carbon and at least one atom in the ring structure is O, S, N, or any combination thereof. The heterocycloalkyl group can be unsaturated, fully saturated or contain from 1 to 3 degrees of unsaturation. A heterocycloalkyl group can be monocyclic, bicyclic or polycyclic, and may optionally include one to three additional ring structures, such as, e.g., an aryl, a heteroaryl a cycloalkyl, a cycloalkenyl, or a heterocycloalkenyl. A heterocycle group may be optionally substituted unless specifically prohibited. Examples of such heterocycloalkyl groups include, without limitation, ariridinyl, azirinyl, diazirinyl, oxiranyl, oxirenyl, dioxiranyl, thiiranyl, thiirenyl, azetidinyl, azetyl, diazetidinyl, oxetanyl, oxetyl, dioxetanyl, dioxetenyl, thietanyl, thietyl, dithietanyl, dithietyl, pyrrolidinyl, pyrrolinyl, pyrrolyl, furanyl, dihydrofuranyl, tetrahydrofuranyl, tetrahydrothiophenyl, dihydrothiophenyl, thiophenyl, imidazolidinyl, pyrazolidinyl, imidazolyl, imidazolinyl, pyrazolyl, pyrazolinyl, oxazolidinyl, isoxazolidinyl, oxazolyl, oxazolinyl, isoxazolyl, isoxazolinyl, thiazolidinyl, isothiazolidinyl, thiazolyl, thiazolinyl, isothiazolyl, isothiazolinyl, dioxolanyl, 1,3-dioxanyl, 1,4-dioxanyl, dioxolanyl, 1,3-dioxolanyl, oxathiolanyl, dithiolanyl, triazolyl, dithiazolyl, furazanyl, oxadiazolyl, thiadiazolyl, tetrazolyl, piperidinyl, tetrahydropyridinyl, pyridinyl, dihydropyridinyl, dihydro[1,3]oxazolo[4,5-b]pyridinyl, pyranyl, tetrahydropyranyl, thianyl, thiopyranyl, piperazinyl, diazinyl, morpholinyl, thiomorpholinyl, oxazinyl, thiazinyl, dithianyl, dioxanyl, dioxinyl, triazinyl, trioxanyl, tetrazinyl, azepanyl, azepinyl, oxepanyl, oxepinyl, thiepanyl, thiepinyl, diazepinyl, thiazepinyl, azocanyl, azocinyl, oxecanyl, thiocanyl, and the like.

As used herein, either alone or in combination, the term "lower heterocycloalkyl" refers to a functional group comprising a monocyclic substituted or unsubstituted non-aromatic hydrocarbon with a non-conjugated cyclic molecular ring structure of 3 to 6 atoms linked exclusively with single bonds in the ring structure, where at least one atom in the ring structure is a carbon and at least one atom in the ring structure is O, S, N, or any combination thereof. Lower heterocycloalkyls may be unsaturated. Examples of lower heterocycloalkyls include, without limitation, pyrrolidinyl, imidazolidinyl, pyrazolidinyl, piperidinyl, piperazinyl, and morpholinyl.

As used herein, either alone or in combination, the term "hydroxy" refers to the functional group hydroxyl (—OH).

As used herein, either alone or in combination, the term "imidate" or "imino ether" refers to a molecule comprising an imine (C=N—) and having the general formula RN=C(OR')R", wherein R, R' and R" are an organic moiety or group.

As used herein, either alone or in combination, the term "imide" refers to a functional group comprising two carbonyl groups bound to nitrogen [—C(=O)NC(=O)—], and having the general formula RCONCOR', wherein R and R' are an organic moiety or group.

As used herein, either alone or in combination, the term "imine" refers to the functional group —C=NH—. A primary ketimine has the general formula RCNHR', a secondary ketimine has the general formula RCNR'R", a primary aldimine has the general formula RCNHH, and a secondary aldimine has the general formula RCNR'H, wherein R, R" and R" are an organic moiety or group.

As used herein, either alone or in combination, the term "imino" refers to the functional group =NH—.

As used herein, either alone or in combination, the term "iminohydroxy" refers to the functional group =N(OH) and its corresponding anion =N—O—.

As used herein, the term "parent chain", "parent hydrocarbon chain", or "in the main chain" refers to the longest contiguous or adjacent chain of carbon atoms starting at the point of attachment of a group to the molecules of any one of the formulas disclosed herein.

As used herein, either alone or in combination, the term "isocyanato" or "isonitrile" refers to the functional group —NCO.

As used herein, either alone or in combination, the term "isothiocyanato" refers to the functional group —NCS.

As used herein, either alone or in combination, the term "isocyanate" refers to the functional group —N=C=O.

As used herein, either alone or in combination, the term "isocyanide" refers to the functional group —N≡C, and having the general formula RCN, wherein R is an organic moiety or group.

As used herein, either alone or in combination, the term "isothiocyanate" refers to the functional group —N=C=S.

As used herein, either alone or in combination, the term "keto" refers to the functional group —C=O.

As used herein, either alone or in combination, the term "ketone" refers to a molecule comprising a keto group [—C=O], and having the general formula RCOR', wherein R and R' are an organic moiety or group.

As used herein, the term "linear chain of atoms" refers to the longest straight chain of atoms independently selected from carbon, nitrogen, oxygen and sulfur.

As used herein, either alone or in combination, the term "lower" refers to a functional group or molecule containing from 1 to 6 carbon atoms, unless otherwise specifically defined.

As used herein, either alone or in combination, the term "nitrile" refers to a molecule comparing a cyano group (—C≡N), and having the general formula RCN, wherein R is an organic moiety or group.

As used herein, either alone or in combination, the term "nitrite" refers to the functional group —NO2-, and having the general formula $RNO_2^-$, wherein R is an organic moiety or group.

As used herein, either alone or in combination, the term "nitroso" refers to the functional group —N=O, and having the general formula RNO, wherein R is an organic moiety or group.

As used herein, either alone or in combination, the term "nitro" refers to the functional group —NO2, and having the general formula $RNO_2^-$, wherein R is an organic moiety or group.

As used herein, either alone or in combination, the term "nitrate" refers to the functional group —NO3-, and having the general formula $RNO_3$—, wherein R is an organic moiety or group.

As used herein, either alone or in combination, the term "null," refers to a functional group that is absent.

As used herein, either alone or in combination, the term "oxo" refers to the functional group =O.

As used herein, either alone or in combination, the term "oxy" or "oxa" refer to the functional group —O—.

As used herein, either alone or in combination, the term "oxyalkyl" refers to a functional group comprising an alkyl group attached to the parent molecular moiety through an oxy group.

As used herein, either alone or in combination, the term "oxime" refers to a molecule comprising an imine group (C=N) and having the general formula RR'C=NOH, wherein R and R' are organic radicals. An oxime where R or R' is a hydrogen is oximine is called an aldoxime, whereas when both R and R' are not hydrogens, the oxime is called a ketooxime.

As used herein, either alone or in combination, the term "thio" and "thia" refer to a functional group having an oxygen atom being replaced by a sulfur atom in the parent molecular moiety. The terms thia and thio include a sulfanyl group as well as oxidized derivatives of a sulfanyl group, such as, e.g., a sulfinyl group and a sulfonyl group.

As used herein, either alone or in combination, the term "thioalkyl" refers to a functional group comprising an alkyl group attached to the parent molecular moiety through a thio group.

As used herein, either alone or in combination, the term "unsubstituted" refers to a functional group or molecule that has hydrogen atoms at every position on the parent chain of a hydrocarbon (e.g., —CH$_2$CH$_3$).

As used herein, the term "substituted" refers to a functional group or molecule that has at least one substituent replacing a hydrogen atom at a position on the parent chain of a hydrocarbon. A substituted group may be fully substituted (e.g., —CF$_2$CF$_3$), monosubstituted (e.g., —CH$_2$CH$_2$F) or substituted at a level anywhere in between fully substituted and monosubstituted (e.g., —CH$_2$CH$_2$F, —CHFCH$_2$F, —CH$_2$CHF$_2$, —CHFCHF$_2$).

As used herein, the term "substituent" refers to an atom or group of atoms substituted in place of a hydrogen atom on the parent chain of a hydrocarbon. Where substituents are recited without qualification as to substitution, both substituted and unsubstituted forms are encompassed. Examples of substituents include, without limitation, acetyl, acyl, acylamino, acyl halide, alkenyl, alkoxy, alkyl, alkylamino, alkylcarbonyl, alkyloxy, alkyloxo, alkylthio, alkynyl, amidine, amido, amino, aryl, arylamino, arylalkenyl, arylalkoxy, arylalkyl, arylalkynyl, arylalkanoyl, aryloxy, arylthio, azide, azo, benzo, carbamyl, carbonyl, carboxyl, carboxamide, carboxamidine, cyanate, cyano, cycloalkenyl, cycloalkyl, diene, cyclodiene, disulfanyl, enone, halide, halogen, haloalkenyl, haloalkoxy, haloalkyl, heteroalkyl, heteroaryl, heterocycloalkenyl, heterocycloalkyl, hydrazinyl, hydrogen, hydroperoxide, hydroxy, hydroxyalkyl, imide, imine, imino, iminohydroxy, isocyanato, isothiocyanato, isocyanate, isocyanide, isothiocyanate, keto, mercaptyl, nitrite, nitroso, nitro, nitrate, oxo, oxy, oxoalkyl, oxyalkyl, oxime, perhaloalkoxy, perhaloalkyl, peroxy, sulfanyl, sulfhydryl, sulfinyl, sulfonyl, sulfyl, sulfonamido, thioalkyl, thiocarbony, thiocarbamyl, thiocyanate, isothiocyanate, thiocyanato, thioketo, trihalomethanesulfonamido, trihalomethoxy, and all lower forms therein.

As used herein, the term "optionally substituted" refers to a functional group or molecule that may be either substituted or unsubstituted. Different sets of optional substituents to a particular moiety may be defined as needed; in these cases, the optional substitution will be as defined, often immediately following the phrase, "optionally substituted with." An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in between fully substituted and monosubstituted (e.g., —CH$_2$CH$_2$F, —CHFCH$_2$F, —CH$_2$CHF$_2$, —CHFCHF$_2$).

Aspects of the present specification disclose, in part, a cannabinoid-2 agonist. As used herein, the term "cannabinoid-2 receptor agonist" is synonymous with "cannabinoid-2 agonist," "CB2 receptor agonist," and "CB2 agonist" and refers to a molecule that binds to a specific receptor and triggers a cellular response that mimics the action of the endogenous ligand. An agonist can elicit a maximal response following receptor binding and activation (full agonist), or can elicit a submaximal response following receptor binding and activation (partial agonist). The term "cannabinoid-2 agonist" includes an isomer, like a geometric isomer or stereoisomer, such as, e.g., an enantiomer or diastereomer; a salt, an ester, a prodrug, metabolite, or a solvate of the cannabinoid-2 inverse-agonists disclosed in the present specification. The compounds of formula (I) or formula (III) are cannabinoid-2 agonists.

Aspects of the present specification disclose, in part, a cannabinoid-2 inverse-agonist. As used herein, the term "cannabinoid-2 receptor inverse-agonist" is synonymous with cannabinoid-2 inverse-agonist," "CB2 receptor inverse-agonist" and CB2 inverse-agonist" and refers to a molecule that binds to a specific receptor and triggers a cellular response that produces the opposite action of the endogenous ligand, i.e., an inverse-agonist produces an effect opposite to that of an agonist. An inverse agonist can elicit a maximal opposite response following receptor binding (full inverse agonist), or can elicit a submaximal opposite response following receptor binding (partial inverse agonist). The term "cannabinoid-2 inverse-agonist" includes an isomer, like a geometric isomer or stereoisomer, such as, e.g., an enantiomer or diastereomer; a salt, an ester, a prodrug, metabolite, or a solvate of the cannabinoid-2 inverse-agonists disclosed in the present specification.

As used herein, the term "compound," "compounds," "compound disclosed in the present specification," or "compounds disclosed in the present specification" refers, unless indicated otherwise, to a compound of formula (I) or formula (III) as hereinbefore defined, polymorphs, prodrugs, and isomers thereof (including optical, geometric and tautomeric isomers) as hereinafter defined and isotopically-labeled compounds of formula (I) or formula (III). As sued herein, all references to a compound of formula (I) or a compound of formula (III) include references to salts and complexes thereof and to solvates and complexes of salts thereof.

The compounds disclosed in the present specification can be tested for CB2 receptor agonist activity or CB2 receptor inverse-agonist activity using a wide variety on known methods. For example, binding assays can be used to assess whether a compound disclosed in the present specification can bind to a CB1 receptor and/or CB2 receptor in order to determine selectivity for a CB2 receptor. Such binding assays are described in, e.g., Meyyappan Muthuppalaniappan, et al., Novel Cannabinoid Receptor Ligands, Pharmaceutical Compositions Containing Them, and Processes for Their Preparation, U.S. Patent Publication 2008/0200501; Timothy C. Gahman, et al., Heterocyclodiazeoine Cannabinoid Receptor Modulators for Treatment of Disease, U.S. Patent Publication 2009/0062253; Tomoki Kato, et al., Sulfonyl Benzimidazole Derivatives, U.S. Patent Publication 2009/0137584; Fina Liotta, et al., Hexahydro-Cycloheptapyrazole Cannabinoid Modulators, US Patent Publication 2009/0197886; Mingde Xia, et al., Method for Treating CB2 Receptor Mediated Pain, U.S. Patent Publication 2009/0215850; and Doria Riether, et al., Compounds which Modulate the CB2 Receptor, U.S. Patent Publication 2009/0275611; each of which is hereby incorporated by reference in its entirety.

As another example, activity assays can be used to assess whether a compound disclosed in the present specification can elicit an agonist or inverse-agonist response in order to determine whether the compound is a CB2 agonist or a CB2 inverse-agonist. Such activity assays are described in, e.g., Andrew J. Eatherton, et al., Imidazopyridine Derivitives as Cannabinoid Receptor Ligands, U.S. Patent Publication 2008/0221097; Fina Liotta, et al., Hexahydro-Cycloheptapyrazole Cannabinoid Modulators, US Patent Publication 2009/0197886; Mingde Xia, et al., Method for Treating CB2 Receptor Mediated Pain, U.S. Patent Publication 2009/0215850; and Doria Riether, et al., Compounds which Modulate the CB2 Receptor, U.S. Patent Publication 2009/0275611; each of which is hereby incorporated by reference in its entirety.

The compounds disclosed in the present specification may be present in the form of an isomer. As used herein, the term "isomer" refers to compounds disclosed in the present specification that has the same composition and molecular weight but differs in one or more physical and/or chemical properties. Such isomers have the same number and kind of atoms but differ in structure. The structural difference may be in constitution (geometric isomers), in an ability to rotate the plane of polarized light (stereoisomers), or in the position of a hydrogen atom or proton (tautomeric isomers). The compounds disclosed in the present specification can include compounds that form more than one type of isomerism, or mixtures of one or more thereof. Also included are acid addition salts wherein the counterion is optically active, for example, D-lactate or L-lysine, or racemic, for example, DL-tartrate or DL-arginine.

As used herein, the term "geometric isomer" refers to isomers that differs in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) or "chair" configuration, the substituents are on opposite sides in relationship to the carbon-carbon double bond. In the "Z" (same sided) or "boat" configuration, the substituents are oriented on the same side in relationship to the carbon-carbon double bond. Substituent atoms (other than H) attached to a carbocyclic ring may be in a cis or trans configuration. In the "cis" configuration, the substituents are on the same side in relationship to the plane of the ring. In the "trans" configuration, the substituents are on opposite sides in relationship to the plane of the ring. Compounds having a mixture of "cis" and "trans" species are designated "cis/trans." Substituent atoms (other than H) attached to a bridged bicyclic system may be in an "endo" or "exo" configuration. In the "endo" configuration, the substituents attached to a bridge (not a bridgehead) point toward the larger of the two remaining bridges; in the "exo" configuration, the substituents attached to a bridge point toward the smaller of the two remaining bridges.

As used herein, the term "stereoisomer" refers to isomers of identical constitution that differs in the arrangement of their atoms in space. Enantiomers, diastereomers and tautomers are stereoisomers wherein an asymmetrically substituted carbon atom acts as a chiral center. As sued herein, the term "chiral" refers to a molecule that is not superposable on its mirror image, implying the absence of an axis and a plane or center of symmetry. As used herein, the term "enantiomer" refers to one of a pair of molecular species that are mirror images of each other and are not superposable. As used herein, the term "diastereomer" refers to stereoisomers that are not related as mirror images. When a compound contains, e.g., a keto or oxime group or an aromatic moiety, tautomeric isomerism can occur. As used herein, the term "racemate" or "racemic mixture" refers to a compound of equimolar quantities of two enantiomeric species, wherein the compound is devoid of optical activity. As used herein, the term "optical activity" refers to the degree to which a chiral molecule or nonracemic mixture of chiral molecules rotates the plane of polarized light. The symbols "R" and "S" represent the configuration of substituents around a chiral carbon atom(s). The symbols "R*" and "S*" denote the relative configurations of substituents around a chiral carbon atom(s). The isomeric descriptors "R," "R*," "S," "S*," "E," "Z," "cis," "trans," "exo" and "endo" are used as described herein for indicating atom configuration(s) relative to a core molecule and are intended to be used as defined in the literature (IUPAC Recommendations for Fundamental Stereochemistry (Section E), Pure Appl. Chem., 1976, 45:13-30).

As used herein, the term "tautomeric isomer" refers to isomers of identical constitution that differs in the arrangement of a hydrogen atom (proton) or reversible anionotropic rearrangements. Tautomeric isomers are able to exist in equilibrium and react with each other, and as such, are mutually interconvertible, under normal conditions, forming a mixture that is in dynamic equilibration. In keto-enol tautomerism, the hydrogen atom bonded to the carbon atom in a carbonyl (keto) group (—CH—C=O) moves to the oxygen atom, making it an enol group (—C=C—OH). The keto form predominates in many aldehydes and ketones, the enol form in phenols. Sugars (e.g., glucose) exhibit tautomerism between open (chain) forms and closed (ring) forms.

It is to be understood that the various substituent geometric isomers, stereoisomers, tautomeric isomers, and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art. See Kato, et al., *Sulfonyl Benzimidazole Derivitives*, US Patent Publication 2009/0137584, which is hereby incorporated by reference in its entirety.

The compounds disclosed in the present specification may be present in the form of a pharmaceutically acceptable salt. As used herein, the term "a pharmaceutically acceptable salt" refers to non-toxic acidic/anionic or basic/cationic salt forms of the compounds disclosed in the present specification. Suitable pharmaceutically acceptable salts include acid addition salts which may, e.g., be formed by mixing a solution of the compound disclosed in the present specification with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore when the compounds disclosed in the present specification carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, without limitation, acetate, aspirate, benzenesulfonate, benzoate, besylate, bicarbonate, bisulfate, bitartrate, borate, bromide, calcium, camsylate (or camphorsulphonate), carbonate, chloride, citrate, clavulanate, dihydrochloride, edetate, edisylate, esylate, formate, fumarate, gluceptate, gluconate, glucuronate, glutamate, hexafluorophosphate, hibenzate, hydrabamine, hydrobromide, hydrobromine, hydrochloride, hydroiodide, iodide, isethionate, isothionate, lactate, malate, maleate, malonate, mandelate, mesylate, methylsulfate, nitrate, naphthylate, 2-napsylate, nicotinate, nitrate, oleate, orotate, oxalate, pamoate, palmitate, phosphate/diphosphate/hydrogen phosphate, saccharate, salicylate, stearate, sulfate, succinate, tartrate, tosylate and trifluoroacetate. See Handbook of Pharmaceutical Salts: Properties, Selection, and Use, by Stahl and Wermauth (Wiley-VCH, Weinberg, Germany, 2002).

The compounds disclosed in the present specification may be present in the form of an ester. An ester of any of the compounds disclosed in the present specification is formed by an alcohol and an organic or inorganic acid to form the corresponding ester and water.

The compounds disclosed in the present specification may be present in the form of a prodrugs or metabolite. In general, such prodrugs and metabolites will be functional derivatives of the compounds disclosed in the present specification that are readily convertible in vivo into an active compound. As used herein, the term "prodrug" refers a pharmaceutically acceptable form of a functional derivative of a compound disclosed in the present specification, wherein the prodrug may be: 1) a relatively active precursor which converts in vivo to an active prodrug component; 2) a relatively inactive precursor which converts in vivo to an active prodrug component; or 3) a relatively less active component of the compound that contributes to therapeutic biological activity after becoming available in vivo (i.e., as a metabolite). Conventional procedures for the selection and preparation of suitable prodrug derivatives are described in, for example, "Design of prodrugs", ed. H. Bundgaard, Elsevier, 1985. As used herein, the term "metabolite" refers to a pharmaceutically acceptable form of a metabolic derivative of a compound disclosed in the present specification, wherein the derivative is a relatively less active component of the compound that contributes to therapeutic biological activity after becoming available in vivo.

The compounds disclosed in the present specification may be present in the form of an unsolvated or solvated form. As used herein, the term 'solvate' refers to describe a molecular complex comprising a compound disclosed in the present specification and one or more pharmaceutically acceptable solvent molecules, for example, water, ethanol, DMSO, or other organic solvents. When a compound disclosed in the present specification forms a solvate with water, the term "hydrate" may be used instead of "solvent." Pharmaceutically acceptable solvates in accordance with the invention include hydrates and solvates wherein the solvent of crystallization may be isotopically substituted, e.g., $D_2O$, $d_6$-acetone, $d_6$-DMSO.

Furthermore, compounds of the present invention may have one or more polymorph or amorphous crystalline forms and as such are intended to be included in the scope of the invention. In addition, some of the compounds may form solvates with water (i.e., hydrates) or common organic solvents, and such are also intended to be encompassed within the scope of this invention.

In one embodiment, the present specification discloses the compounds of formula I and pharmaceutically acceptable forms thereof:

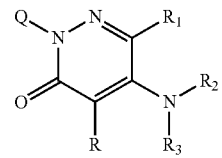

wherein R, $R_1$, $R_2$, and $R_3$, are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and Q is aryl, a substituted aryl, or the ring-structure of formula II:

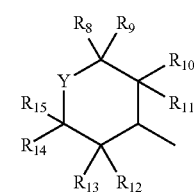

wherein Y is N, O, S or $C(R_6R_7)$; and
$R_6$, $R_7$, $R_8$, $R_9$, $R_{10}$, $R_{11}$, $R_{12}$, $R_{13}$, $R_{14}$, and $R_{15}$ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl.

In aspects of this embodiment, the present specification discloses the compounds of formula I and pharmaceutically acceptable forms thereof:

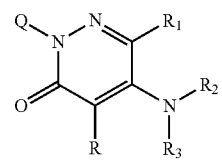

wherein R is H, halogen, hydroxyl, oxo, keto, $C_1$-$C_6$ alkyl, or $OC_1$-$C_6$ alkyl;
$R_1$ is H, halogen, hydroxyl, oxo, keto, $C_1$-$C_6$ alkyl, or $OC_1$-$C_6$ alkyl;
$R_2$ is H, halogen, hydroxyl, oxo, keto, $C_1$-$C_6$ alkyl, $OC_1$-$C_6$ alkyl, or $C_2$-$C_6$ alkyl substituted by $N(R_4R_5)$, or $C_2$-$C_6$ alkyl substituted by OH;
$R_3$ is H, halogen, hydroxyl, oxo, keto, $C_1$-$C_6$ alkyl, or $OC_1$-$C_6$ alkyl;
$R_4$ and $R_5$ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and Q is phenyl, a substituted phenyl, or the ring-structure of formula II:

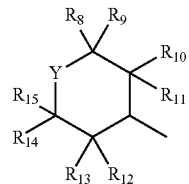

wherein Y is O or C(R$_6$R$_7$); and

R$_6$, R$_7$ R$_8$, R$_9$, R$_{10}$, R$_{11}$, R$_{12}$, R$_{13}$, R$_{14}$, and R$_{15}$ are independently H, hydroxyl, halogen, oxo, keto, C$_1$-C$_6$ alkyl, or OC$_1$-C$_6$ alkyl.

In yet aspects of this embodiment, the present specification discloses the compounds of formula I and pharmaceutically acceptable forms thereof:

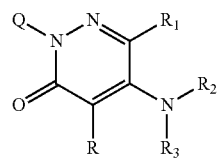

wherein R is H, halogen, hydroxyl, oxo, keto, C$_1$-C$_3$ alkyl, or OC$_1$-C$_3$ alkyl;

R$_1$ is H, halogen, C$_1$-C$_3$ alkyl, or OC$_1$-C$_3$ alkyl;

R$_2$ is C$_1$-C$_6$ alkyl, C$_2$-C$_6$ alkyl substituted by N(R$_4$R$_5$), or C$_2$-C$_6$ alkyl substituted by OH;

R$_3$ is H, or C$_1$-C$_6$ alkyl;

R$_4$ and R$_5$ are independently C$_1$-C$_4$ alkyl, morpholine, or piperidine; and Q is the ring-structure of formula II:

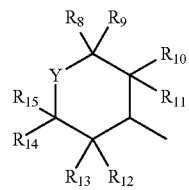

wherein Y is O or C(R$_6$R$_7$);

R$_6$ and R$_7$ are independently H or halogen; and

R$_8$, R$_9$, R$_{10}$, R$_{11}$, R$_{12}$, R$_{13}$, R$_{14}$, and R$_{15}$ are independently H or C$_1$-C$_2$ alkyl, provided at least two are not hydrogen.

In still other aspects of this embodiment, the present specification discloses the compounds of formula I and pharmaceutically acceptable forms thereof wherein R$_8$, R$_9$, R$_{14}$, and R$_{15}$ are methyl; R$_{10}$, R$_{11}$, R$_{12}$, and R$_{13}$ are hydrogen; and Y is CH$_2$. In yet further aspects, the compound is 5-hydroxy-2-(3,3,5,5-tetramethylcyclohexyl)pyridazin-3-one, 4,5-Dichloro-2-(3,3,5,5-tetramethylcyclohexyl)pyridazin-3-one, 4-Chloro-5-methylamino-2-(3,3,5,5-tetramethylcyclohexyl)pyridazin-3-one, 4-Chloro-5-dimethylamino-2-(3,3,5,5-tetramethylcyclohexyl)pyridazin-3-one, 4-Chloro-5-propylamino-2-(3,3,5,5-tetramethylcyclohexyl)pyridazin-3-one, 5-Methylamino-2-(3,3,5,5-tetramethylcyclohexyl)pyridazin-3-one, 5-Dimethylamino-2-(3,3,5,5-tetramethylcyclohexyl)pyridazin-3-one, 5-Propylamino-2-(3,3,5,5-tetramethylcyclohexyl)pyridazin-3-one, 5-Propyloxy-2-(3,3,5,5-tetramethylcyclohexyl)pyridazin-3-one, 4-Chloro-5-(2-morpholin-4-ylethylamino)-2-(3,3,5,5-tetramethylcyclohexyl)pyridazin-3-one, 4-Chloro-5-(2-dimethylaminoethylamino)-2-(3,3,5,5-tetramethylcyclohexyl)pyridazin-3-one, 4-Bromo-5-propylamino-2-(3,3,5,5-tetramethylcyclohexyl)pyridazin-3-one, 4-Bromo-5-(2-dimethylaminoethylamino)-2-(3,3,5,5-tetramethylcyclohexyl)pyridazin-3-one, 4-Bromo-5-(2-morpholin-4-ylethylamino)-2-(3,3,5,5-tetramethylcyclohexyl)pyridazin-3-one, 4-Chloro-5-(2-dimethylamino ethylmethylamino)-2-(3,3,5,5-tetramethylcyclohexyl)pyridazin-3-one, or 4-Chloro-5-(2-diethylaminoethylamino)-2-(3,3,5,5-tetramethylcyclohexyl)pyridazin-3-one.

In further aspects of this embodiment, the present specification discloses the compounds of formula I and pharmaceutically acceptable forms thereof include, without limitation, the following:

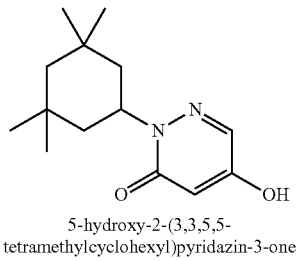

(Compound 1)

5-hydroxy-2-(3,3,5,5-tetramethylcyclohexyl)pyridazin-3-one

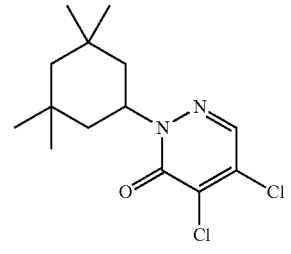

(Compound 2)

4,5-Dichloro-2-(3,3,5,5-tetramethylcyclohexyl)pyridazin-3-one

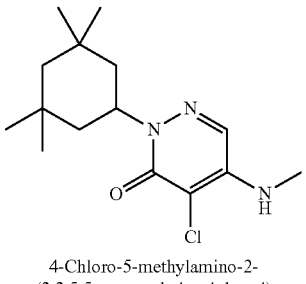

(Compound 3)

4-Chloro-5-methylamino-2-(3,3,5,5-tetramethylcyclohexyl)pyridazin-3-one

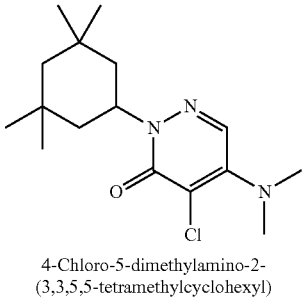

(Compound 4)

4-Chloro-5-dimethylamino-2-(3,3,5,5-tetramethylcyclohexyl)pyridazin-3-one

-continued

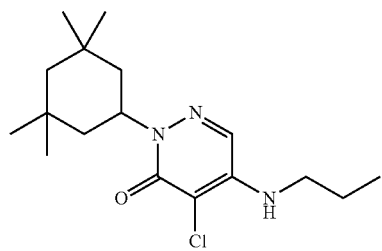
(Compound 5)
4-Chloro-5-propylamino-2-
(3,3,5,5-tetramethylcyclohexyl)
pyridazin-3-one

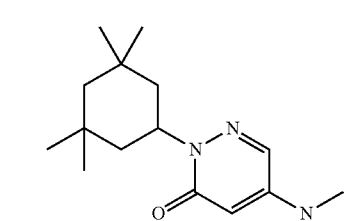
(Compound 6)
5-Methylamino-2-(3,3,5,5-
tetramethylcyclohexyl)pyridazin-3-one

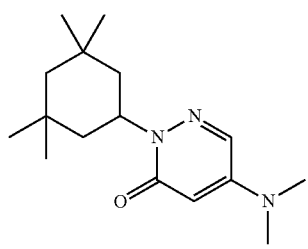
(Compound 7)
5-Dimethylamino-2-(3,3,5,5-
tetramethylcyclohexyl)pyridazin-3-one

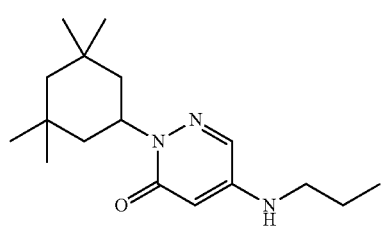
(Compound 8)
5-Propylamino-2-(3,3,5,5-
tetramethylcyclohexyl)pyridazin-3-one

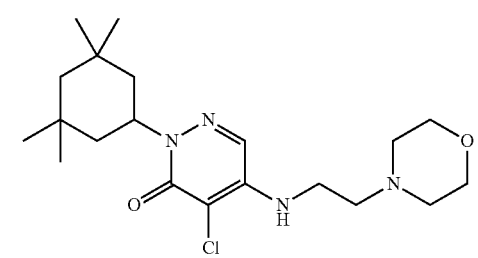
(Compound 11)
4-Chloro-5-(2-morpholin-4-
ylethylamino)-2-(3,3,5,5-
tetramethylcyclohexyl)pyridazin-3-one

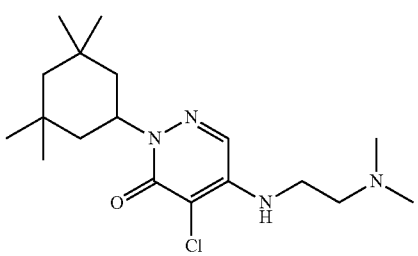
(Compound 12)
4-Chloro-5-(2-dimethylamino
ethylamino)-2-(3,3,5,5-
tetramethylcyclohexyl)pyridazin-3-one

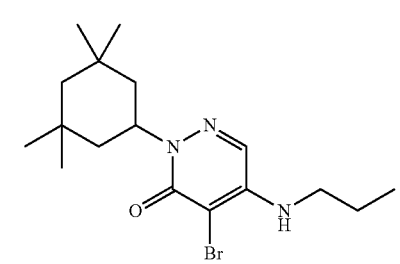
(Compound 13)
4-Bromo-5-propylamino-2-
(3,3,5,5-tetramethylcyclohexyl)
pyridazin-3-one

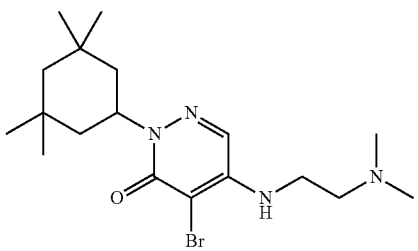
(Compound 14)
4-Bromo-5-(2-dimethylamino
ethylamino)-2-(3,3,5,5-
tetramethylcyclohexyl)pyridazin-3-one

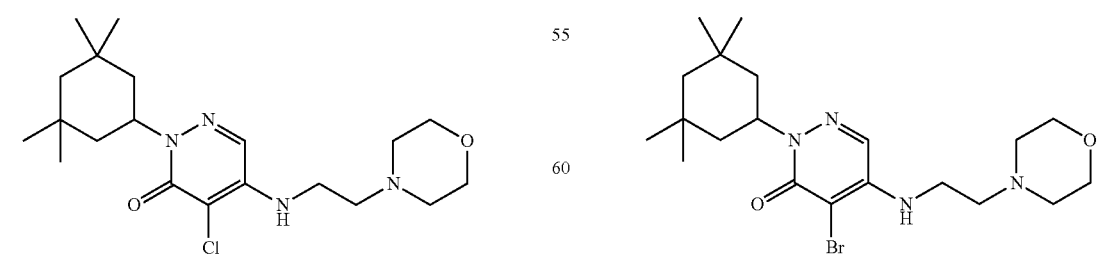
(Compound 15)
4-Bromo-5-(2-morpholin-4-
ylethylamino)-2-(3,3,5,5-
tetramethylcyclohexyl)pyridazin-3-one -continued

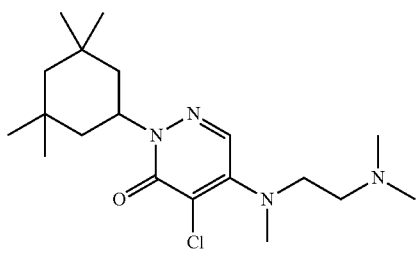

4-Chloro-5-(2-dimethylamino
ethylmethylamino)-2-(3,3,5,5-
tetramethylcyclohexyl)pyridazin-3-one
(Compound 31)

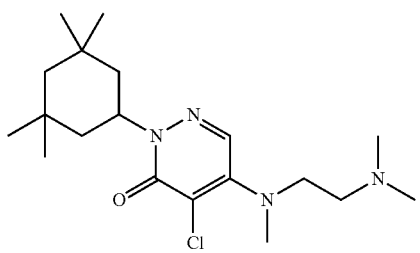

4-Chloro-5-(2-diethylamino
ethylamino)-2-(3,3,5,5-
tetramethylcyclohexyl)pyridazin-3-one
(Compound 32)

In another embodiment, the present specification discloses the compounds of formula III and pharmaceutically acceptable forms thereof:

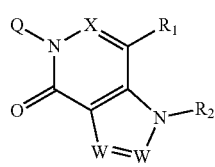

III wherein X is N, O, S or C(R₄R₅)

W is N, O, S, or CH;

R₁ and R₂ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl;

R₄ and R₅ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and Q is phenyl, a substituted phenyl, or the ring-structure of formula II:

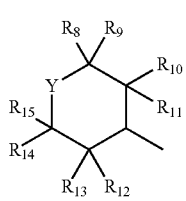

II wherein Y is N, O, S or C(R₆R₇); and

R₆, R₇, R₈, R₉, R₁₀, R₁₁, R₁₂, R₁₃, R₁₄, and R₁₅ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl.

In other aspects of this embodiment, the present specification discloses the compounds of formula III and pharmaceutically acceptable forms thereof:

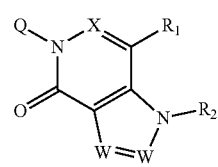

III wherein X is N or CH;

W is N or CH;

R₁ is H, halogen, hydroxyl, oxo, keto, C₁-C₆ alkyl, or OC₁-C₆ alkyl;

R₂ is H, halogen, hydroxyl, oxo, keto, C₁-C₆ alkyl, OC₁-C₆ alkyl, C₂-C₆ alkyl substituted by N(R₄R₅), or C₂-C₆ alkyl substituted by OH;

R₄ and R₅ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and Q is phenyl, a substituted phenyl, or the ring-structure of formula II:

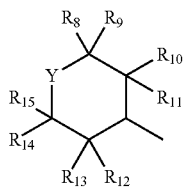

II wherein Y is O or C(R₆R₇); and

R₆, R₇ R₈, R₉, R₁₀, R₁₁, R₁₂, R₁₃, R₁₄, and R₁₅ are independently H, hydroxyl, halogen, oxo, keto, C₁-C₆ alkyl, or OC₁-C₆ alkyl.

In yet other aspects of this embodiment, the present specification discloses the compounds of formula III and pharmaceutically acceptable forms thereof:

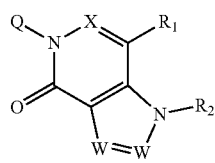

(III)

wherein R is H, halogen, $C_1$-$C_3$ alkyl, or $OC_1$-$C_3$ alkyl;
$R_1$ is H, halogen, $C_1$-$C_3$ alkyl, or $OC_1$-$C_3$ alkyl;
$R_2$ is $C_1$-$C_6$ alkyl, $C_2$-$C_6$ alkyl substituted by $N(R_4R_5)$, or $C_2$-$C_6$ alkyl substituted by OH;
$R_4$ and $R_5$ are independently $C_1$-$C_4$ alkyl, morpholine, or piperidine;
X is N or CH;
W is N or CH; and
Q is the ring-structure of formula II:

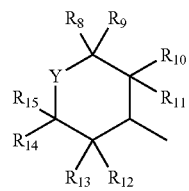

(II)

wherein Y is O or $C(R_6R_7)$;
$R_6$ and $R_7$ are independently H or halogen; and
$R_8$, $R_9$, $R_{10}$, $R_{11}$, $R_{12}$, $R_{13}$, $R_{14}$, and $R_{15}$ are independently H or $C_1$-$C_2$ alkyl, provided at least two are not hydrogen.

In still other aspects of this embodiment, the present specification discloses the compounds of formula III and pharmaceutically acceptable forms thereof, wherein $R_8$, $R_9$, $R_{14}$, and $R_{15}$ are methyl; $R_{10}$, $R_{11}$, $R_{12}$, and $R_{13}$ are hydrogen; and Y is $CH_2$. In yet further aspects of this composition, the compound is 1-Propyl-5-(3,3,5,5-tetramethyl cyclohexyl)pyrazolo[3,4-d]pyridazin-4-one, 2-Propyl-5-(3,3,5,5-tetramethyl cyclohexyl)pyrazolo[3,4-d]pyridazin-4-one, 1-(2-Morpholin-4-ylethyl)-5-(3,3,5,5-tetramethylcyclohexyl)pyrazolo[3,4-d]pyridazin-4-one, 2-(2-Morpholin-4-ylethyl)-5-(3,3,5,5-tetramethylcyclohexyl)pyrazolo[3,4-d]pyridazin-4-one, 1-(2-Dimethylaminoethyl)-5-(3,3,5,5-tetramethylcyclohexyl)pyrazolo[3,4-d]pyridazin-4-one, or 2-(2-Dimethylaminoethyl)-5-(3,3,5,5-tetramethylcyclohexyl)pyrazolo[3,4-d]pyridazin-4-one.

In further aspects of this embodiment, the present specification discloses the compounds of formula III and pharmaceutically acceptable forms thereof include, without limitation, the following:

(Compound 34)

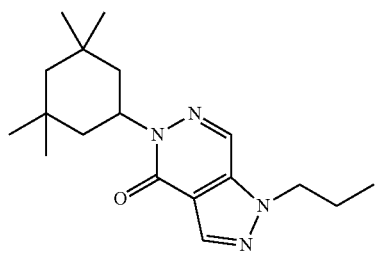

1-Propyl-5-(3,3,5,5-tetramethyl cyclohexyl)pyrazolo[3,4-d]pyridazin-4-one (Compound 35)

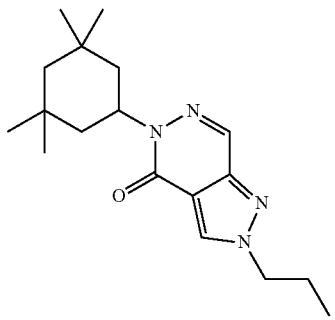

2-Propyl-5-(3,3,5,5-tetramethyl cyclohexyl)pyrazolo[3,4-d]pyridazin-4-one (Compound 36)

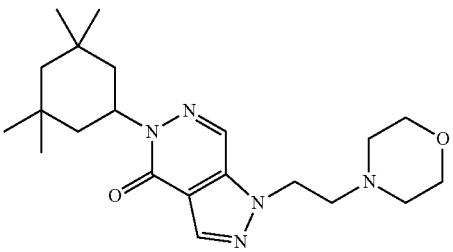

1-(2-Morpholin-4-ylethyl)-5-(3,3,5,5-tetramethylcyclohexyl)pyrazolo[3,4-d]pyridazin-4-one (Compound 37)

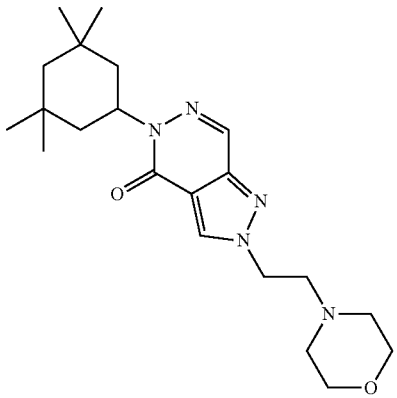

2-(2-Morpholin-4-ylethyl)-5-(3,3,5,5-tetramethylcyclohexyl)pyrazolo[3,4-d]pyridazin-4-one (Compound 38)

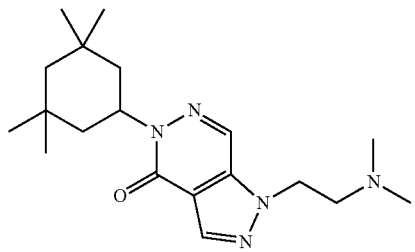

1-(2-Dimethylaminoethyl)-5-(3,3,5,5-tetramethylcyclohexyl)pyrazolo[3,4-d]pyridazin-4-one -continued (Compound 39)

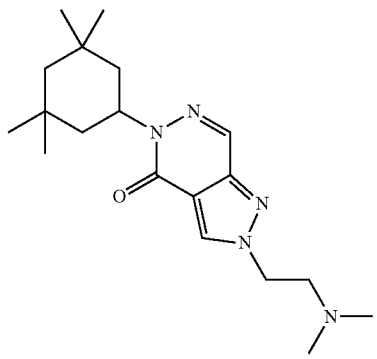

2-(2-Dimethylaminoethyl)-5-
(3,3,5,5-tetramethylcyclophexyl)
pyrazolo[3,4-d]pyridazin-4-one In other embodiment, the compounds of formula I or formula III have a greater binding selectiveity for the CB2 receptor relative to the CB1 receptor. In aspects of this embodiment, the compounds of formula I or formula III have a binding selectiveity for the CB2 receptor relative to the CB1 receptor that is, e.g., at least 10-fold greater, at least 15-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, at least 200-fold greater, at least 300-fold greater, at least 400-fold greater, at least 500-fold greater, at least 600-fold greater, at least 700-fold greater, at least 800-fold greater, at least 900-fold greater, or at least 1,000-fold greater. In other aspects of this embodiment, the compounds of formula I or formula III have a binding selectiveity for the CB2 receptor relative to the CB1 receptor that is from, e.g., about 10-fold greater to about 100-fold greater, about 10-fold greater to about 500-fold greater, about 10-fold greater to about 1,000-fold greater, about 20-fold greater to about 100-fold greater, about 20-fold greater to about 500-fold greater, about 20-fold greater to about 1,000-fold greater, about 30-fold greater to about 100-fold greater, about 30-fold greater to about 500-fold greater, or about 30-fold greater to about 1,000-fold greater.

Aspects of the present specification disclose, in part, a composition comprising a cannabinoid-2 agonist disclosed in the present specification. A composition comprising a cannabinoid-2 agonist is generally administered to an individual as a pharmaceutical composition. As used herein, the term "pharmaceutical composition" and refers to a therapeutically effective concentration of an active compound, such as, e.g., any of the cannabinoid-2 agonists disclosed in the present specification. Preferably, the pharmaceutical composition comprising a cannabinoid-2 agonist does not produce an adverse, allergic, or other untoward or unwanted reaction when administered to an individual. A pharmaceutical composition comprising a cannabinoid-2 agonist is useful for medical and veterinary applications. A pharmaceutical composition may be administered to an individual alone, or in combination with other supplementary active compounds, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir, or any other dosage form suitable for administration.

A pharmaceutical composition comprising a cannabinoid-2 agonist can optionally include a pharmaceutically acceptable carrier that facilitates processing of an active ingredient into pharmaceutically acceptable compositions. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); Remington: The Science and Practice of Pharmacy (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine and any modifications are well within the scope of one skilled in the art and from the teaching herein.

A pharmaceutical composition disclosed in the present specification can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

Thus, in an embodiment, a composition comprises a cannabinoid-2 agonist disclosed in the present specification. In an aspect of this embodiment, a pharmaceutical composition comprises a cannabinoid-2 agonist disclosed in the present specification and a pharmacological carrier. In another aspect of this embodiment, a pharmaceutical composition comprises a cannabinoid-2 agonist disclosed in the present specification and a pharmacological component. In yet another aspect of this embodiment, a pharmaceutical composition comprises a cannabinoid-2 agonist disclosed in the present specification, a pharmacological carrier, and a pharmacological component. In other aspects of this embodiment, a pharmaceutical composition comprises a cannabinoid-2 agonist disclosed in the present specification and at least one pharmacological carrier, at least one pharmaceutical component, or at least one pharmacological carrier and at least one pharmaceutical component. In another aspect of this embodiment, a pharmaceutical composition comprises about 0.001% to about 5% (w/v) of a cannabinoid-2 agonist, from 0% to 10% (w/v) of a preservative, 0% to 40% (w/v) of a vehicle, 1% to 10% (w/v) of a tonicity adjustor, 0.01% to 10% (w/v) of a buffer, q.s. (w/v) of a pH adjustor, an antioxidant as needed, a surfactant as needed, and purified water as needed to make 100%.

As can be demonstrated by the assays described in Example 24, the compounds disclosed in the present specification are useful in modulating CB2 receptor function. By virtue of this fact, these compounds have therapeutic use in treating disease-states and conditions mediated by the CB2 receptor function or that would benefit from modulation of the CB2 receptor function.

Peripherally, CB2 receptors are mostly expressed and function in cells of the immune system, such as, e.g., T cells, B cells, and macrophages; on cells of the hematopoietic system; and on cells of the gastrointestinal system. R. Mathison, et al., *Effects of Cannabinoid Receptor-2 Activation on Accelerated Gastrointestinal Transit in Lipopolysaccharide-Treated Rats*, Br. J. Pharmacol. 142(8): 1247-1254 (2004); K. L. Wright, et al., *Cannabinoid CB2 Receptors in the Gastrointestinal Tract: A Regulatory System in States Of Inflammation*, Br. J. Pharmacol. 153(2): 263-270. (2008). CB2 receptors are also expressed and function in keratinocytes and in nocicetive sensory neurons. In the brain, CB2 receptors are mainly expressed by microglial cells and not neurons. As such, activation of the CB2 receptor in microglial has no apparent behavioral or psychotropic effects in animals. G. A. Cabral, et al., *CB2 Receptors in the Brain: Role in Central Immune Function*, Br. J. Pharmacol. 153(2): 240-251 (2008).

The location of CB2 receptors on the surface of immune cells suggests a role for these receptors in immunomodulation and inflammation. G. Di Carlo and A. A. Izzo, *Cannabinoids for Gastrointestinal Diseases: Potential Therapeutic Applications*, Expert Opin Investig Drugs. 12(1): 39-49 (2003); F. Correa, et al., *The Role of Cannabinoid System on Immune Modulation: Therapeutic Implications on CNS Inflammation*, Mini Rev. Med. Chem. 5(7): 671-675 (2005); T. W. Klein, *Cannabinoid-Based Drugs as Anti-Inflammatory Therapeutics*, Nat Rev Immunol. 5(5): 400-411 (2005); F. Massa and K. Monory, *Endocannabinoids and the Gastrointestinal Tract*, J. Endocrinol. Invest. 29(3 Suppl): 47-57 (2006); T. W. Klein and G. A. Cabral, *Cannabinoid-Induced Immune Suppression and Modulation of Antigen-Presenting Cells*, J. Neuroimmune Pharmacol. 1(1): 50-64 (2006); J. C., Ashton, *Cannabinoids for the Treatment of Inflammation*, Curr. Opin. Investig. Drugs. 8(5): 373-384 (2007); D. Baker, et al., *Cannabinoid Control of Neuroinflammation Related to Multiple Sclerosis*, Br. J. Pharmacol. 152(5): 649-654 (2007); F. Correa, et al., *Cannabinoid System and Neuroinflammation: Implications For Multiple Sclerosis*, Neuroimmunomodulation 14(3-4): 182-187 (2007); D. Centonze, et al., *The Endocannabinoid System in Peripheral Lymphocytes as a Mirror of Neuroinflammatory Diseases*, Curr. Pharm. Des. 14(23): 2370-2342 (2008); and K. L. Wright, et al., *Cannabinoid CB2 Receptors in the Gastrointestinal Tract: A Regulatory System in States of Inflammation*, Br. J. Pharmacol. 153(2): 263-270 (2008). Inflammation refers to the actual tissue response (edema, erythema, etc) to a noxious stimulus. Neurogenic inflammation refers to the fact that this tissue response is initiated and/or maintained through the release of inflammatory mediators from peripheral sensory nerve terminals (i.e., an efferent function, in contrast to the normal afferent signaling to the spinal cord in these nerves). Analysis of the CB2 knockout mouse has corroborated the evidence for the function of CB2 receptors in modulating the immune system. CB2 receptors do not affect immune cell development and differentiation as determined by FACS analysis of cells from the spleen, lymph node and thymus from CB2 knockout mice, but rather mediates the suppressive effect of cannabinoids. Therefore, compounds that selectively interact with CB2 receptors offer a unique pharmacotherapy for the treatment of immune and inflammatory disorders. For example, such compounds could be effective in the treatment of autoimmune diseases including but not limited to multiple sclerosis, rheumatoid arthritis, systemic lupus erythematosus, myasthenia gravis, diabetes mellitus type I, inflammatory bowel disease or irritable bowel syndrome, psoriasis and other immune related disorders including but not limited to tissue rejection in organ transplants, malabsorption syndromes such as celiac disease, pulmonary diseases such as asthma and Sjogren's syndrome.

CB2 receptor agonists are effective in the treatment of acute and chronic pain, including inflammatory pain, nociceptive pain, and neuropathic pain, without causing the adverse side-effects associated with CB1 receptor activation. J. M. Walker and A. G. Hohmann, *Cannabinoid Mechanisms of Pain Suppression*, Handb Exp Pharmacol. 168: 509-554 (2005); Y. Cheng and S. A. Hitchcock, *Targeting Cannabinoid Agonists for Inflammatory and Neuropathic Pain*, Expert Opin. Investig. Drugs 16(7): 951-965 (2007); M. D. Jhaveri, et al., *Cannabinoid CB2 Receptor-Mediated Anti-Nociception in Models of Acute and Chronic Pain*, Mol. Neurobiol. 36(1): 26-35 (2007); G. T. Whiteside, et al., *The Role of the Cannabinoid CB2 Receptor in Pain Transmission and Therapeutic Potential of Small Molecule CB2 Receptor Agonists*, Curr. Med. Chem. 14(8): 917-936 (2007); J. Guindon and A. G. Hohmann, *Cannabinoid CB2 Receptors: A Therapeutic Target For the Treatment of Inflammatory and Neuropathic Pain*, Br. J. Pharmacol. 153(2): 319-334 (2008); and M. Beltramo, *Cannabinoid Type 2 Receptor as a Target For Chronic Pain*, Mini Rev Med. Chem. 9(1): 11-25 (2009). Activation of peripheral CB2 receptors is sufficient to normalize nociceptive thresholds and produce antinociception in persistent pain states. A. G. Hohmann, et al., A, *Selective Activation of Cannabinoid CB2 Receptors Suppresses Hype-* ralgesia Evoked by Intradermal Capsaicin, J. Pharmacol. Exp. Ther., 308(2): 446-453 (2004). For example, the CB2 receptor-selective compound AM1241 has been shown to be active in several animal models of acute and chronic inflammatory pain, including spinal nerve ligation, acute thermal nociceptive pain, carrageenan-induced thermal hyperalgesia and intradermal capsaicin-evoked hyperalgesia. T. P. Malan, Jr., et al., *CB2 Cannabinoid Receptor-Mediated Peripheral Antinociception*, Pain, 93(3): 239-245 (2001); M. M. Ibrahim, et al., *Activation of CB2 Cannabinoid Receptors by AM1241 Inhibits Experimental Neuropathic Pain: Pain Inhibition by Receptors Not Present in the CNS*, Proc. Natl. Acad. Sci. USA 100: 10529-10533 (2003); A. Quartilho, et al., *Inhibition of Inflammatory Hyperalgesia by Activation of Peripheral CB2 Cannabinoid Receptors*, Anesthesiology, 99(4): 955-960 (2003); A. G. Nackley, et al., *Selective Activation of Cannabinoid CB2 Receptors Suppresses Spinal Fos Protein Expression and Pain Behavior in a Rat Model of Inflammation*, Neurosci. 119(3): 747-757 (2003); Hohmann et al., J. Pharmacol. Exp. Ther.: 308, 446-53 (2004); M. M. Ibrahim, et al., *CB2 Cannabinoid Receptor Mediation of Antinociception*, Pain 122(1-2): 36-42 (2006); J. R. Ineck, Cannabinoid Analgesia as a Potential New Therapeutic Option in the Treatment of Chronic Pain, Ann. Pharmacother., 40(2): 251-260 (2006); T. Gutierrez, et al., *Activation of Peripheral Cannabinoid CB1 and CB2 Receptors Suppresses the Maintenance of Inflammatory Nociception: A Comparative Analysis*, Br. J. Pharmacol., 150(2): 153-163 (2007). The CB2 receptor-selective partial agonist GW405833 has also been shown to be efficacious in inflammatory, neuropathic, and surgical models of pain. Valenzano et al., Neuropharmacology 48:658-72 (2005). Activation of the CB2 receptor produces antinociception following surgical incision, suggesting that selective cannabinoid CB2 receptor agonists might be useful in the management of postoperative pain. C. J. LaBuda, et al., *Cannabinoid CB2 Receptor Agonist Activity in the Hindpaw Incision*, Eur. J. Pharmacol. 527(1-3): 172-174 (2005). A recent study revealed that oral delivery of *Lactobacillus acidophilus* induced the expression of CB2 receptors in the intestinal epithelium suggesting that CB2 receptor modulators may be useful for the treatment of abdominal pain associated with gastrointestinal diseases such as irritable bowel syndrome. Rousseaux et al., Nat. Med. 13: 35-37 (2007). Therefore, compounds that selectively target CB2 receptors represent an attractive approach for the development of novel pain treatments. The pain may be somatogenic (either nociceptive or neuropathic), acute and/or chronic.

CB2 receptors are expressed in osteoblasts, osteocytes, and osteoclasts and their signaling plays a key role in the maintenance of bone mass. I. A. Bab, *Regulation of Skeletal Remodeling by the Endocannabinoid System*, Ann. N.Y. Acad. Sci. 1116: 414-422 (2007); I. Bab and A. Zimmer, *Cannabinoid Receptors and the Regulation of Bone Mass*, Br. J. Pharmacol. 153(2): 182-188 (2008). For example, CB2 receptor agonists enhance endocortical osteoblast number and activity while restraining trabecular osteoclastogenesis. Another important effect is that CB2 receptor agonists attenuate ovariectomy-induced bone loss while increasing cortical thickness. For example, the CB2-selective agonist HU-308 mitigates ovariectomy-induced bone loss in mice. O. Ofek, et al., *Peripheral Cannabinoid Receptor, CB2, Regulates Bone Mass*, Proc. Natl. Acad. Sci. U.S.A. 103 (3): 696-701 (2006); and A. I. Idris, et al., *Regulation of Bone Mass, Osteoclast Function, and Ovariectomy-Induced Bone Loss by the Type 2 Cannabinoid Receptor*, Endocrinology, 149(11): 5619-5626 (2008). Consistent with this study, CB2 knockout mice were shown to have reduced bone mass. These findings suggest that modulation of CB2 receptor function offers a potential molecular target for the diagnosis and treatment of osteoporosis.

Recent studies have shown that CB2 modulators may be of benefit for the treatment of liver diseases such as liver fibrosis, ischemia-reperfusion injury, hepatic encephalopathy and non-alcoholic fatty liver disease (NAFLD). A. Mallat and S. A. Lotersztajn, *Cannabinoid Receptors as Therapeutic Targets in the Management of Liver Diseases*, Drug News Perspect. 21(7): 363-368 (2008); S. A, Lotersztajn, et al., *CB2 Receptors as New Therapeutic Targets For Liver Diseases*, Br. J. Pharmacol. 153(2): 286-289 (2008); Parfieniuk and R. Flisiak, *Role of Cannabinoids in Chronic Liver Diseases*, World Gastroenterol. 14(40): 6109-6114 (2008). Liver fibrosis is driven by chronic liver injury and ultimately leads to the development of cirrhosis. CB2 receptors are expressed in hepatocytes derived from individuals diagnosed with NAFLD but not from normal liver samples. Mendez-Sanchez, et al., Liver Int. 27(2): 215-219 (2007). Expression of CB2 has also been shown to be highly upregulated in myofibroblasts isolated from cirrhotic human livers. B. Julien, et al., *Antifibrogenic Role of the Cannabinoid Receptor CB2 in the Liver*, Gastroenterology 128: 742-755 (2006). In a mouse model of liver fibrosis, CB2 receptor knockout animals displayed a significantly enhanced fibrotic phenotype as compared to wild type controls. S. Lotersztajn, et al., *CB2 Receptors as New Therapeutic Targets For Liver Diseases*, Br. J. Pharmacol. 153(2): 286-289 (2008). Interestingly, treatment of liver myofibroblasts with a CB2 receptor agonist results in inhibition of cell growth and triggers apoptosis. B. Julien, et al., *Antifibrogenic Role of the Cannabinoid Receptor CB2 in the Liver* Gastroenterology 128: 742-755 (2006). Thus, activation of CB2 may limit fibrosis by interfering with the growth of liver fibrogenic cells. Taken together, these data suggest that CB2 receptor-selective agonists hold promise as therapeutics for a range of liver diseases.

CB2 receptor agonists are of potential benefit for the treatment of atherosclerosis. S. Steffens and F. Mach F, *Cannabinoid Receptors in Atherosclerosis*, Curr. Opin. Lipidol. 17(5): 519-526 (2006); F. Mach and S. Steffens, *The Role of the Endocannabinoid System in Atherosclerosis*, J. Neuroendocrinol. Suppl 1: 53-57 (2008); F. Mach, et al., *Cannabinoid Receptors in Acute and Chronic Complications of Atherosclerosis*, Br. J. Pharmacol. 153(2): 290-298 (2008). Low dose treatment of apoE knockout mice with a cannabinoid has been shown to reduce atherosclerosis progression. Furthermore, these effects are abrogated by treatment with a CB2 receptor-selective antagonist. S. Steffens et al., *Low Dose Oral Cannabinoid Therapy Reduces Progression of Atherosclerosis in Mice*, Nature. 434(7034): 782-786 (2005).

The role of CB2 receptors in the brain may have possible therapeutic uses in the treatment of neurological and neurodegenerative disorders, such as, e.g., Alzheimer's disease amyotrophic lateral sclerosis, and Huntington's disease. J. L. Croxford, *Therapeutic Potential of Cannabinoids in CNS Disease*, CNS Drugs. 17(3):179-202 (2003); C. Benito, et al., *Cannabinoid CB2 Receptors and Fatty Acid Amide Hydrolase are Selectively Overexpressed in Neuritic Plaque-Associated Glia in Alzheimer's Disease Brains*, J. Neurosci. 23 (35): 11136-1141 (2003); A. Alsasua del Valle A, *Implication of Cannabinoids in Neurological Diseases*, Cell Mol. Neurobiol. 26(4-6): 579-591 (2006); J. C. Ashton and M. Glass, *The Cannabinoid CB2 Receptor as a Target for Inflammation-Dependent Neurodegeneration*, Curr Neuropharmacol 5(2): 73-80 (2007); V. Micale, et al., *Endocannabinoids and Neurodegenerative Diseases*, Pharmacol Res. 56(5): 382-392 (2007); D. Baker and G. Pryce, *The Endocannabinoid System and Multiple Sclerosis*, Curr Pharm Des. 14(23): 2326-2336

(2008); L. G. Bilsland and L. Greensmith, *The Endocannabinoid System in Amyotrophic Lateral Sclerosis*, Curr Pharm Des. 14(23): 2306-2316 (2008); M. R. Pazos, et al., *The Endocannabinoid System in Huntington's Disease*, Curr. Pharm. Des. 14(23): 2317-2325 (2008); and B. S. Basavarajappa, et al., *Endocannabinoid System: Emerging Role from Neurodevelopment to Neurodegeneration*, Mini Rev Med. Chem. 9(4): 448-462 (2009). In addition, modulation of CB2 receptor activity may be important in disorders, such as, e.g., depression and drug addiction. J. Manzanares, et al., *Role of Endocannabinoid System in Mental Diseases*, Neurotox Res. 6(3): 213-224 (2004); and E. S. Onaivi, et al., *Discovery of the Presence and Functional Expression of Cannabinoid CB2 Receptors in Brain*, Ann. N.Y. Acad. Sci. 1074: 514-536 (2006).

CB2 receptor agonists also provide neuroprotective effects. D. Lamontagne, et al., *The Endogenous Cardiac Cannabinoid System: a New Protective Mechanism Against Myocardial Ischemia*, Arch Mal Coeur Vaiss. 99(3): 242-246 (2006); E. de Lago and J. Fernandez-Ruiz, *Cannabinoids and Neuroprotection in Motor-Related Disorders*, CNS Neurol. Disord. Drug Targets 6(6): 377-387 (2007); J. MartInez-Orgado, et al., *The Seek of Neuroprotection: Introducing Cannabinoids*, Recent Pat. CNS Drug Discov. 2(2): 131-139 (2007); O, Sagredo, et al., *Cannabinoids and Neuroprotection in Basal Ganglia Disorders*, Mol. Neurobiol. 36(1): 82-91 (2007); J. L. Croxford, et al., *Cannabinoid-Mediated Neuroprotection, Not Immunosuppression, May be More Relevant to Multiple Sclerosis*, J. Neuroimmunol. 193(1-2): 120-129 (2008); J. Fernandez-Ruiz, et al., *Role of CB2 Receptors in Neuroprotective Effects of Cannabinoids*, Mol. Cell. Endocrinol. 286(1-2 Suppl 1): S91-S96) (2008); P. Pacher and G. Haskó G, *Endocannabinoids and Cannabinoid Receptors in Ischaemia-Reperfusion Injury and Preconditioning*, Br. J. Pharmacol. 153(2): 252-262 (2008); S. Yazulla S, *Endocannabinoids in the Retina: from Marijuana to Neuroprotection*, Prog Retin Eye Res. 27(5): 501-526 (2008); and D. De Filippis, et al., *Differential Cannabinoid Receptor Expression During Reactive Gliosis: A Possible Implication for a Non-psychotropic Neuroprotection*, Scientific World Journal 9: 229-235 (2009).

Besides the general neuroprotective effect, CB2 receptor agonists can also treat more specific pathophysiological response to such diseases. Thus, for example, evidence for the tonic control of spasticity by the endocannabinoid system suggests that CB2 receptor agonists may help in the treatment of muscle spasm and tremor in multiple sclerosis, in addition to the possible moderation of the disease by immuno-modulation through an action on CB2 receptors expressed by immune cells. D. Baker, et al., *Cannabinoids Control Spasticity and Tremor in a Multiple Sclerosis Model*, Nature 404 (6773) 84-87 (2000); P. F. Smith, *Cannabinoids in the Treatment of Pain and Spasticity in Multiple Sclerosis*, Curr. Opin. Investig. Drugs, 3(6): 859-864 (2002); D. Baker and G. Pryce, *The Endocannabinoid System and Multiple Sclerosis*, Curr. Pharm. Des. 14(23): 2326-2336 (2008); and J. Fernández-Ruiz, *The Endocannabinoid System as a Target for the Treatment of Motor Dysfunction*, Br. J. Pharmacol. 156(7): 1029-1040 (2009).

Certain tumors, especially gliomas, express CB2 receptors, and two non-selective cannabinoid agonists induce the regression or eradication of malignant brain tumors in rats and mice. In addition, cells of the immune system express high levels of CB2 receptors which are involved in the induction of apoptosis in normal or transformed immune cells. Similarly, studies have shown that the CB2 receptor plays a very important role in the stimulation of growth of several, if not all, hematopoietic lineages. P. Valk et al., *Anandamide, A Natural Ligand for the Peripheral Cannabinoid Receptor is a Novel Synergistic Growth Factor for Hematopoietic Cells*, Blood, 90(4): 1448-1457 (1997); P. J. Valk and R. Delwel, *The Peripheral Cannabinoid Receptor, C82, in Retrovirally-Induced Leukemic Transformation and Normal Hematopoiesis*, Leuk. Lymphoma. 32(1-2): 29-43 (1998); J. M. Derocq, et al., *Genomic and Functional Changes Induced by the Activation of the Peripheral Cannabinoid Receptor C82 in the Promyelocytic Cells HL-60. Possible Involvement of the C82 Receptor in Cell Differentiation*, J. Biol. Chem. 275(21): 15621-15628 (2000). By using both murine and human leukemia and lymphoma lines as well as primary acute lymphoblastic leukemia (ALL) cells it has been shown that ligation of CB2 receptors can induce apoptosis in a wide range of cancers of immune-cell origin. L. C. Nagarkatti, et al., Treatment of Neoplasia, U.S. Patent Publication 2004/0259936, which is hereby incorporated by reference. Furthermore, TEC can inhibit the growth of murine lymphoma cells in vivo by inducing apoptosis and, in test experiments, completely cure approximately 25% of the mice bearing that tumor. This data suggest that CB2 receptor agonists constitute a novel and effective modality to treat malignancies of the immune and hematopoietic systems.

Recent studies have intriguingly suggested the existence of a functional endocannabinoid signaling system in the skin and implicated it in various biological processes, such as, e.g., proliferation, growth, differentiation, apoptosis and cytokine, mediator or hormone production of various cell types of the skin and appendages, such as the hair follicle and sebaceous gland. The main physiological function of the cutaneous endocannabinoid signaling is to constitutively control proper proliferation, differentiation and survival, as well as immune competence and/or tolerance, of skin cells. The disruption of this delicate balance might facilitate the development of multiple pathological conditions and diseases of the skin, such as, e.g., acne, seborrhea, allergic dermatitis, itch and pain, psoriasis, hair growth disorders, systemic sclerosis and cancer. T. Bíró, et al., *The Endocannabinoid System of the Skin in Health and Disease: Novel Perspectives and Therapeutic Opportunities*, Trends Pharmacol Sci. 30(8):411-420 (2009).

As used herein, the term "a CB2 receptor mediated syndrome, disorder, or disease" refers to any syndrome, disorder, or disease associated with a biological response mediated by a CB2 receptor such that there is discomfort or decreased life expectancy to the organism. CB2 receptor mediated diseases can occur in both animals and humans and include 1) an appetite related syndrome, disorder or disease; 2) a metabolism related syndrome, disorder or disease; 3) a diabetes related syndrome, disorder or disease; 4) an eye related syndrome, disorder or disease; 5) a social or mood related syndrome, disorder or disease; 6) a seizure related syndrome, disorder or disease; 7) a substance abuse related syndrome, disorder or disease; 8) a learning, cognition or memory related syndrome, disorder or disease; 9) an organ related syndrome, disorder or disease; 10) a vascular related syndrome, disorder or disease; 11) a dermatological related syndrome, disorder or disease; 12) a muscle spasm syndrome, disorder or disease; 13) a gastrointestinal related syndrome, disorder or disease; 14) a respiratory related syndrome, disorder or disease; 15) a locomotor activity or movement syndrome, disorder or disease; 16) a neurological or neurodegenerative related syndrome, disorder or disease; 17) hypreproliferative related syndrome, disorder or disease; 18) immune or inflammation related syndrome, disorder or disease; and 19) pain related syndrome, disorder or disease.

Aspects of the present invention provide, in part, where the CB2 receptor mediated syndrome, disorder, or disease is an appetite related syndrome, disorder, or disease. Such appetite related syndromes, disorders or diseases include, without limitation, obesity, overweight condition, anorexia, bulimia, cachexia, dysregulated appetite, and the like. Obesity related syndromes, disorders or diseases include obesity as a result of genetics, diet, food intake volume, metabolic syndrome, disorder or disease, hypothalmic disorder or disease, age, reduced activity, abnormal adipose mass distribution, abnormal adipose compartment distribution, and the like.

Aspects of the present invention provide, in part, where the CB2 receptor mediated syndrome, disorder, or disease is a metabolism related syndrome, disorder, or disease. Such metabolism related syndromes, disorders or diseases include, without limitation, metabolic syndrome, dyslipidemia, elevated blood pressure, diabetes, insulin sensitivity or resistance, hyperinsulinemia, hypercholesterolemia, hyperlipidemias, hypertriglyceridemias, atherosclerosis, hepatomegaly, steatosis, abnormal alanine aminotransferase levels, inflammation, atherosclerosis, and the like.

Aspects of the present invention provide, in part, where the CB2 receptor mediated syndrome, disorder, or disease is a diabetes related syndrome, disorder, or disease. Such diabetes related syndromes, disorders or diseases include, without limitation, glucose dysregulation, insulin resistance, glucose intolerance, hyperinsulinemia, dyslipidemia, hypertension, obesity, and the like.

Aspects of the present invention provide, in part, where the CB2 receptor mediated syndrome, disorder, or disease is an eye related syndrome, disorder, or disease. Such eye related syndromes, disorders or diseases include, without limitation, abnormal intraocular pressure, allergic keratitis, uveitis, or iritis, conjunctivitis, blepharitis, neuritis nervi optici, choroiditis, glaucoma and sympathetic ophthalmia, and the like.

Aspects of the present invention provide, in part, where the CB2 receptor mediated syndrome, disorder, or disease is a social or mood related syndrome, disorder, or disease. Such social or mood related syndromes, disorders or diseases include, without limitation, depression, anxiety, psychosis, social affective disorders or cognitive disorders, and the like.

Aspects of the present invention provide, in part, where the CB2 receptor mediated syndrome, disorder, or disease is a substance abuse related syndrome, disorder, or disease. Such substance abuse related syndromes, disorders or diseases include, without limitation, drug abuse, drug withdrawal, alcohol abuse, alcohol withdrawal, nicotine withdrawal, cocaine abuse, cocaine withdrawal, heroin abuse, heroin withdrawal, and the like.

Aspects of the present invention provide, in part, where the CB2 receptor mediated syndrome, disorder, or disease is a learning, cognition or memory related syndrome, disorder, or disease. Such learning, cognition or memory related syndromes, disorders or diseases include, without limitation, memory loss or impairment as a result of age, disease, side effects of medications (adverse events), and the like.

Aspects of the present invention provide, in part, where the CB2 receptor mediated syndrome, disorder, or disease is an organ related syndrome, disorder, or disease. Such organ related syndromes, disorders or diseases include, without limitation, renal syndromes, disorders or diseases, such as, e.g., nephrotic syndrome; and all types of nephritis, e.g., glomerulonephritis; pancreatits; hepatic syndromes, disorders or diseases, such as, e.g., acute liver cell disintegration; acute hepatitis of various genesis, e.g., viral, toxic, drug-induced; and chronically aggressive and/or chronically intermittent hepatitis; endocrine syndromes, disorders or diseases, such as, e.g., endocrine opthalmopathy, endocrine orbitopathia, thyrotoxic crisis, Thyroiditis de Quervain, Hashimoto thyroiditis, Morbus Basedow, granulomatous thyroiditis, struma lymphomatosa, and Graves disease, type I diabetes (insulin-dependent diabetes); organ and tissue transplantations and graft-versus-host diseases; and the like.

Aspects of the present invention provide, in part, where the CB2 receptor mediated syndrome, disorder, or disease is a vascular related syndrome, disorder, or disease. Such vascular related syndromes, disorders or diseases include, without limitation, panarteritis nodosa, polyarteritis nodosa, periarteritis nodosa, arteritis temporalis, Wegner granulomatosis, giant cell arthritis, atherosclerosis, reperfusion injury, erythema nodosum, and the like.

Aspects of the present invention provide, in part, where the CB2 receptor mediated syndrome, disorder, or disease is a dermatological related syndrome, disorder, or disease. Such dermatological related syndromes, disorders or diseases include, without limitation, dermatitis, psoriasis; sunburn, burns, eczema, and the like.

Aspects of the present invention provide, in part, where the CB2 receptor mediated syndrome, disorder, or disease is a muscle spasm related syndrome, disorder, or disease. Such muscle spasm related syndromes, disorders or diseases include, without limitation, multiple sclerosis, cerebral palsy, and the like.

Aspects of the present invention provide, in part, where the CB2 receptor mediated syndrome, disorder, or disease is a gastrointestinal related syndrome, disorder, or disease. Such gastrointestinal related syndromes, disorders or diseases include, without limitation, bowel dysmotility associated disorders (either accompanied by pain, diarrhea or constipation or without), irritable bowel syndrome and other forms of bowel dysmotility, inflammatory bowel diseases, regional enteritis (Crohns disease), ulcerative colitis, gastritis, apthhous ulcer, celiac disease, regional ileitis, gastroesophageal reflux disease, and the like.

Aspects of the present invention provide, in part, where the CB2 receptor mediated syndrome, disorder, or disease is a respiratory related syndrome, disorder, or disease. Such respiratory related syndromes, disorders or diseases include, without limitation, asthma, bronchitis, allergic rhinitis, emphysema, adult respiratory distress syndrome (ARDS), pigeon fanciers disease, farmers lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis, byssinosis and the like.

Aspects of the present invention provide, in part, where the CB2 receptor mediated syndrome, disorder, or disease is a locomotor activity and movement related syndrome, disorder, or disease. Such locomotor activity and movement related syndromes, disorders or diseases include, without limitation, stroke, Parkinson's disease, multiple sclerosis, epilepsy, and the like.

Aspects of the present invention provide, in part, where the CB2 receptor mediated syndrome, disorder, or disease is a neurological or neurodegenerative related syndrome, disorder, or disease. Such neurological or neurodegenerative related syndromes, disorders or diseases include, without limitation, brain edema and inflammation, particularly tumor-related brain edema; multiple sclerosis; acute encephalomyelitis; meningitis; acute spinal cord injury; trauma; ischemia or secondary biochemical injury collateral to traumatic head or brain injury; epilepsy; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection), Guillain-Barre syndrome, myasthenia gravis, stroke, various forms of seizures, e.g., nodding spasms, neuroprotection, such as, e.g., in the treatment of neurodegeneration following stroke, cardiac arrest, pulmonary bypass, traumatic brain injury, spinal cord injury, and the like.

Aspects of the present invention provide, in part, where the CB2 receptor mediated syndrome, disorder, or disease is a hypreproliferative related syndrome, disorder, or disease. Such hypreproliferative related syndromes, disorders or diseases include, without limitation, multiple myeloma, acute and chronic leukemias including acute lymphocytic leukemia (ALL), chronic lymphocytic leukemia (CLL), and chronic myelogenous leukemia (CLL), lymphomas, including Hodgkin's lymphoma and non-Hodgkin's lymphoma (low, intermediate, and high grade), lymphogranulomatoses, lymphosarcoma, adenomatous polyps, such as, e.g., familial adenomatous polyposis (FAP), as well as solid tumors and malignancies of the brain, head and neck, breast, lung, reproductive tract, upper digestive tract, pancreas, liver, renal, bladder, prostate, colorectal and skin (including melanomas), and the like.

Aspects of the present invention provide, in part, where the CB2 receptor mediated syndrome, disorder, or disease is an immune or inflammation related syndrome, disorder, or disease. Such immune or inflammation related syndromes, disorders or diseases include, without limitation, allergic related syndromes, disorders or diseases and chronic neurogenic inflammation related syndromes, disorders or diseases. An allergic related syndrome, disorder, or disease includes, e.g., all forms of allergic reactions, such as, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis.

Aspects of the present invention provide, in part, where the CB2 receptor mediated syndrome, disorder, or disease is a chronic neurogenic inflammation related syndromes, disorders or diseases. As used herein, the term "chronic neurogenic inflammation related syndrome, disorder or disease" means an inflammatory response having pathophysiology effects where at least one of the underlying symptoms being treated is due to a CB2 receptor function etiology. Chronic neurogenic inflammation includes both primary neurogenic inflammation and secondary neurogenic inflammation. As used herein, the term "primary" neurogenic inflammation refers to tissue inflammation (inflammatory symptoms) that is initiated by, or results from, the release of substances from primary sensory nerve terminals (such as C and A-delta fibers). As used herein, the term "secondary" neurogenic inflammation" refers to tissue inflammation initiated by non-neuronal sources (e.g., extravasation from vascular bed or tissue interstitium-derived, such as from mast cells or immune cells) of inflammatory mediators, such as peptides or cytokines, stimulating sensory nerve terminals and causing a release of inflammatory mediators from the nerves. These nerve-derived inflammatory mediators can, in turn, stimulate the sensory nerves as well as acting on non-neuronal targets (e.g., mast cells). The net effect of both forms (primary and secondary) of neurogenic inflammation is to have an inflammatory state that is maintained by the sensitization of the peripheral sensory nerve fibers. The physiological consequence of the resulting neurogenic inflammation depends on the tissue in question, producing, such as, e.g., cutaneous pain (allodynia, hyperalgesia), joint arthritis, visceral pain and dysfunction, pulmonary dysfunction (asthma, COPD), and bladder dysfunction (pain, overactive bladder).

Chronic neurogenic inflammation symptoms include, without limitation, edema, hyperemia, erythema, bruising, tenderness, stiffness, swollenness, fever, chills, stuffy nose, stuffy head, breathing problems, fluid retention, blood clots, loss of appetite, increased heart rate, formation of granulomas, fibrinous, pus, non-viscous serous fluid, or ulcer and pain. The actual symptoms associated with a chronic neurogenic inflammation are well known and can be determined by a person of ordinary skill in the art by taking into account factors, including, without limitation, the location of the neurogenic inflammation, the cause of the neurogenic inflammation, the severity of the neurogenic inflammation, the tissue or organ affected, and the associated disorder.

A chronic neurogenic inflammation symptom can be associated with a large, unrelated group of disorders which underly a variety of human diseases. Non-limiting examples of disorders exhibiting chronic neurogenic inflammation as a symptom include, without limitation, acne, acid reflux/heartburn, Alzheimer's disease, appendicitis, arteritis, arthritis, asthma. atherosclerosis, autoimmune disorders, balanitis, blepharitis, bronchiolitis, bronchitis, bursitis, cancer, carditis, celiac disease, cellulitis, cervicitis, cholangitis, cholecystitis, chorioamnionitis, chronic obstructive pulmonary disease (COPD), cirrhosis, colitis, conjunctivitis, cystitis, common cold, dacryoadenitis, dementia, dermatitis, dermatomyositis, emphysema, encephalitis, endocarditis, endometritis, enteritis, enterocolitis, epicondylitis, epididymitis, fasciitis, fibrositis, gastritis, gastroenteritis, gingivitis, glomerulonephritis, glossitis, heart disease, hepatitis, hidradenitis suppurativa, high blood pressure, ileitis, an inflammatory neuropathy, insulin resistance, interstitial cystitis, iritis, ischemic heart disease, keratitis, keratoconjunctivitis, laryngitis, mastitis, mastoiditis, meningitis, metabolic syndrome (syndrome X), a migraine, myelitis, myocarditis, myositis, nephritis, obesity, omphalitis, oophoritis, orchitis, osteochondritis, osteopenia, osteoporosis, osteitis, otitis, pancreatitis, Parkinson's disease, parotitis, a pelvic inflammatory disease, pericarditis, peritonitis, pharyngitis, phlebitis, pleuritis, pneumonitis, proctitis, prostatitis, pulpitis, pyelonephritis, pylephlebitis, rheumatic fever, rhinitis, salpingitis, sialadenitis, sinusitis, spastic colon, stomatitis, synovitis, tendonitis, tendinosis, tenosynovitis, thrombophlebitis, tonsillitis, trigonitis, a tumor, urethritis, uveitis, vaginitis, vasculitis, and vulvitis. See also, Eric R. First, Application of Botulinum Toxin to the Management of Neurogenic Inflammatory Disorders, U.S. Pat. No. 6,063,768, which is hereby incorporated by reference in its entirety.

One type of disorder exhibiting a symptom of chronic neurogenic inflammation is an arthritis. Arthritis includes a group of conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple disease and Behcet disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis)

or five or more joints (polyarthritis) and can be either an auto-immune disease or a non-autoimmune disease.

Another type of disorder exhibiting a symptom of chronic neurogenic inflammation are autoimmune disorders. Autoimmune diseases can be broadly divided into systemic and organ-specific autoimmune disorders, depending on the principal clinico-pathologic features of each disease. Systemic autoimmune diseases include, without limitation, systemic lupus erythematosus (SLE), Sjögren's syndrome, Scleroderma, rheumatoid arthritis and polymyositis. Local autoimmune diseases may be endocrinologic (Diabetes Mellitus Type 1, Hashimoto's thyroiditis, Addison's disease etc.), dermatologic (pemphigus vulgaris), hematologic (autoimmune haemolytic anemia), neural (multiple sclerosis) or can involve virtually any circumscribed mass of body tissue. Types of autoimmune disorders include, without limitation, acute disseminated encephalomyelitis (ADEM), Addison's disease, an allergy or sensitivity, anti-phospholipid antibody syndrome (APS), arthritis, autoimmune hemolytic anemia, autoimmune hepatitis, autoimmune inner ear disease, bullous pemphigoid, celiac disease, Chagas disease, chronic obstructive pulmonary disease (COPD), diabetes mellitus type 1 (IDDM), endometriosis, fibromyalgia, Goodpasture's syndrome, Graves' disease, Guillain-Barré syndrome (GBS), Hashimoto's thyroiditis, hidradenitis suppurative, idiopathic thrombocytopenic purpura, inflammatory bowel disease, interstitial cystitis, lupus (including discoid lupus erythematosus, drug-induced lupus erythematosus. lupus nephritis, neonatal lupus, subacute cutaneous lupus erythematosus and systemic lupus erythematosus), morphea, multiple sclerosis (MS), myasthenia gravis, myopathies, narcolepsy, neuromyotonia, pemphigus vulgaris, pernicious anaemia, primary biliary cirrhosis, recurrent disseminated encephalomyelitis (multiphasic disseminated encephalomyelitis), rheumatic fever, schizophrenia, scleroderma, Sjögren's syndrome, tenosynovitis, vasculitis, and vitiligo. See Pamela D. Van Schaack & Kenneth L. Tong, Treatment of Autoimmune Disorder with a Neurotoxin, U.S. Patent Publication 2006/138059, which is hereby incorporated by reference in its entirety.

Another type of disorder exhibiting a symptom of chronic neurogenic inflammation is an inflammatory myopathy. Inflammatory myopathies are caused by problems with the immune system attacking components of the muscle, leading to signs of inflammation in the muscle Inflammatory myopathies include, without limitation, dermatomyositis, inclusion body myositis, and polymyositis.

Another type of disorder exhibiting a symptom of chronic neurogenic inflammation is a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. The inflammation may affect any size blood vessel, anywhere in the body. It may affect either arteries and/or veins. The inflammation may be focal, meaning that it affects a single location within a vessel; or it may be widespread, with areas of inflammation scattered throughout a particular organ or tissue, or even affecting more than one organ system in the body. Vasculitis include, without limitation, Buerger's disease (thromboangiitis obliterans), cerebral vasculitis (central nervous system vasculitis), Churg-Strauss arteritis, cryoglobulinemia, essential cryoglobulinemic vasculitis, giant cell (temporal) arteritis, Golfers vasculitis, Henoch-Schonlein purpura, hypersensitivity vasculitis (allergic vasculitis), Kawasaki disease, microscopic polyarteritis/polyangiitis, polyarteritis nodosa, polymyalgia rheumatica (PMR), rheumatoid vasculitis, Takayasu arteritis, Wegener's granulomatosis, and vasculitis secondary to connective tissue disorders like systemic lupus erythematosus (SLE), rheumatoid arthritis (RA), relapsing polychondritis, Behget's disease, or other connective tissue disorders, vasculitis secondary to viral infection.

Another type of disorder exhibiting a symptom of chronic neurogenic inflammation is a skin disorder. Skin disorders include, without limitation, a dermatitis, including chronic actinic dermatitis, an eczema like atopic eczema, contact eczema, xerotic eczema, seborrhoeic dermatitis, dyshidrosis, discoid eczema, venous eczema, dermatitis herpetiformis, neurodermatitis, and autoeczematization, and statis dermatitis, hidradenitis suppurativa, psoriasis including plaqure psoriasis, nail psoriasis, guttate psoriasis, scalp psoriasis, inverse psoriasis, pustular psoriasis, and erythrodermis psoriasis, rosacea and scleroderma including morphea.

Another type of disorder exhibiting a symptom of chronic neurogenic inflammation is a gastrointestinal disorder. A gastrointestinal disorder includes, without limitation, irritable bowel disease, an inflammatory bowel disease including Crohn's disease and an ulcerative colitis like ulcerative proctitis, left-sided colitis, pancolitis and fulminant colitis.

Aspects of the present invention provide, in part, where the CB2 receptor mediated disease is pain. Pain is commonly segmented by duration (acute vs. chronic), intensity (mild, moderate, and severe), and type (nociceptive vs. neuropathic). Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as pain initiated or caused by a primary lesion or dysfunction in the nervous system. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

The compounds disclosed herein are useful to treat patients with neuropathy or inflammatory pain such as reflex sympathetic dystrophy/causalgia (nerve injury), peripheral neuropathy (including diabetic neuropathy), intractable cancer pain, complex regional pain syndrome, and entrapment neuropathy (carpel tunnel syndrome). The compounds are also useful in the treatment of pain associated with acute herpes zoster (shingles), postherpetic neuralgia (PHN), and associated pain syndromes such as ocular pain. The compounds are further useful as analgesics in the treatment of pain such as surgical analgesia, or as an antipyretic for the treatment of fever. Pain indications include, but are not limited to, post-surgical pain for various surgical procedures including post-cardiac surgery, dental pain/dental extraction, bunionectomy, pain resulting from cancer, muscular pain, mastalgia, pain resulting from dermal injuries, lower back pain, headaches of various etiologies, including migraine, and the like. The compounds are also useful for the treatment of pain-related disorders such as tactile allodynia and hyperalgesia. The compounds are also useful for the treatment of glaucoma. The pain may be somatogenic (either nociceptive or neuropathic), acute and/or chronic.

Furthermore, the compounds disclosed herein can be used in the treatment or prevention of opiate tolerance in patients needing protracted opiate analgesics, and benzodiazepine tolerance in patients taking benzodiazepines, and other addictive behavior, for example, nicotine addiction, alcoholism, and eating disorders. Moreover, the compounds and methods disclosed herein are useful in the treatment or prevention of drug withdrawal symptoms, for example treatment or prevention of symptoms of withdrawal from opiate, alcohol, or tobacco addiction.

Other disorders or conditions which can be advantageously treated by the compounds disclosed herein include inflammation. The compounds disclosed herein are useful as anti-inflammatory agents with the additional benefit of having significantly less harmful side effects. The compounds are useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. The compounds are also useful in treating osteoporosis and other related bone disorders.

These compounds can also be used to treat gastrointestinal conditions such as reflux esophagitis, diarrhea, inflammatory bowel disease, Crohn's disease, gastritis, irritable bowel syndrome and ulcerative colitis. The compounds may also be used in the treatment of pulmonary inflammation, such as that associated with viral infections and cystic fibrosis. In addition, compounds disclosed herein are also useful in organ transplant patients either alone or in combination with conventional immunomodulators. Yet further, the compounds disclosed herein are useful in the treatment of pruritis and vitaligo. In addition, the compounds can be used to treat insulin resistance and other metabolic disorders such as atherosclerosis that are typically associated with an exaggerated inflammatory signaling.

The compounds disclosed herein are useful to treat patients with ischemia, retinitis of ophthalmic diseases, such as glaucoma, retinal ganglion degeneration, ocular irritation, retinopathies, uveitis, ocular photophobia, and of inflammation and pain associated with acute injury to the eye tissue. Specifically, the compounds can be used to treat glaucomatous retinopathy and/or diabetic retinopathy. The compounds can also be used to treat post-operative inflammation or pain as from ophthalmic surgery such as cataract surgery and refractive surgery.

Still other disorders or conditions advantageously treated by the compounds disclosed herein include the prevention or treatment of hypreproliferative diseases, especially cancers. Hematological and non-hematological malignancies which may be treated or prevented include but are not limited to multiple myeloma, acute and chronic leukemias including Acute Lymphocytic Leukemia (ALL), Chronic Lymphocytic Leukemia (CLL), and Chronic Myelogenous Leukemia (CLL), lymphomas, including Hodgkin's lymphoma and non-Hodgkin's lymphoma (low, intermediate, and high grade), as well as solid tumors and malignancies of the brain, head and neck, breast, lung, reproductive tract, upper digestive tract, pancreas, liver, renal, bladder, prostate and colorectal. The compounds can also be used to treat fibrosis, such as that which occurs with radiation therapy. The present compounds can also be used to treat subjects having adenomatous polyps, including those with familial adenomatous polyposis (FAP). Additionally, the present compounds can be used to prevent polyps from forming in patients at risk of FAP. The compounds may also be used to treat malignancies of the skin including, but not limited to, melanomas.

The compounds disclosed herein may also be used in the treatment of autoimmune diseases including but not limited to multiple sclerosis, rheumatoid arthritis, systemic lupus erythematosus, myasthenia gravis, diabetes mellitus type I, inflammatory bowel disease or irritable bowel syndrome, psoriasis and other immune related disorders including but not limited to tissue rejection in organ transplants, malabsorption syndromes such as celiac disease, pulmonary diseases such as asthma and Sjogren's syndrome.

The compounds and pharmaceutical compositions of the present invention are also useful in the treatment and prevention of pruritis. The pruritis may be due to atopic dermatitis, eczema, or insect bites. Other forms of pruritis treatable or preventable by the compounds and pharmaceutical compositions of the present invention include ocular and/or otic pruritis, kidney dialysis-induced pruritis and opioid-induced pruritis.

The compounds and pharmaceutical compositions of the present invention are also useful in the treatment and prevention of skin disorders (e.g. sunburn, dermatitis, pruritis); lung disorders (e.g. chronic obstructive pulmonary disease, cough, asthma, bronchitis); ophthalmic disorders (e.g. glaucoma, retinitis, reinopathies, uveitis, conjunctivitis); gastrointestinal disorders (e.g. ulcerative colitis, irritable bowel syndrome, coeliac disease, inflammatory bowel disease, gastroesophageal reflux disease, organ transplant, nausea, emesis); cardiovascular disorders (e.g. stroke, cardiac arrest, atherosclerosis, myocardial ischemia); neurodegenerative, neuroinflammatory or psychiatric disorders (e.g. senile dementia, Alzheimer's disease, vascular dementia, amyotrophic lateral sclerosis, neuroinflammation, tinnitus); bladder disorders (e.g. bladder hyper-reflexia, cystitis) and cancer, such as for instance, lymphoblastic leukemia and lymphoma, acute myelogenous leukemia, chronic lymphocytic leukemia, glioma, skin cancer, breast cancer, prostate cancer, liver cancer, kidney cancer, lung cancer, pancreatic cancer.

In addition, compounds and pharmaceutical compositions of the present invention can be used to modulate bone formation and/or resorption for treating certain conditions including, but not limited to, ankylosing spondylitis, gout, arthritis associated with gout, osteoarthritis and osteoporosis.

Besides being useful for human treatment, certain compounds and formulations disclosed herein may also be useful for veterinary treatment of companion animals, exotic animals and farm animals, including mammals, rodents, rabbits, and the like. More preferred animals include horses, dogs, and cats.

Aspects of the present specification disclose, in part, administering to an individual a composition comprising a cannabinoid-2 agonist disclosed in the present specification. A composition comprising a cannabinoid-2 agonist can be administered to an individual using a variety of enteral or parenteral approaches including, without limitation, oral administration in any acceptable form, such as, e.g., tablet, liquid, capsule, powder, or the like; topical administration in any acceptable form, such as, e.g., drops, spray, creams, gels or ointments; intravascular administration in any acceptable form, such as, e.g., intravenous bolus injection, intravenous infusion, intra-arterial bolus injection, intra-arterial infusion and catheter instillation into the vasculature; peri- and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; and by placement device, such as, e.g., an implant, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., *Handbook of Biodegradable Polymers* (Abraham J. Domb et al., eds., Overseas Publishers Association, 1997). Delivery mechanisms for administering a composition comprising a cannabinoid-2 agonist to an individual are described in, e.g., Leonid Beigelman et al., Compositions for the Delivery of Negatively Charged Molecules, U.S. Pat. No. 6,395,713 (May 28, 2002); Vernon G. Wong & Mae W. L. Hu, Methods for Treating Inflammation-mediated Conditions of the Eye, U.S. Pat. No. 6,726,918; David A. Weber et al., Methods and Apparatus for Delivery of Ocular Implants, U.S. Patent Publication No. US2004/0054374; Thierry Nivaggioli et al., Biodegradable Ocular Implant, U.S. Patent Publication No. US2004/0137059; Patrick M. Hughes et al., Anti-Angiogenic Sustained Release Intraocular Implants and Related Methods, U.S. patent application Ser. No. 11/364,687; and Patrick M. Hughes et al., Sustained Release Intraocular Drug Delivery Systems, U.S. Patent Publication 2006/0182783, each of which is hereby incorporated by reference in its entirety.

The actual delivery mechanism used to administer a composition comprising a cannabinoid-2 agonist to an individual can be determined by a person of ordinary skill in the art by taking into account factors, including, without limitation, the type of disease, the location of the disease, the cause of the disease, the severity of the disease, the degree of relief desired, the duration of relief desired, the particular cannabinoid-2 agonist used, the rate of excretion of the cannabinoid-2 agonist used, the pharmacodynamics of the cannabinoid-2 agonist used, the nature of the other compounds to be included in the composition, the particular route of administration, the particular characteristics, history and risk factors of the patient, such as, e.g., age, weight, general health and the like, or any combination thereof.

Aspects of the present specification can also be described as follows:

1. A compound of formula I or a pharmaceutically acceptable salt thereof:

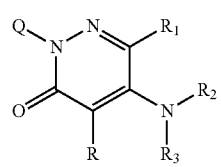

I wherein R, $R_1$, $R_2$, and $R_3$, are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and Q is six-member aryl, a six-member substituted aryl, or the ring-structure of formula II:

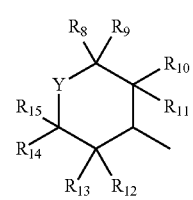

II wherein Y is N, O, S or $C(R_6R_7)$;

$R_6$, $R_7$, $R_8$, $R_9$, $R_{10}$, $R_{11}$, $R_{12}$, $R_{13}$, $R_{14}$, and $R_{15}$ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl.

2. The compound of 1, wherein R is H, halogen, hydroxyl, oxo, keto, $C_1$-$C_6$ alkyl, or $OC_1$-$C_6$ alkyl;

$R_1$ is H, halogen, hydroxyl, oxo, keto, $C_1$-$C_6$ alkyl, or $OC_1$-$C_6$ alkyl;

$R_2$ is H, halogen, hydroxyl, oxo, keto, $C_1$-$C_6$ alkyl, $OC_1$-$C_6$ alkyl, or $C_2$-$C_6$ alkyl substituted by $N(R_4R_5)$, or $C_2$-$C_6$ alkyl substituted by OH;

$R_3$ is H, halogen, hydroxyl, oxo, keto, $C_1$-$C_6$ alkyl, or $OC_1$-$C_6$ alkyl;

$R_4$ and $R_5$ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and Q is phenyl, a substituted phenyl, or the ring-structure of formula II:

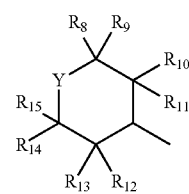

II wherein Y is O or $C(R_6R_7)$;

$R_6$, $R_7$ $R_8$, $R_9$, $R_{10}$, $R_{11}$, $R_{12}$, $R_{13}$, $R_{14}$, and $R_{15}$ are independently H, hydroxyl, halogen, oxo, keto, $C_1$-$C_6$ alkyl, or $OC_1$-$C_6$ alkyl.

3. The compound of 1, wherein R is H, halogen, hydroxyl, oxo, keto, $C_1$-$C_3$ alkyl, or $OC_1$-$C_3$ alkyl;

$R_1$ is H, halogen, $C_1$-$C_3$ alkyl, or $OC_1$-$C_3$ alkyl;

$R_2$ is $C_1$-$C_6$ alkyl, $C_2$-$C_6$ alkyl substituted by $N(R_4R_5)$, or $C_2$-$C_6$ alkyl substituted by OH;

$R_3$ is H, or $C_1$-$C_6$ alkyl;

$R_4$ and $R_5$ are independently $C_1$-$C_4$ alkyl, morpholine, or piperidine; and Q is the ring-structure of formula II:

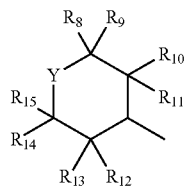

wherein Y is O or C($R_6R_7$);

$R_6$ and $R_7$ are independently H or halogen; and $R_8$, $R_9$, $R_{10}$, $R_{11}$, $R_{12}$, $R_{13}$, $R_{14}$, and $R_{15}$ are independently H or $C_1$-$C_2$ alkyl, provided at least two are not hydrogen.

4. The compound of 3, wherein $R_8$, $R_9$, $R_{14}$, and $R_{15}$ are methyl; $R_{10}$, $R_{11}$, $R_{12}$, and $R_{13}$ are hydrogen; and Y is $CH_2$.

5. The compound of 1, wherein the cannabinoid-2 agonist is 5-hydroxy-2-(3,3,5,5-tetramethylcyclohexyl)pyridazin-3-one, 4,5-Dichloro-2-(3,3,5,5-tetramethylcyclohexyl)pyridazin-3-one, 4-Chloro-5-methylamino-2-(3,3,5,5-tetramethylcyclohexyl)pyridazin-3-one, 4-Chloro-5-dimethylamino-2-(3,3,5,5-tetramethylcyclohexyl)pyridazin-3-one, 4-Chloro-5-propylamino-2-(3,3,5,5-tetramethylcyclohexyl)pyridazin-3-one, 5-Methylamino-2-(3,3,5,5-tetramethylcyclohexyl)pyridazin-3-one, 5-Dimethylamino-2-(3,3,5,5-tetramethylcyclohexyl)pyridazin-3-one, 5-Propylamino-2-(3,3,5,5-tetramethylcyclohexyl)pyridazin-3-one, 5-Propyloxy-2-(3,3,5,5-tetramethylcyclohexyl)pyridazin-3-one, 4-Chloro-5-(2-morpholin-4-ylethylamino)-2-(3,3,5,5-tetramethylcyclohexyl)pyridazin-3-one, 4-Chloro-5-(2-dimethylaminoethylamino)-2-(3,3,5,5-tetramethylcyclohexyl)pyridazin-3-one, 4-Bromo-5-propylamino-2-(3,3,5,5-tetramethylcyclohexyl)pyridazin-3-one, 4-Bromo-5-(2-dimethylaminoethylamino)-2-(3,3,5,5-tetramethylcyclohexyl)pyridazin-3-one, 4-Bromo-5-(2-morpholin-4-ylethylamino)-2-(3,3,5,5-tetramethylcyclohexyl)pyridazin-3-one, 4-Chloro-5-(2-dimethylamino ethylmethylamino)-2-(3,3,5,5-tetramethylcyclohexyl)pyridazin-3-one, or 4-Chloro-5-(2-diethylaminoethylamino)-2-(3,3,5,5-tetramethylcyclohexyl)pyridazin-3-one.

6. A pharmaceutical composition comprising the compound of 1.

7. A method of treating an individual suffering from a CB2 receptor mediated syndrome, disorder, or disease, the method comprising the step of administering to the individual a pharmaceutical composition of 6, wherein such administration reduces or eliminates a symptom associated with the CB2 receptor mediated syndrome, disorder, or disease.

8. The method of 7, wherein the CB2 receptor mediated syndrome, disorder, or disease is 1) an appetite related syndrome, disorder or disease; 2) a metabolism related syndrome, disorder or disease; 3) a diabetes related syndrome, disorder or disease; 4) an eye related syndrome, disorder or disease; 5) a social or mood related syndrome, disorder or disease; 6) a seizure related syndrome, disorder or disease; 7) a substance abuse related syndrome, disorder or disease; 8) a learning, cognition or memory related syndrome, disorder or disease; 9) an organ related syndrome, disorder or disease; 10) a vascular related syndrome, disorder or disease; 11) a dermatological related syndrome, disorder or disease; 12) a muscle spasm syndrome, disorder or disease; 13) a gastrointestinal related syndrome, disorder or disease; 14) a respiratory related syndrome, disorder or disease; 15) a locomotor activity or movement syndrome, disorder or disease; 16) a neurological or neurodegenerative related syndrome, disorder or disease; 17) hypreproliferative related syndrome, disorder or disease; 18) immune or inflammation related syndrome, disorder or disease; or 19) pain related syndrome, disorder or disease.

9. A compound of formula III or a pharmaceutically acceptable salt thereof:

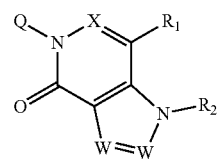

wherein X is N, O, S or C($R_4R_5$)

W is N, O, S, or CH;

$R_1$ and $R_2$ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl;

$R_4$ and $R_5$ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and Q is six-member aryl, a six-member substituted aryl, or the ring-structure of formula II:

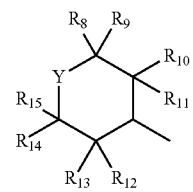

wherein Y is N, O, S or C($R_6R_7$); and $R_6$, $R_7$, $R_8$, $R_9$, $R_{10}$, $R_{11}$, $R_{12}$, $R_{13}$, $R_{14}$, and $R_{15}$ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl.

10. The compound of 9, wherein X is N or CH;
W is N or CH;
$R_1$ is H, halogen, hydroxyl, oxo, keto, $C_1$-$C_6$ alkyl, or $OC_1$-$C_6$ alkyl;
$R_2$ is H, halogen, hydroxyl, oxo, keto, $C_1$-$C_6$ alkyl, $OC_1$-$C_6$ alkyl, $C_2$-$C_6$ alkyl substituted by $N(R_4R_5)$, or $C_2$-$C_6$ alkyl substituted by OH;
$R_4$ and $R_5$ are independently H, hydroxyl, halogen, oxo, keto, unsubstituted or optionally substituted alkyl, unsubstituted or optionally substituted alkenyl, unsubstituted or optionally substituted alkynyl, unsubstituted or optionally substituted oxyalkyl, unsubstituted or optionally substituted thioalkyl, a six-member cycloalkyl, a six-member heterocycloalkyl, a six-member aryl, or a six-member heteroaryl; and
Q is phenyl, a substituted phenyl, or the ring-structure of formula II:

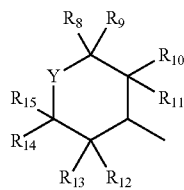

II wherein Y is O or $C(R_6R_7)$;
$R_6$, $R_7$ $R_8$, $R_9$, $R_{10}$, $R_{11}$, $R_{12}$, $R_{13}$, $R_{14}$, and $R_{15}$ are independently H, hydroxyl, halogen, oxo, keto, $C_1$-$C_6$ alkyl, or $OC_1$-$C_6$ alkyl.

11. The compound of 9, wherein R is H, halogen, $C_1$-$C_3$ alkyl, or $OC_1$-$C_3$ alkyl;
$R_1$ is H, halogen, $C_1$-$C_3$ alkyl, or $OC_1$-$C_3$ alkyl;
$R_2$ is $C_1$-$C_6$ alkyl, $C_2$-$C_6$ alkyl substituted by $N(R_4R_5)$, or $C_2$-$C_6$ alkyl substituted by OH;
$R_4$ and $R_5$ are independently $C_1$-$C_4$ alkyl, morpholine, or piperidine;
X is N or CH;
W is N or CH; and
Q is the ring-structure of formula II:

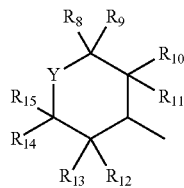

II wherein Y is O or $C(R_6R_7)$;
$R_6$ and $R_7$ are independently H or halogen; and
$R_8$, $R_9$, $R_{10}$, $R_{11}$, $R_{12}$, $R_{13}$, $R_{14}$, and $R_{15}$ are independently H or $C_1$-$C_2$ alkyl, provided at least two are not hydrogen.

12. The compound of 11, wherein $R_8$, $R_9$, $R_{14}$, and $R_{15}$ are methyl; $R_{10}$, $R_{11}$, $R_{12}$, and $R_{13}$ are hydrogen; and Y is $CH_2$.

13. The compound of 9, wherein the cannabinoid-2 agonist is 1-Propyl-5-(3,3,5,5-tetramethyl cyclohexyl)pyrazolo[3,4-d]pyridazin-4-one, 2-Propyl-5-(3,3,5,5-tetramethyl cyclohexyl)pyrazolo[3,4-d]pyridazin-4-one, 1-(2-Morpholin-4-ylethyl)-5-(3,3,5,5-tetramethylcyclohexyl)pyrazolo[3,4-d]pyridazin-4-one, 2-(2-Morpholin-4-ylethyl)-5-(3,3,5,5-tetramethylcyclohexyl)pyrazolo[3,4-d]pyridazin-4-one, 1-(2-Dimethylaminoethyl)-5-(3,3,5,5-tetramethylcyclohexyl)pyrazolo[3,4-d]pyridazin-4-one, or 2-(2-Dimethylaminoethyl)-5-(3,3,5,5-tetramethylcyclohexyl)pyrazolo[3,4-d]pyridazin-4-one.

14. A pharmaceutical composition comprising the compound of 9.

15. A method of treating an individual suffering from a CB2 receptor mediated syndrome, disorder, or disease, the method comprising the step of administering to the individual a pharmaceutical composition of 14, wherein such administration reduces or eliminates a symptom associated with the CB2 receptor mediated syndrome, disorder, or disease.

16. The method of 15, wherein the CB2 receptor mediated syndrome, disorder, or disease is 1) an appetite related syndrome, disorder or disease; 2) a metabolism related syndrome, disorder or disease; 3) a diabetes related syndrome, disorder or disease; 4) an eye related syndrome, disorder or disease; 5) a social or mood related syndrome, disorder or disease; 6) a seizure related syndrome, disorder or disease; 7) a substance abuse related syndrome, disorder or disease; 8) a learning, cognition or memory related syndrome, disorder or disease; 9) an organ related syndrome, disorder or disease; 10) a vascular related syndrome, disorder or disease; 11) a dermatological related syndrome, disorder or disease; 12) a muscle spasm syndrome, disorder or disease; 13) a gastrointestinal related syndrome, disorder or disease; 14) a respiratory related syndrome, disorder or disease; 15) a locomotor activity or movement syndrome, disorder or disease; 16) a neurological or neurodegenerative related syndrome, disorder or disease; 17) hypreproliferative related syndrome, disorder or disease; 18) immune or inflammation related syndrome, disorder or disease; or 19) pain related syndrome, disorder or disease.

17. A method of manufacturing a medicament, wherein the medicament comprises the compound of 1 or 9.

EXAMPLES

Example 1

General Scheme

The protected hydrazines may be prepared by condensing t-Butyl carbazate with a cyclic ketone in a solvent such as dimethylformamide to form the protected hydrazone. The reaction may be carried out at room temperature. The protected hydrazone is reduced to the protected hydrazine by hydrogenation over a palladium catalyst such as 10% palladium on charcoal in a solvent such as ethanol. Other reducing agents such as sodium borohydride or sodium triacetoxyborohydride may also be used.

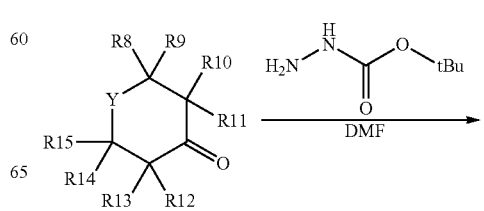

-continued

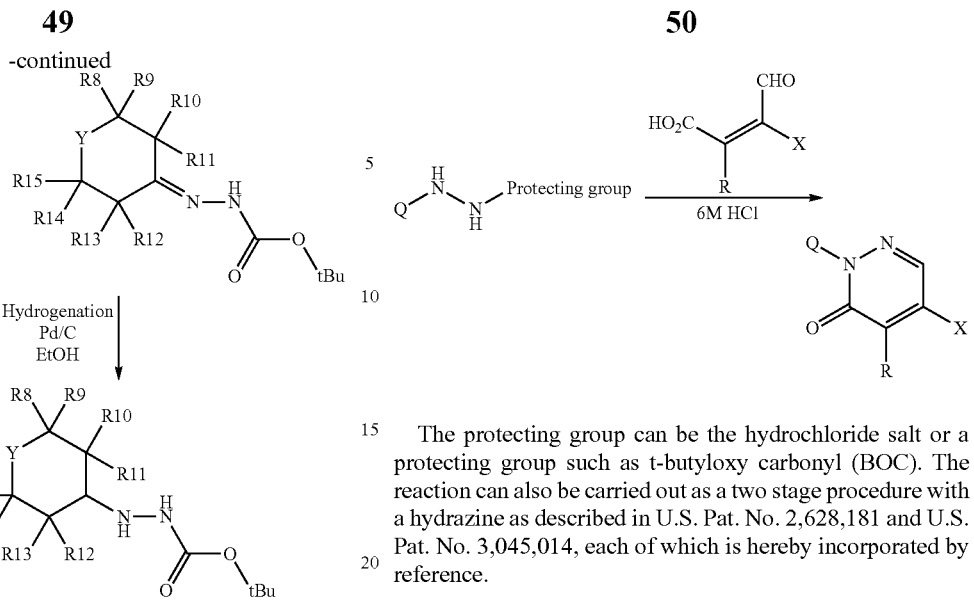

Hydrogenation
Pd/C
EtOH

The hydrazone is formed at room temperature in alcohol such as ethanol. The cyclization is carried out in acetic acid at 120° C. as shown in the scheme below.

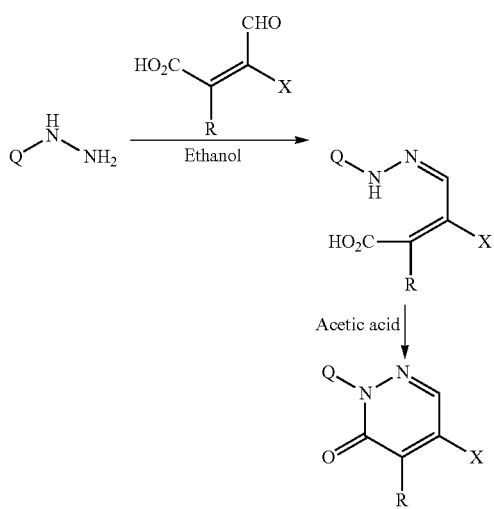

Compounds disclosed in the present specification may be prepared by displacement of a halogen with a suitable amine as shown in the following scheme:

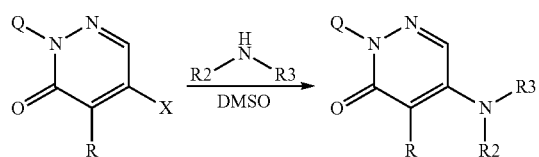

The reaction is carried out in a solvent such as DMSO at a temperature from room temperature to 130°, preferably 100°. The starting materials may be prepared by condensing a protected or unprotected hydrazine with mucochloric or mucobromic acid in a solvent such as 6M hydrochloric acid as shown in the scheme below. The mucochloric and mucobromic acids are well known in the literature and readily prepared by known methods.

The protecting group can be the hydrochloride salt or a protecting group such as t-butyloxy carbonyl (BOC). The reaction can also be carried out as a two stage procedure with a hydrazine as described in U.S. Pat. No. 2,628,181 and U.S. Pat. No. 3,045,014, each of which is hereby incorporated by reference.

Example 2

Synthesis of t-Butyl N'-(3,3,5,5-Tetramethylcyclohexyl)hydrazine carboxylate t-Butyl N'-(3,3,5,5-Tetramethylcyclohexylidene)hydrazine carboxylate (10.0 g, 0.0373 moles) was dissolved in ethanol (600 ml) and 5% Platinum on carbon (0.4 g) was added in water (2 mL). Stirred overnight under a hydrogen atmosphere (balloon). Filtered through HyFlo to remove the catalyst and evaporated the solvents to give a grey solid. Triturated with water and filtered off the grey solid. Dried in a desiccator to give the product as a grey solid (8.4 g, 83%). $^1$H NMR (300 MHz DMSO-$d_6$) 8.1 (brm, 1H), 4.1 (brm, 1H), 2.95 (m, 1H), 1.45 (m, 2H), 1.35 (s, 9H), 1.15 (m, 1H), 0.95 (m, 1H), 0.95 (s, 6H), 0.9 (s, 6H).

Example 3

Synthesis of t-Butyl N'-(3,3,5,5-Tetramethylcyclohexylidene)hydrazine carboxylate 3,3,5,5-Tetramethylcyclohexanone (7.7 g, 0.05 moles) was dissolved in DMF (50 mL) and t-butyl carbazate (6.6 g, 0.05 moles) was added to give a clear solution. Left to stand over the weekend. Poured into water and extracted into ethyl acetate. Washed with water and dried over anhydrous magnesium sulphate. Evaporated to give a white solid. Triturated with ether and dried in a desiccator to give the product as a white solid. (10.4 g, 78%). $^1$H NMR (300 MHz DMSO-$d_6$) mixture of isomers 9.5 and 7.95 (brs, 1H), 2.95 (s, 1H), 2.75 (s, 1H), 2.1 (s, 2H), 1.95 (s, 2H), 1.4 (s, 9H), 0.9 (2s, 12H).

Example 4

Synthesis of 4,5-Dichloro-2-(3,3,5,5-tetramethylcyclohexyl)pyridazin-3-one t-Butyl N'-(3,3,5,5-Tetramethylcyclohexyl)hydrazine carboxylate (5.0 g, 0.0194 moles) was suspended in 6M hydrochloric acid (375 mL) and mucochloric acid (3.28 g, 0.0194 moles) was added. Heated to reflux with stirring overnight and allowed to cool. Diluted with water and filtered off the product as a grey solid. Dried in a desiccator over phosphorus pentoxide. (4.89 g, 83%). $^1$H NMR (300 MHz CDCl$_3$) 7.8 (s, 1H), 5.25 (m, 1H), 1.55 (m, 4H), 1.3 (m, 1H), 1.15 (m, 1H), 1.15 (s, 6H), 0.95 (s, 6H).

Example 5

Synthesis of 4-Bromo-5-n-propylamino-2-(3,3,5,5-tetramethylcyclohexyl)pyridazin-3-one 4,5-Dibromo-2-(3,3,5,5-tetramethylcyclohexyl)pyridazin-3-one was prepared in a similar manner to 4,5-Dichloro-2-(3,3,5,5-tetramethylcyclohexyl)pyridazin-3-one. $^1$H NMR (300 MHz DMSO-d$_6$) 8.15 (m, 1H), 5.1 (m, 1H), 1.5 (m, 4H), 1.3 (m, 1H), 1.1 (m, 1H), 1.05 (s, 6H), 0.95 (s, 6H).

Example 6

Synthesis of 4-Chloro-5-methylamino-2-(3,3,5,5-tetramethylcyclohexyl)pyridazin-3-one 4,5-Dichloro-2-(3,3,5,5-tetramethylcyclohexyl)pyridazin-3-one (0.3 g, 1.475 mmoles) was dissolved in DMSO (20 mL) and a 40% aqueous solution of methylamine (0.6 mL, 1.7 mmoles) was added with stirring. Heated at 100° C. overnight. Allowed to cool and then poured into water. A solid precipitated out and was filtered off. Purified using a silica cartridge eluted with ethyl acetate:isohexane (3:7) to give the product as a cream solid (150 mg). $^1$H NMR (300 MHz CDCl$_3$) 7.65 (s, 1H), 5.35 (m, 1H), 4.7 (brs, 1H), 3.05 (d, 3H, J=5 Hz), 1.55 (m, 4H), 1.3 (m, 1H), 1.15 (m, 1H), 1.15 (s, 6H), 0.95 (s, 6H).

Example 7

Synthesis of 4-Chloro-5-dimethylamino-2-(3,3,5,5-tetramethylcyclohexyl)pyridazin-3-one 4-Chloro-5-dimethylamino-2-(3,3,5,5-tetramethylcyclohexyl)pyridazin-3-one (or 4-Chloro-5-(2-morpholin-4-yl-ethylamino)-2-(3,3,5,5-tetramethylcyclohexyl)pyridazin-3-one) was prepared from 4,5-Dichloro-2-(3,3,5,5-tetramethylcyclohexyl)pyridazin-3-one in a similar manner using a 2M solution of dimethylamine in methanol (4 equivalents). $^1$H NMR (300 MHz CDCl3) 7.64 (s, 1H), 5.3 (m, 1H), 3.1 (s, 6H), 1.55 (m, 4H), 1.3 (m, 1H), 1.15 (m, 1H), 1.15 (s, 6H), 0.95 (s, 6H).

Example 8

Synthesis of 4-Chloro-5-n-propylamino-2-(3,3,5,5-tetramethylcyclohexyl)pyridazin-3-one 4-Chloro-5-n-propylamino-2-(3,3,5,5-tetramethylcyclohexyl)pyridazin-3-one was prepared from 4,5-Dichloro-2-(3,3,5,5-tetramethylcyclohexyl)pyridazin-3-one in a similar manner using n-propylamine (4 equivalents). $^1$H NMR (300 MHz CDCl$_3$) 7.6 (s, 1H), 5.3 (m, 1H), 4.65 (brs, 1H), 3.5 (q, 2H, J=7 Hz), 1.72 (q, 2H, J=7 Hz), 1.55 (m, 4H), 1.3 (m, 1H), 1.15 (m, 1H), 1.15 (s, 6H), 1.04 (t, 3H, J=7 Hz), 0.95 (s, 6H).

Example 9

Synthesis of 4-Chloro-5-(2-dimethylaminoethyl)amino-2-(3,3,5,5-tetramethylcyclohexyl)pyridazin-3-one 4-Chloro-5-(2-dimethylaminoethyl)amino-2-(3,3,5,5-tetramethylcyclohexyl)pyridazin-3-one was prepared from 4,5-Dichloro-2-(3,3,5,5-tetramethyl cyclohexyl)pyridazin-3-one in a similar manner using 2-Dimethylaminoethyl amine (4 equivalents). $^1$H NMR (300 MHz CDCl$_3$) 7.60 (s, 1H), 5.44 (m, 1H), 5.33 (m, 1H), 3.33 (m, 2H), 2.59 (m, 2H), 2.29 (s, 6H), 1.55 (m, 4H), 1.3 (m, 1H), 1.15 (m, 1H), 1.15 (s, 6H), 0.95 (s, 6H).

Example 10

Synthesis of 4-Chloro-5-(2-dimethylaminoethyl)methylamino-2-(3,3,5,5-tetramethylcyclohexyl)pyridazin-3-one 4-Chloro-5-(2-dimethylaminoethyl)methylamino-2-(3,3,5,5-tetramethylcyclohexyl)pyridazin-3-one was prepared from 4,5-Dichloro-2-(3,3,5,5-tetramethyl cyclohexyl)pyridazin-3-one in a similar manner using 2-Dimethylaminoethyl methylamine (4 equivalents). $^1$H NMR (300 MHz CDCl$_3$) 7.68 (s, 1H), 5.28 (m, 1H), 3.54 (m, 2H), 3.1 (s, 3H), 2.56 (m, 2H), 2.26 (s, 6H), 1.55 (m, 4H), 1.3 (m, 1H), 1.15 (m, 1H), 1.15 (s, 6H), 0.95 (s, 6H).

Example 11

Synthesis of 4-Chloro-5-(2-dimethylaminoethyl)methylamino-2-(3,3,5,5-tetramethylcyclohexyl)pyridazin-3-one 4-Chloro-5-(2-dimethylaminoethyl)methylamino-2-(3,3,5,5-tetramethylcyclohexyl)pyridazin-3-one was prepared from 4,5-Dichloro-2-(3,3,5,5-tetramethyl cyclohexyl)pyridazin-3-one in a similar manner using 2-Dimethylaminoethyl methylamine (4 equivalents). $^1$H NMR (300 MHz CDCl$_3$) 7.68 (s, 1H), 5.28 (m, 1H), 3.54 (m, 2H), 3.1 (s, 3H), 2.56 (m, 2H), 2.26 (s, 6H), 1.55 (m, 4H), 1.3 (m, 1H), 1.15 (m, 1H), 1.15 (s, 6H), 0.95 (s, 6H).

Example 12

Synthesis of 4-Bromo-5-(2-dimethylaminoethyl)amino-2-(3,3,5,5-tetramethylcyclohexyl)pyridazin-3-one 4-Bromo-5-(2-dimethylaminoethyl)amino-2-(3,3,5,5-tetramethylcyclohexyl)pyridazin-3-one was prepared from 4,5-Dibromo-2-(3,3,5,5-tetramethyl cyclohexyl)pyridazin-3-one in a similar manner using 2-Dimethylaminoethyl amine (4 equivalents). $^1$H NMR (300 MHz CDCl$_3$) 7.51 (s, 1H), 5.53 (m, 1H), 5.33 (m, 1H), 3.34 (m, 2H), 2.60 (m, 2H), 2.3 (s, 6H), 1.55 (m, 4H), 1.3 (m, 1H), 1.15 (m, 1H), 1.15 (s, 6H), 0.95 (s, 6H).

Example 13

Synthesis of 4-Bromo-5-(2-morpholinoethyl)amino-2-(3,3,5,5-tetramethylcyclohexyl)pyridazin-3-one 4-Bromo-5-(2-morpholinoethyl)amino-2-(3,3,5,5-tetramethylcyclohexyl)pyridazin-3-one was prepared from 4,5-Dibromo-2-(3,3,5,5-tetramethyl cyclohexyl)pyridazin-3-one in a similar manner using 2-Morpholinoethyl amine (4 equivalents). $^1$H NMR (300 MHz CDCl$_3$) 7.51 (s, 1H), 5.67 (m, 1H), 5.33 (m, 1H), 3.78 (m, 4H), 3.38 (m, 2H), 2.70 (m, 2H), 2.52 (m, 4H), 1.55 (m, 4H), 1.3 (m, 1H), 1.15 (m, 1H), 1.15 (s, 6H), 0.95 (s, 6H)

Example 14

Synthesis of 4-Bromo-5-dimethylamino-2-(3,3,5,5-tetramethyl-cyclohexyl)-2H-pyridazin-3-one A solution of 4,5-Dibromo-2-(3,3,5,5-tetramethyl-cyclohexyl)-2H-pyridazin-3-one (1.059 g, 2.70 mmol) in EtOH/H$_2$O (15 mL, 2:1) was treated with a solution of N,N-dimethylamine in EtOH (5.6 M, 2 mL, 10.805 mmol). After stirring for 20 h at room temperature, the volatiles were removed in vacuo. The residue was dissolved in EtOAc, washed with brine, dried (Na$_2$SO$_4$), filtered and evaporated to provide 4-bromo-5-dimethylamino-2-(3,3,5,5-tetramethyl-cyclohexyl)-2H-yridazin-3-one (0.962 g, 100%) as a white solid. $^1$H NMR (300 MHz, CDCl$_3$) δ 7.57 (1H, s), 5.29 (1H, app tt, J=3.7, 12.1 Hz), 3.11 (6H, s), 1.64-1.45 (4H, m), 1.35-1.28 (2H, m), 1.14 (6H, s), 0.96 (6H, s).

Example 15

Synthesis of 5-Methylamino-2-(3,3,5,5-tetramethyl-cyclohexyl)pyridazin-3-one 4-Chloro-5-methylamino-2-(3,3,5,5-tetramethylcyclohexyl)pyridazin-3-one (0.15 g, 0.5 mmoles) was dissolved in ethanol (20 mL) and 1M sodium hydroxide (1 ml) was added. 10% Palladium on charcoal (40 mg) was added and the reaction mixture was stirred overnight under a balloon of hydrogen. Filtered off the catalyst and evaporated to a low bulk. Partitioned between water and ethyl acetate, separated and dried over magnesium sulphate. Evaporated to give the required product as a buff solid. (0.125 g, 94%). $^1$H NMR (300 MHz CDCl$_3$) 7.32 (d, 1H, J=3 Hz), 5.7 (d, 1H, J=3 Hz), 5.3 (m, 1H), 4.2 (brs, 1H), 2.85 (d, 3H, J=5 Hz), 1.55 (m, 4H), 1.3 (m, 1H), 1.15 (m, 1H), 1.15 (s, 6H), 0.95 (s, 6H).

Example 16

Synthesis of 5-Dimethylamino-2-(3,3,5,5-tetramethylcyclohexyl)pyridazin-3-one 5-Dimethylamino-2-(3,3,5,5-tetramethylcyclohexyl)pyridazin-3-one was prepared in a similar manner to 5-Methylamino-2-(3,3,5,5-tetramethylcyclohexyl)pyridazin-3-one. $^1$H NMR (300 MHz CDCl$_3$) 7.32 (d, 1H, J=3 Hz), 5.71 (d, 1H, J=3 Hz), 5.3 (m, 1H), 4.15 (brs, 1H), 2.85 (s, 3H), 2.83 (s, 3H), 1.55 (m, 4H), 1.3 (m, 1H), 1.15 (m, 1H), 1.15 (s, 6H), 0.95 (s, 6H).

Example 17

Synthesis of 5-n-Propylamino-2-(3,3,5,5-tetramethylcyclohexyl)pyridazin-3-one 5-n-Propylamino-2-(3,3,5,5-tetramethylcyclohexyl)pyridazin-3-one was prepared in a similar manner to 5-Methylamino-2-(3,3,5,5-tetramethylcyclohexyl)pyridazin-3-one. $^1$H NMR (300 MHz CDCl$_3$) 7.45 (m, 1H), 5.9 (m, 1H), 5.3 (m, 1H), 5.25 (brs, 1H), 3.1 (m, 2H), 1.7 (m, 2H), 1.55 (m, 4H), 1.3 (m, 1H), 1.15 (m, 1H), 1.15 (s, 6H), 1.05 (m, 3H), 0.95 (s, 6H).

Example 18

Synthesis of 5-Dimethylamino-3-oxo-2-(3,3,5,5-tetramethyl-cyclohexyl)-2,3-dihydro-yridazine-4-carbaldehyde A solution of 4-bromo-5-dimethylamino-2-(3,3,5,5-tetramethyl-cyclohexyl)-2H-yridazin-3-one (0.962 g, 2.70 mmol) in MeOH (30 mL) was treated with Pd/C (100 mg). The atmosphere was purged of oxygen under vacuo and replaced with H2. After stirring for 20 h at room temperature, the mixture was filtered over Celite and evaporated in vacuo to provide 5-dimethylamino-2-(3,3,5,5-tetramethyl-cyclohexyl)-2H-pyridazin-3-one (749 mg) which was directly used without further purification.

POCl$_3$ (0.9 mL, 9.75 mmol) was slowly added to precooled (0° C.), anhydrous DMF (5 mL). After stirring at room temperature for 30 min, a solution of 5-dimethylamino-2-(3,3,5,5-tetramethyl-cyclohexyl)-2H-pyridazin-3-one (749 mg, 2.70 mmol) in anhydrous DMF (6 mL) was added and the mixture was stirred at 70° C. for 1.5 h. After cooling, the mixture was poured over saturated NaHCO$_3$/ice. The aqueous layer was extracted with EtOAc (2×20 mL). The combined organics were dried (Na$_2$SO$_4$), filtered and evaporated in vacuo to provide 5-dimethylamino-3-oxo-2-(3,3,5,5-tetramethyl-cyclohexyl)-2,3-dihydro-pyridazine-4-carbaldehyde (1.19 g, 100%) as a white solid. $^1$H NMR (300 MHz, CDCl$_3$) δ 10.33 (1H, s), 7.80 (1H, s), 5.27 (1H, app tt, J=3.7, 11.7 Hz), 3.13 (6H, s), 1.63-1.44 (4H, m), 1.30 (2H, app t, J=11.0 Hz), 1.16 (6H, s), 0.98 (6H, s).

Example 19

Synthesis of 5-(3,3,5,5-tetramethyl-cyclohexyl)-1,5-dihydro-pyrazolo[3,4-d]pyridazin-4-one A solution of 5-dimethylamino-3-oxo-2-(3,3,5,5-tetramethyl-cyclohexyl)-2,3-dihydro-pyridazine-4-carbaldehyde (1.19 g, 3.903 mmol) in EtOH (30 mL) was treated with H$_2$NNH$_2$.H$_2$O (1.2 mL, 39.03 mmol). After stirring at reflux for 20 h, the volatiles were removed in vacuo and the solid residue was extracted with EtOAc. The organics were then washed with brine, dried (Na$_2$SO$_4$). After evaporation of volatiles, the residue was purified by flash chromatography (50 g (solute SiO$_2$ cartridge, continuous gradient 100% hexanes→hexanes/EtOAc, 1:1) to provide 5-(3,3,5,5-tetramethyl-cyclohexyl)-1,5-dihydro-pyrazolo[3,4-d]pyridazin-4-one (495.3 mg, 46%) as a white solid. $^1$H NMR (300 MHz, CDCl$_3$) δ 8.36 (1H, s), 8.31 (1H, s), 5.45 (1H, app heptet, J=4.6 Hz), 1.71-1.57 (4H, m), 1.40-1.22 (2H, m), 1.19 (6H, s), 1.00 (6H, s).

Example 20

Synthesis of 1-Propyl-5-(3,3,5,5-tetramethyl-cyclohexyl)-1,5-dihydro-pyrazolo[3,4-d]pyridazin-4-one A solution of 1-propyl-5-(3,3,5,5-tetramethyl-cyclohexyl)-1,5-dihydro-pyrazolo[3,4-d]pyridazin-4-one (85 mg, 0.31 mmol) and K$_2$CO$_3$ (64.2 mg, 0.465 mmol) in anhydrous DMF (2 mL) was treated with n-propylbromide (92 µL, 0.464 mmol). After stirring at room temperature for 20 h, the mixture was quenched with water. The aqueous layer was extracted with EtOAc (2×10 mL). The organics were combined, dried (MgSO$_4$), filtered and the volatiles were removed in vacuo. The residue was purified by flash chromatography (20 g (solute SiO$_2$ cartridge, continuous gradient 100% hexanes hexanes/EtOAc, 1:1) to provide 1-Propyl-5-(3,3,5,5-tetramethyl-cyclohexyl)-1,5-dihydro-pyrazolo[3,4-d]pyridazin-4-one (26.2 mg, 27%) as a white solid along with the regioisomer 2-Propyl-5-(3,3,5,5-tetramethyl-cyclohexyl)-1,5-dihydro-pyrazolo[3,4-d]pyridazin-4-one (47.2, 48%) as a white solid. $^1$H NMR (300 MHz, CDCl$_3$) δ 8.19 (1H, s), 8.14 (1H, s), 5.53-5.36 (1H, m), 4.31 (2H, t, J=7.1 Hz), 1.98 (2H, app sextet, J=7.5 Hz), 1.64-1.56 (4H, m), 1.31 (2H, app t, J=15.2 Hz), 1.23-1.2 (1H, m), 1.18 (6H, s), 0.98 (6H, s), 0.94 (3H, t, J=7.1 Hz).

Example 21

Synthesis of 1-(2-Morpholinoethyl)-5-(3,3,5,5-tetramethylcyclohexyl)pyrazolo[3,4-d]pyridazin-4-one 1-(2-Morpholinoethyl)-5-(3,3,5,5-tetramethylcyclohexyl)pyrazolo[3,4-d]pyridazin-4-one was prepared in a similar manner to 1-Propyl-5-(3,3,5,5-tetramethylcyclohexyl)pyrazolo[3,4-d]pyridazin-4-one. $^1$H NMR (300 MHz, CDCl$_3$) δ 8.17 (1H, s), 8.16 (1H, s), 5.49-5.36 (1H, m), 4.43 (2H, t, J=6.0 Hz), 3.62 (4H, app t, J=4.6 HZ), 2.83 (2H, t, J=6.2 Hz), 2.45 (4H, app t, J=4.6 Hz), 1.63-1.56 (2H, m), 1.37-1.19 (2H, m), 1.16 (6H, s), 0.97 (6H, s).

Example 22

Synthesis of 1-(2-Dimethylaminoethyl)-5-(3,3,5,5-tetramethylcyclohexyl)pyrazolo[3,4-d]pyridazin-4-one 1-(2-Dimethylaminoethyl)-5-(3,3,5,5-tetramethylcyclohexyl)pyrazolo[3,4-d]pyridazin-4-one was prepared in a similar manner to 1-Propyl-5-(3,3,5,5-tetramethylcyclohexyl)pyrazolo[3,4-d]pyridazin-4-one. $^1$H NMR (300 MHz, CDCl$_3$) δ 8.19 (1H, s), 8.18 (1H, s), 5.52-5.38 (1H, m), 4.42 (2H, t, J=6.4 Hz), 2.81 (2H, t, J=6.2 Hz), 2.28 (6H, s), 1.64-1.56 (4H, m), 1.32 (2H, t, J=15.2 Hz), 1.18 (6H, s), 0.98 (6H, s).

Example 23

Assays for CB2 Activity

A. Radioligand Binding Assay

Plasma membranes prepared from HEK 293 EBNA cells transfected with human CB1 or CB2 cannabinoid receptors (3.7 or 3.3 μmol/mg protein, receptor concentration; PerkinElmer) were used for the radioligand binding studies. The composition of incubation buffer for CB1 assay was 50 mM Tris base, 2.5 mM EDTA, 5 mM MgCl$_2$ and 0.5 mg/ml fatty acid free BSA and for CB2 assay was 50 mM Tris base, 2.5 mM EGTA, 5 mM MgCl$_2$ and 1 mg/ml fatty acid free BSA; pH was adjusted to 7.4 by adding 1N HCl. Plasma membranes were diluted with incubation buffer to provide a final protein concentration of 2.4 μg (CB1) or 8 μg (CB2) per well in non-binding surface polystyrene 96-well assay plates (Corning). Compound solutions were prepared in silanized glass tubes and dispensed using pipette tips with SUPERSLIK™ surface. Competition studies were performed using a final concentration of 0.72 nM [$^3$H]-CP 55,940 (100-180 Ci/mmol, specific activity; PerkinElmer) against test compounds. Non-specific binding was determined using 10 uM of unlabeled CP 55,940. Incubations were performed in 96-well assay plates at a final volume of 200 ul for 90 min (CB1) or 60 min (CB2) at room temperature. Binding reactions were terminated by the addition of ice-cold incubation buffer and rapid filtration through a glass fiber filter using a cell harvester (Inotech). This was followed by 8 additional washes. The glass fiber filter (0.26 mm thickness, 1-1.5 um retention; Inotech) was presoaked in cold incubation buffer containing 0.05% polyethylenimine. The filters were oven-dried at 50° C. for 60 min and counting performed using a Beckman Coulter LS 6500 Multi-Purpose Scintillation Counter (Beckman-Coulter). Binding was determined in duplicate for at least 4 separate experiments.

B. Mouse Isolated Vas Deferens (MVD) Bioassay

Smooth muscle tension of the isolated tissues was measured isometrically with force displacement transducers (Grass FT-03) and was recorded on a polygraph (Grass Model 7J) with low level DC amplifier (Grass Model 7P122). The jacketed 5-ml glass organ baths contained modified Krebs solution maintained at 31-33° C. and gassed with 95% O$_2$/5% CO$_2$ to give a pH of 7.4. The modified Mg$^{2+}$ free Krebs solution was prepared fresh on the day of the experiment and had the following composition (mM): NaCl, 118.2; KCl, 4.75; KH$_2$PO$_4$, 1.19; CaCl$_2$, 2.54; NaHCO$_3$, 25.0; glucose, 11.0. Test compounds were dissolved in ethanol at a stock concentration of 10 μM and diluted in 80% DMSO in normal saline. The test compounds had a final vehicle concentration of 0.1% ethanol and 0.37% DMSO in the organ bath. Compound solutions were prepared in heat-silanized glass vials that were covered with foil to protect from light. Vas deferens were collected from male Swiss Webster mice, at a minimum age of 6 weeks, for use in the bioassay. Two tissues, each of approximately 2 cm in length, were obtained from one animal. The vas deferens was suspended longitudinally using 4-0 silk sutures, with the epididymal end in the upper position, and equilibrated for 45-60 min under 0.4-0.5 g tension without electrical stimulation. Electrical current was generated by a Grass S88X stimulator and distributed to the individual organ baths using modified tungsten wire electrodes that extend into the organ baths, in parallel orientation to the tissues. Two electrodes were placed into each bath on opposite sides of the tissue. Tissue contractions were evoked by application of a train of electrical pulses. The electrical stimulation conditions were as follows: train rate 0.1 train/sec (TPS); train duration 500 ms; stimulation rate 5 pulses/sec (PPS); pulse delay 0.01 msec; pulse duration 0.5 msec; pulse size 10-14 V. Each tissue is electrically stimulated for 2 min, followed by a buffer wash, then 2-3 min rest. Voltage was applied between 10-14 V to determine the optimal setting. This cycle was repeated 3-4 times until the tissue contractions exhibited constant amplitude. Two electrically stimulated contractions were obtained for baseline readings and then, without washing the tissue, the test compound solution or vehicle was applied. Tissues were incubated with agonist or vehicle for 2-3 min and then electrically stimulated for 2 min. Investigational compounds or vehicle were evaluated in a cumulative manner and the tissue was not washed until dosing was completed. One concentration-response curve was obtained in each tissue. Responses were calculated by measuring the height of the electrically stimulated contractions. Data were represented as the average height of the last 1.5 min of each stimulation.

TABLE 1

| | | CB2 Activity | | | |
|---|---|---|---|---|---|
| Compound Number | Compound Name | CB1 Binding IC$_{50}$ (nM) | CB2 Binding IC$_{50}$ (nM) | CB2 Selectivity | MVD Assay EC$_{50}$ (nM) |
| 1 | 5-hydroxy-2-(3,3,5,5-tetramethylcyclohexyl)pyridazin-3-one | NA | 1,819 | — | 3,700 |

TABLE 1-continued

| | | CB2 Activity | | | |
|---|---|---|---|---|---|
| Compound Number | Compound Name | CB1 Binding IC$_{50}$ (nM) | CB2 Binding IC$_{50}$ (nM) | CB2 Selectivity | MVD Assay EC$_{50}$ (nM) |
| 2 | 4,5-Dichloro-2-(3,3,5,5-tetramethyl-cyclohexyl)pyridazin-3-one | >10,000 | 389 | >26 | >10,000 |
| 3 | 4-Chloro-5-methylamino-2-(3,3,5,5-tetramethylcyclohexyl)pyridazin-3-one | >10,000 | 355 | >28 | 2,900 |
| 4 | 4-Chloro-5-dimethylamino-2-(3,3,5,5-tetramethylcyclohexyl) pyridazin-3-one | 1,023 | 17 | 60 | 82 |
| 5 | 4-Chloro-5-propylamino--2-(3,3,5,5-tetramethylcyclohexyl)pyridazin-3-one | 1,023 | 5.4 | 189 | 30 |
| 6 | 5-Methylamino-2-(3,3,5,5-tetramethyl-cyclohexyl)pyridazin-3-one | >10,000 | 2,089 | >5 | 10,000 |
| 7 | 5-Dimethylamino-2-(3,3,5,5-tetramethylcyclohexyl)pyridazin-3-one | >10,000 | 380 | >26 | 2,500 |
| 8 | 5-Propylamino-2-(3,3,5,5-tetramethyl-cyclohexyl)pyridazin-3-one | >10,000 | 68 | >147 | 440 |
| 9 | 4-Chloro-2-phenyl-5-propylamino-pyridazin-3-one | NA | >10,000 | — | >10,000 |
| 10 | 4-Chloro-2-cyclohexyl-5-propylaminopyridazin-3-one | NA | 10,000 | — | >10,000 |
| 11 | 4-Chloro-5-(2-morpholin-4-ylethyl-amino)-2-(3,3,5,5-tetramethyl-cyclohexyl)pyridazin-3-one | 3,981 | 83 | 48 | 320 |
| 12 | 4-Chloro-5-(2-dimethylaminoethyl amino)-2-(3,3,5,5-tetramethyl-cyclohexyl)pyridazin-3-one | >10,000 | 204 | >49 | 2,900 |
| 13 | 4-Bromo-5-propylamino--2-(3,3,5,5-tetramethylcyclohexyl)pyridazin-3-one | 174 | 4.8 | 36 | 21 |
| 14 | 4-Bromo-5-(2-dimethylaminoethyl amino)-2-(3,3,5,5-tetramethyl-cyclohexyl)pyridazin-3-one | 7,413 | 42 | 177 | 820 |
| 15 | 4-Bromo-5-(2-morpholin-4-ylethylamino)-2-(3,3,5,5-tetramethylcyclohexyl)pyridazin-3-one | 1,862 | 22.4 | 83 | 86 |
| 16 | 4-Chloro-2-(3,5-dimethylphenyl)-5-propylaminopyridazin-3-one | >10,000 | 10,000 | — | >10,000 |
| 17 | 4-Chloro-5-dimethylamino-2-(3,5-dimethylphenyl)-pyridazin-3-one | NA | >10,000 | — | NA |
| 18 | 4-Chloro-2-(3,5-dimethylphenyl)-5-(2-morpholin-4-ylethylamino)-pyridazin-3-one | >10,000 | >10,000 | — | ~10,000 |
| 19 | 4-Chloro-5-(2-dimethylethylamino)-2-(3,5-dimethylphenyl)pyridazin-3-one | NA | NA | — | Not tested |
| 20 | 2-(3,5-Bistrifluoromethylphenyl)-4-chloro-5-propylamino-pyridazin-3-one | >10,000 | >10,000 | — | >10,000 |
| 21 | 2-(3,5-Bistrifluoromethylphenyl)-4-chloro-5-dimethylaminopyridazin-3-one | NA | >10,000 | — | >10,000 |
| 22 | 2-(3,5-Bistrifluoromethylphenyl)-4-chloro-5-(2-morpholin-4-ylethyl-amino)pyridazin-3-one | NA | >10,000 | — | >10,000 |
| 23 | 2-(3,5-Bistrifluoromethylphenyl)-4-chloro-5-(2-dimethylaminoethyl amino)pyridazin-3-one | NA | NA | — | Increase |
| 24 | 2-t-Butyl-4-chloro-5-propylamino-pyridazin-3-one | NA | >10,000 | — | >10,000 |
| 25 | 4-Chloro-2-(3,5-dichlorophenyl)-5-propylaminopyridazin-3-one | >10,000 | >10,000 | — | >10,000 |
| 26 | 4-Chloro-2-(2,5-dimethylphenyl)-5-propylaminopyridazin-3-one | NA | 10,000 | — | >10,000 |
| 27 | 2-t-Butyl-4-chloro-5-(2-morpholin-4-ylethylamino)-pyridazin-3-one | NA | >10,000 | — | >10,000 |
| 28 | 4-Chloro-2-(3,5-dichlorophenyl)-5-(2-morpholin-4-ylethylamino)-pyridazin-3-one | NA | >10,000 | — | Increase |
| 29 | 4-Chloro-2-(2,5-dimethylphenyl)-5-(2-morpholin-4-ylethylamino)-pyridazin-3-one | NA | >10,000 | — | >>10,000 |
| 30 | 2-Benzyl-4-chloro-5-propylaminopyridazin-3-one | NA | >10,000 | — | >10,000 |

TABLE 1-continued

| | | CB2 Activity | | | |
|---|---|---|---|---|---|
| Compound Number | Compound Name | CB1 Binding $IC_{50}$ (nM) | CB2 Binding $IC_{50}$ (nM) | CB2 Selectivity | MVD Assay $EC_{50}$ (nM) |
| 31 | 4-Chloro-5-(2-dimethylaminoethyl methylamino)-2-(3,3,5,5-tetramethyl-cyclohexyl)pyridazin-3-one | 2630 | 20 | 132 | 330 |
| 32 | 4-Chloro-5-(2-diethylaminoethyl amino)-2-(3,3,5,5-tetramethyl-cyclohexyl)pyridazin-3-one | NA | 1288 | — | 10,000 |
| 33 | 4-Chloro-2-(2,2-dimethylpropyl)-5-propylaminopyridazin-3-one | Not tested | Not tested | — | >10,000 |
| 34 | 1-Propyl-5-(3,3,5,5-tetramethyl-cyclohexyl)pyrazolo[3,4-d]pyridazin-4-one | 257 | 17 | 15 | 21 |
| 35 | 2-Propyl-5-(3,3,5,5-tetramethylcyclohexyl)pyrazolo[3,4-d]pyridazin-4-one | >10,000 | 240 | >42 | 1200 |
| 36 | 1-(2-Morpholin-4-ylethyl)-5-(3,3,5,5-tetramethylcyclohexyl)pyrazolo[3,4-d]pyridazin-4-one | 219 | 8.5 | 26 | 33 |
| 37 | 2-(2-Morpholin-4-ylethyl)-5-(3,3,5,5-tetramethylcyclohexyl)pyrazolo[3,4-d]pyridazin-4-one | >10,000 | 1,514 | >7 | 1400 |
| 38 | 1-(2-Dimethylaminoethyl)-5-(3,3,5,5-tetramethylcyclohexyl)pyrazolo[3,4-d]pyridazin-4-one | 3,981 | 105 | 38 | 130 |
| 39 | 2-(2-Dimethylaminoethyl)-5-(3,3,5,5-tetramethylcyclohexyl)pyrazolo[3,4-d]pyridazin-4-one | NA | 2042 | — | 2,900 |

NA = not active

Example 24

Treatment of an Appetite Related Syndrome, Disorder, or Disease

A 57 year old female complains that she is suffering from lack of mobility, shortness of breath, pounding heart beat, and a lack of energy. A physician diagnosis the patient with obesity. The woman is treated by taking, twice daily, a pill comprising a cannabinoid-2 agonist as disclosed in the present specification. The patient's condition is monitored on a weekly basis and after about 4 weeks from the start of treatment, the woman indicates that she is not as hungry as she was before the treatment. A physical examination shows that she has lost weight and that her percent body fat has been reduced. At two and three month check-ups, the woman still indicates that her appetite is suppressed and that she is losing more weight, can breathe easier and has more energy. The reduction in these symptoms indicates successful treatment with a composition comprising a cannabinoid-2 agonist as disclosed in the present specification. A similar treatment can be employed for a patient suffering from another type of appetite related syndrome, disorder, or disease.

Example 25

Treatment of a Metabolism Related Syndrome, Disorder, or Disease

A 63 year old man complains that he is suffering from shortness of breath and a lack of energy. A physician diagnosis the patient with elevated blood pressure. The man is treated by taking, once daily, a pill comprising a cannabinoid-2 agonist as disclosed in the present specification. The patient's condition is monitored on a weekly basis and after about 2 weeks from the start of treatment, the man indicates that he can breathe easier and has more energy. A physical examination shows that his blood pressure has dropped. At two and three month check-ups, the man still indicates that he can breathe easier and has more energy and an examination indicates that his blood pressure is within the normal range for a man his age. The reduction in these symptoms indicates successful treatment with a composition comprising a cannabinoid-2 agonist as disclosed in the present specification. A similar treatment can be employed for a patient suffering from another type of metabolism related syndrome, disorder, or disease.

Example 26

Treatment of a Diabetes Related Syndrome, Disorder, or Disease

A 49 year old man complains that he is suffering from dizziness. A physician diagnosis the patient with diabetes. The man is treated by taking, once daily, an injectable drug comprising a cannabinoid-2 agonist as disclosed in the present specification. The patient's condition is monitored on a weekly basis and after about 1 week from the start of treatment, the man indicates that his dizziness does not occur as often as it did before the start of treatment. A physical examination indicates that his glucose level has dropped. At one and three month check-ups, the man still indicates that he is less dizzy then before and an examination indicates that his glucose level is within the normal range for a man his age. The reduction in this symptom indicates successful treatment with a composition comprising a cannabinoid-2 agonist as disclosed in the present specification. A similar treatment can be employed for a patient suffering from another type of diabetes related syndrome, disorder, or disease.

Example 27

Treatment of an Eye Related Syndrome, Disorder, or Disease

A 58 year old woman complains that her sight is blurry. A physician diagnosis the patient with glaucoma. The woman is treated by injection of an implant comprising a cannabinoid-2 agonist as disclosed in the present specification. The patient's condition is monitored on a weekly basis and after about 4 week from the start of treatment, the woman indicates that her sight has improved. A physical examination indicates that her intraocular pressure has decreased. At two and three month check-ups, the woman still indicates that she has improved sight and an examination indicates that her intraocular pressure is within the normal range for a woman her age. The reduction in this symptom indicates successful treatment with a composition comprising a cannabinoid-2 agonist as disclosed in the present specification. A similar treatment can be employed for a patient suffering from another type of eye related syndrome, disorder, or disease.

Example 28

Treatment of a Social or Mood Related Syndrome, Disorder, or Disease

A 35 year old woman complains that she has no energy and is sad most of the time. A physician diagnosis the patient with depression. The woman is treated by taking, twice daily, a pill comprising a cannabinoid-2 agonist as disclosed in the present specification. The patient's condition is monitored on a weekly basis and after about 4 week from the start of treatment, the woman indicates that she has more energy and is less sad. A physical examination indicates that her depression has decreased. At two and three month check-ups, the woman still indicates that she has more energy and is less sad and an examination indicates that her mood is within the normal range for a woman her age. The reduction in this symptom indicates successful treatment with a composition comprising a cannabinoid-2 agonist as disclosed in the present specification. A similar treatment can be employed for a patient suffering from another type of social or mood related syndrome, disorder, or disease.

Example 29

Treatment of a Substance Abuse Related Syndrome, Disorder, or Disease

A 28 year old man complains of that he shakes all the time and that he blacks out on occasion. A physician diagnosis the patient with alcohol abuse. The man is treated by taking, once daily, a pill comprising a cannabinoid-2 agonist as disclosed in the present specification. He also is enrolled in an alcohol abuse program. The patient's condition is monitored on a weekly basis and after about 2 weeks from the start of treatment, the man indicates that he does not shake as often, has not black out and does not have as great a desire to drink liquor. A physical examination shows that his blood alcohol level has dropped. At two and three month check-ups, the man still indicates that he does not shake as often, has not black out since the treatment began, and does not have as great a desire to drink liquor. An examination indicates that his blood alcohol level is within the normal range for a man his age. The reduction in these symptoms indicates successful treatment with a composition comprising a cannabinoid-2 agonist as disclosed in the present specification. A similar treatment can be employed for a patient suffering from another type of substance abuse related syndrome, disorder, or disease.

Example 30

Treatment of an Organ Related Syndrome, Disorder, or Disease

A 70 year old woman complains of that she has trouble digesting her food and has pan in her upper abdomen. A physician diagnosis the patient with pancreatits. The woman is treated by taking, three times daily, a pill comprising a cannabinoid-2 agonist as disclosed in the present specification. The patient's condition is monitored on a weekly basis and after about 3 weeks from the start of treatment, the woman indicates that she can better digest her food and that the pain in her abdomen has lessen. A physical examination shows that the levels of pancreatic enzymes in her body have dropped. At two and three month check-ups, the woman still indicates that she can eat better and has no pain. An examination indicates that the levels of pancreatic enzymes in her body is within the normal range for a woman her age. The reduction in these symptoms indicates successful treatment with a composition comprising a cannabinoid-2 agonist as disclosed in the present specification. A similar treatment can be employed for a patient suffering from another type of organ related syndrome, disorder, or disease.

Example 31

Treatment of a Dermatological Related Syndrome, Disorder, or Disease

A 42 year old woman complains that the skin on her arms and legs are scaly and itch. A physician diagnosis the patient with psoriasis. The woman is treated by rubbing a cream comprising a cannabinoid-2 agonist as disclosed in the present specification on the effected area. The patient's condition is monitored on a weekly basis and after about 2 weeks from the start of treatment, the woman indicates that the scaly skin is disappearing and the itching is not as severe. A physical examination shows that the psoriasis is disappearing and the skin is healing. At two and three month check-ups, the woman indicates that her skin is much better, there are no scales and the itching is gone. An examination indicates that the woman's skin has healed and us within the normal range for a woman her age. The reduction in these symptoms indicates successful treatment with a composition comprising a cannabinoid-2 agonist as disclosed in the present specification. A similar treatment can be employed for a patient suffering from another type of dermatological related syndrome, disorder, or disease.

Example 32

Treatment of a Muscle Spasm Related Syndrome, Disorder, or Disease

A 38 year old man, previously diagnosed with multiple sclerosis, complains of muscle spasms. The man is treated by taking, twice daily, a pill comprising a cannabinoid-2 agonist as disclosed in the present specification. The patient's condition is monitored on a weekly basis and after about 2 weeks from the start of treatment, the man indicates that he does have the muscle spasms as frequently or as severely. At two and three month check-ups, the man indicates that he does not have any muscle spasms. The reduction in these symptoms indicates successful treatment with a composition comprising a cannabinoid-2 agonist as disclosed in the present specification. A similar treatment can be employed for a patient suffering from another type of muscle spasm related syndrome, disorder, or disease.

Example 33

Treatment of a Gastrointestinal Related Syndrome, Disorder, or Disease

A 49 year old man complains that he is suffering from abdominal pain and weight loss. A physician diagnosis the patient with irritable bowel syndrome. The man is treated by taking, three times daily, a pill comprising a cannabinoid-2 agonist as disclosed in the present specification. The patient's condition is monitored on a weekly basis and after about 4 week from the start of treatment, the man indicates that his pain has reduced in frequency and severity and that he has gained some weight. At two and three month check-ups, the man indicates that the pain is gone and that he has continued to gain more weight. An examination indicates that his weight is within the normal range for a man his age. The reduction in this symptom indicates successful treatment with a composition comprising a cannabinoid-2 agonist as disclosed in the present specification. A similar treatment can be employed for a patient suffering from another type of gastrointestinal related syndrome, disorder, or disease.

Example 34

Treatment of a Respiratory Related Syndrome, Disorder, or Disease

A 55 year old woman complains that she has trouble breathing. A physician diagnosis the patient with chronic obstructive pulmonary disease (COPD). The woman is treated by inhalation, four times daily, of a drug comprising a cannabinoid-2 agonist as disclosed in the present specification. The patient's condition is monitored on a weekly basis and after about 2 week from the start of treatment, the woman indicates that her breathing has improved. A physical examination indicates that the inflammation of her bronchi and bronchioles has decreased. At two and three month check-ups, the woman indicates that her breathing is good and an examination indicates that the diameter of her bronchi and bronchioles is within the normal range for a woman her age. The reduction in this symptom indicates successful treatment with a composition comprising a cannabinoid-2 agonist as disclosed in the present specification. A similar treatment can be employed for a patient suffering from another type of respiratory related syndrome, disorder, or disease.

Example 35

Treatment of a Locomotor Activity and Movement Related Syndrome, Disorder, or Disease A 44 year old man, previously diagnosed with Parkinson's disease, complains of difficulty in getting dressed, eating his food, writing, and walking, due to shaking caused by his condition. The man is treated by taking, twice daily, a pill comprising a cannabinoid-2 agonist as disclosed in the present specification. The patient's condition is monitored on a weekly basis and after about 2 weeks from the start of treatment, the man indicates that he has improved on his ability to get dressed, eat his food, write, and walk. At two and three month check-ups, the man indicates that he does not have any shaking and he can engage in normal locomotor activities. The reduction in these symptoms indicates successful treatment with a composition comprising a cannabinoid-2 agonist as disclosed in the present specification. A similar treatment can be employed for a patient suffering from another type of locomotor activity and movement related syndrome, disorder, or disease.

Example 36

Treatment of a Neurological or Neurodegenerative Related Syndrome, Disorder, or Disease A 65 year old woman complains that she has trouble remembering. A physician diagnosis the patient with Alzheimer's disease. The woman is treated by taking, once daily, a pill comprising a cannabinoid-2 agonist as disclosed in the present specification. The patient's condition is monitored on a weekly basis and after about 4 week from the start of treatment, the woman indicates that her memory has improved. A physical examination indicates that the disease progression has halted. At two and three month check-ups, the woman indicates that her memory is good and an examination indicates that the cognitive abilities are within the normal range for a woman her age. The reduction in this symptom indicates successful treatment with a composition comprising a cannabinoid-2 agonist as disclosed in the present specification. A similar treatment can be employed for a patient suffering from another type of neurological or neurodegenerative related syndrome, disorder, or disease.

Example 37

Treatment of a Hypreproliferative Related Syndrome, Disorder, or Disease

A 12 year old boy complains of being tired. A physician diagnosis the patient with acute lymphocytic leukemia. The boy is treated intervenously with a drug comprising a cannabinoid-2 agonist as disclosed in the present specification. The patient's condition is monitored on a weekly basis and after about 4 week from the start of treatment, the boy indicates that his energy is returning. A physical examination indicates that the disease progression has halted. At two and three month check-ups, the boy indicates that he does not feel tied anymore and an examination indicates that the leukemia is in remission. The reduction in this symptom indicates successful treatment with a composition comprising a cannabinoid-2 agonist as disclosed in the present specification. A similar treatment can be employed for a patient suffering from another type of hypreproliferative related syndrome, disorder, or disease.

Example 38

Treatment of an Immune or Inflammation Related Syndrome, Disorder, or Disease

A 23 year old man complains of sneezing, has sinus congestion, and a runny nose. A physician diagnosis the patient with an allergy. The man is treated taking, twice daily, a pill comprising a cannabinoid-2 agonist as disclosed in the present specification. The patient's condition is monitored on a weekly basis and after about 1 week from the start of treatment, the man indicates he is not sneezing, the sinus congestion is reduced, and his runny nose has stopped. At two and three month check-ups, the man indicates that he is not sneezing, and that his sinus congestion and runny nose has disappeared. The reduction in these symptoms indicates successful treatment with a composition comprising a cannabinoid-2 agonist as disclosed in the present specification. A similar treatment can be employed for a patient suffering from another type of immune or inflammation related syndrome, disorder, or disease.

Example 39

Treatment of Pain Related Syndrome, Disorder, or Disease

A 33 year old man complains of back pain due to an automobile accident. The man is treated taking, three times daily, a pill comprising a cannabinoid-2 agonist as disclosed in the present specification. The patient's condition is monitored on a weekly basis and after about 1 week from the start of treatment, the man indicates the pain has lessen. At one and three month check-ups, the man indicates that he is not in pain. The reduction in these symptoms indicates successful treatment with a composition comprising a cannabinoid-2 agonist as disclosed in the present specification. A similar treatment can be employed for a patient suffering from another type of pain related syndrome, disorder, or disease.

We claim:
1. A compound of formula I or a pharmaceutically acceptable salt thereof:

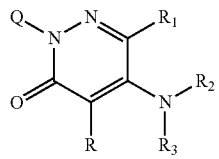

I wherein:
R is selected from the group consisting of H and halogen;
$R_1$ is H;
$R_2$ is unsubstituted or substituted alkyl;
$R_3$ is selected from the group consisting of H and unsubstituted or substituted alkyl; and
Q is the ring-structure of formula II:

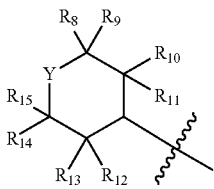

II wherein:
Y is —C($R_6R_7$)—;
$R_6$, $R_7$, $R_{10}$, $R_{11}$, $R_{12}$, and $R_{13}$ are H; and
$R_8$, $R_9$, $R_{14}$, and $R_{15}$ are unsubstituted alkyl.

2. The compound of claim 1, wherein:
$R_2$ is $C_1$-$C_6$ alkyl, or $C_2$-$C_6$ alkyl substituted by N($R_4R_5$);
$R_3$ is H, or $C_1$-$C_6$ alkyl;
$R_4$ and $R_5$ are independently unsubstituted or substituted alkyl, or $NR_4R_5$ is morpholinyl.

3. The compound of claim 1, wherein $R_8$, $R_9$, $R_{14}$, and $R_{15}$ are methyl.

4. A compound selected from the group consisting of 4-Chloro-5-methylamino-2-(3,3,5,5-tetramethylcyclohexyl)pyridazin-3-one, 4-Chloro-5-dimethylamino-2-(3,3,5,5-tetramethylcyclohexyl)pyridazin-3-one, 4-Chloro-5-propylamino-2-(3,3,5,5-tetramethylcyclohexyl)pyridazin-3-one, 5-Methylamino-2-(3,3,5,5-tetramethylcyclohexyl)pyridazin-3-one, 5-Dimethylamino-2-(3,3,5,5-tetramethylcyclohexyl)pyridazin-3-one, 5-Propylamino-2-(3,3,5,5-tetramethylcyclohexyl)pyridazin-3-one, 4-Chloro-5-(2-morpholin-4-ylethylamino)-2-(3,3,5,5-tetramethylcyclohexyl)pyridazin-3-one, 4-Chloro-5-(2-dimethylaminoethylamino)-2-(3,3,5,5-tetramethylcyclohexyl)pyridazin-3-one, 4-Bromo-5-propylamino-2-(3,3,5,5-tetramethylcyclohexyl)pyridazin-3-one, 4-Bromo-5-(2-dimethylaminoethylamino)-2-(3,3,5,5-tetramethylcyclohexyl)pyridazin-3-one, 4-Bromo-5-(2-morpholin-4-ylethylamino)-2-(3,3,5,5-tetramethylcyclohexyl)pyridazin-3-one, 4-Chloro-5-(2-dimethylamino ethylmethylamino)-2-(3,3,5,5-tetramethylcyclohexyl)pyridazin-3-one, and 4-Chloro-5-(2-diethylaminoethylamino)-2-(3,3,5,5-tetramethylcyclohexyl)pyridazin-3-one; or a pharmaceutically acceptable salt thereof.

5. A pharmaceutical composition comprising at least one compound of claim 1 or a pharmaceutically acceptable salt thereof, and at least one pharmaceutically acceptable carrier.

6. A pharmaceutical composition comprising at least one compound of claim 4 or a pharmaceutically acceptable salt thereof, and a pharmaceutically acceptable carrier.

7. The method of treating an eye related syndrome, disorder or disease selected from the group consisting of abnormal intraocular pressure, allergic keratitis, uveitis, or iritis, conjunctivitis, blepharitis, neuritis nervi optici, choroiditis, glaucoma and sympathetic ophthalmia in a subject suffering from said syndrome, disorder of disease, comprising administering to said subject a therapeutically effective amount of at least one compound of claim 1 or a pharmaceutically acceptable salt thereof.

8. A method of treating an eye related syndrome, disorder or disease selected from the group consisting of abnormal intraocular pressure, allergic keratitis, uveitis, or iritis, conjunctivitis, blepharitis, neuritis nervi optici, choroiditis, glaucoma and sympathetic ophthalmia in a subject suffering from said syndrome, disorder of disease, comprising administering to said subject a therapeutically effective amount of at least one compound of claim 4 or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 9,062,004 B2 | Page 1 of 4 |
| APPLICATION NO. | : 13/576872 | |
| DATED | : June 23, 2015 | |
| INVENTOR(S) | : June Chen et al. | |

It is certified that error appears in the above-identified patent and that said Letters Patent is hereby corrected as shown below:

On the title page, item (56), in column 2, under "Other Publications", line 18, delete "Methylhydrazimo)" and insert -- Methylhydrazino) --, therefor.

On the title page, item (56), in column 2, under "Other Publications", line 24, delete "Identfication" and insert -- Identification --, therefor.

On the title page, in column 2, under "Other Publications", line 27, delete "Intermational" and insert -- International --, therefor.

On the title page, in column 2, under "Other Publications", line 28, delete "Declaraion," and insert -- Declaration, --, therefor.

On the title page, in column 2, under "Other Publications", line 30, delete "Activiation" and insert -- Activation --, therefor.

In the specification,

In column 2, line 11, delete "Heterocyclodiazeoine" and insert -- Heterocyclodiazepine --, therefor.

In column 4, line 64, delete "dimethylamino ethylmethylamino" and insert -- dimethylaminoethylmethylamino --, therefor.

In column 5, line 12, delete "$C(R_4R_5)$" and insert -- $C(R_4R_5)$; --, therefor.

In column 6, line 2, delete "$CC_2-C_6$" and insert -- $C_2-C_6$ --, therefor.

In column 6, line 26, delete "$R_7$" and insert -- $R_7$, --, therefor.

In column 7, line 2, delete "tetramethyl cyclohexyl)" and insert -- tetramethylcyclohexyl) --, therefor.

In column 7, line 3, delete "tetramethyl cyclohexyl)" and insert -- tetramethylcyclohexyl) --, therefor.

In column 8, line 25, delete "totyl," and insert -- tolyl, --, therefor.

In column 8, lines 26-27, delete "1-mMethylnaphthalenyl," and insert -- 1-methylnaphthalenyl, --, therefor.

In column 8, line 62, delete "noyl," and insert -- nonyl, --, therefor.

Signed and Sealed this
Eighth Day of December, 2015

Michelle K. Lee
*Director of the United States Patent and Trademark Office*

CERTIFICATE OF CORRECTION (continued)
U.S. Pat. No. 9,062,004 B2

In column 9, line 23, delete "cycloheptene." and insert -- cycloheptene, --, therefor.

In column 9, line 32, delete ""carbocyclealkyl"" and insert -- "carbocycloalkyl" --, therefor.

In column 9, line 67, delete "methylcyclopentad iene." and insert -- methylcyclopentadiene. --, therefor.

In column 10, line 52, delete "bycyclic," and insert -- bicyclic, --, therefor.

In column 11, lines 12-13, delete ""heterocyclealkyl"" and insert -- "heterocycloalkyl" --, therefor.

In column 11, line 27, delete "ariridinyl," and insert -- aziridinyl, --, therefor.

In column 12, line 62, delete "$RNO_2$-," and insert -- $RNO_2$, --, therefor.

In column 13, line 60, delete "thiocarbony," and insert -- thiocarbonyl, --, therefor.

In column 14, line 18, delete "diasteromer;" and insert -- diastereomer; --, therefor.

In column 14, line 36, delete "diasteromer;" and insert -- diastereomer; --, therefor.

In column 14, line 47, delete "sued" and insert -- used --, therefor.

In column 14, line 62, delete "Heterocyclodiazeoine" and insert -- Heterocyclodiazepine --, therefor.

In column 15, line 11, delete "Derivitives" and insert -- Derivatives --, therefor.

In column 15, line 65, delete "sued" and insert -- used --, therefor.

In column 16, line 44, delete "Derivitives," and insert -- Derivatives, --, therefor.

In column 17, line 12, delete "Wermauth" and insert -- Wermuth --, therefor.

In column 20, line 9, delete "dimethylamino ethylmethylamino" and insert -- dimethylaminoethylmethylamino --, therefor.

In column 23, line 45, delete "$C(R_4R_5)$" and insert -- $C(R_4R_5)$; --, therefor.

In column 24, line 62, delete "$R_7$" and insert -- $R_7$, --, therefor.

In column 25, line 37, delete "tetramethyl cyclohexyl)" and insert -- tetramethylcyclohexyl) --, therefor.

In column 25, lines 38-39, delete "tetramethyl cyclohexyl)" and insert -- tetramethylcyclohexyl) --, therefor.

In column 27, line 17, delete "tetramethylcyclophexyl)" and insert -- tetramethylcyclohexyl) --, therefor.

In column 27, line 22, delete "selectiveity" and insert -- selectivity --, therefor.

In column 27, line 25, delete "selectiveity" and insert -- selectivity --, therefor.

In column 27, line 36, delete "selectiveity" and insert -- selectivity --, therefor.

In column 29, line 53, delete "nocicetive" and insert -- nociceptive --, therefor.

In column 31, line 15, delete "C82" and insert -- CB2 --, therefor.

In column 31, line 17, delete "C82" and insert -- CB2 --, therefor.

In column 31, line 21, delete "C82" and insert -- CB2 --, therefor.

In column 31, line 36, delete "C82" and insert -- CB2 --, therefor.

In column 31, line 61, delete "C82," and insert -- CB2, --, therefor.

In column 32, line 13, delete "World Gastroenterol." and insert -- World J. Gastroenterol. --, therefor.

In column 32, line 41, before "Suppl" insert -- 20 --.

In column 33, line 22, delete "MartInez" and insert -- Martinez --, therefor.

In column 33, line 25, delete "O, Sagredo" and insert -- O. Sagredo --, therefor.

In column 34, line 5, delete "C82," and insert -- CB2, --, therefor.

In column 34, line 9, delete "C82" and insert -- CB2 --, therefor.

In column 34, line 10, delete "C82" and insert -- CB2 --, therefor.

In column 34, line 65, delete "hypreproliferative" and insert -- hyperproliferative --, therefor.

In column 35, line 9, delete "hypothalmic" and insert -- hypothalamic --, therefor.

In column 35, line 63, delete "pancreatits;" and insert -- pancreatitis; --, therefor.

In column 36, line 1, delete "opthalmopathy," and insert -- ophthalmopathy, --, therefor.

In column 37, line 16, delete "hypreproliferative" and insert -- hyperproliferative --, therefor.

In column 37, line 17, delete "hypreproliferative" and insert -- hyperproliferative --, therefor.

In column 39, line 25, delete "suppurative," and insert -- suppurativa, --, therefor.

In column 39, line 63, delete "Golfers" and insert -- Golfer's --, therefor.

In column 40, line 4, delete "Behget's disease," and insert -- Behcet's disease, --, therefor.

In column 40, line 4, delete "Behget's disease," and insert -- Behcet's disease, --, therefor.

In column 40, line 12, delete "statis" and insert -- stasis --, therefor.

In column 40, line 13, delete "plaqure" and insert -- plaque --, therefor.

In column 41, line 42, delete "vitaligo." and insert -- vitiligo. --, therefor.

In column 41, line 58, delete "hypreproliferative" and insert -- hyperproliferative --, therefor.

In column 42, line 32, delete "reinopathies," and insert -- retinopathies, --, therefor.

In column 44, line 57, delete "$R_7$" and insert -- $R_7$, --, therefor.

In column 45, line 43, delete "dimethylamino ethylmethylamino" and insert -- dimethylaminoethylmethylamino --, therefor.

In column 46, line 7, delete "hypreproliferative" and insert -- hyperproliferative --, therefor.

In column 46, line 24, delete "$C(R_4R_5)$" and insert -- $C(R_4R_5)$; --, therefor.

In column 47, line 31, delete "$R_7$" and insert -- $R_7$, --, therefor.

In column 47, line 62, delete "tetramethyl cyclohexyl)" and insert -- tetramethylcyclohexyl) --, therefor.

In column 47, lines 63-64, delete "tetramethyl cyclohexyl)" and insert -- tetramethylcyclohexyl) --, therefor.

In column 48, line 34, delete "hypreproliferative" and insert -- hyperproliferative --, therefor.

In column 51, line 43, delete "CDCl3)" and insert -- $CDCl_3$) --, therefor.

In column 52, line 1, delete "tetramethyl cyclohexyl)" and insert -- tetramethylcyclohexyl) --, therefor.

In column 52, line 16, delete "tetramethyl cyclohexyl)" and insert -- tetramethylcyclohexyl) --, therefor.

In column 52, line 32, delete "tetramethyl cyclohexyl)" and insert -- tetramethylcyclohexyl) --, therefor.

In column 52, line 48, delete "tetramethyl cyclohexyl)" and insert -- tetramethylcyclohexyl) --, therefor.

In column 52, line 62, delete "tetramethyl cyclohexyl)" and insert -- tetramethylcyclohexyl) --, therefor.

In column 52, line 67, delete "6H)" and insert -- 6H). --, therefor.

In column 53, line 63, delete "dihydro-yridazine" and insert -- dihydro-pyridazine --, therefor.

In column 53, line 67, delete "yridazine" and insert -- pyridazine --, therefor.

In column 55, line 39, delete "µmol/mg" and insert -- pmol/mg --, therefor.

In columns 57-58, line 73 (Table 1-continued), delete ">>10,000" and insert -- >10,000 --, therefor.

In column 62, line 12, delete "pancreatits." and insert -- pancreatitis. --, therefor.

In column 64, line 36, delete "Hypreproliferative" and insert -- Hyperproliferative --, therefor.

In column 64, line 41, delete "intervenously" and insert -- intravenously --, therefor.

In column 64, line 53, delete "hypreproliferative" and insert -- hyperproliferative --, therefor.

In the claims,

In column 66, lines 25-26, in claim 4, delete "dimethylamino ethylmethylamino)" and insert -- dimethylaminoethylmethylamino) --, therefor.